United States Patent
Nguyen Kim et al.

(10) Patent No.: US 8,821,841 B2
(45) Date of Patent: Sep. 2, 2014

(54) COPOLYMERS FOR COSMETIC APPLICATIONS

(75) Inventors: Son Nguyen Kim, Hemsbach (DE); Marianna Pierobon, Ludwigshafen (DE); Gabi Winter, Shanghai (CN); Matthias Laubender, Schifferstadt (DE); Reinhold Schwalm, Wachenheim (DE)

(73) Assignee: BASF SE (DE)

( * ) Notice: Subject to any disclaimer, the term of this patent is extended or adjusted under 35 U.S.C. 154(b) by 1484 days.

(21) Appl. No.: 12/063,390

(22) PCT Filed: Aug. 2, 2006

(86) PCT No.: PCT/EP2006/064952
§ 371 (c)(1),
(2), (4) Date: Feb. 8, 2008

(87) PCT Pub. No.: WO2007/017434
PCT Pub. Date: Feb. 15, 2007

(65) Prior Publication Data
US 2010/0135918 A1    Jun. 3, 2010

(51) Int. Cl.
*A61Q 5/00* (2006.01)
*A61Q 5/06* (2006.01)

(52) U.S. Cl.
USPC .................. 424/70.1; 424/78.17; 424/70.11; 424/70.16

(58) Field of Classification Search
USPC ................................. 424/70.1, 424
See application file for complete search history.

(56) References Cited

U.S. PATENT DOCUMENTS

| | | | |
|---|---|---|---|
| 3,479,328 A | 11/1969 | Nordstrom | |
| 3,674,838 A | 7/1972 | Nordstrom | |
| 3,836,537 A | 9/1974 | Boerwinkle et al. | |
| 4,116,786 A | 9/1978 | Hodakowski | |
| 4,237,253 A | 12/1980 | Jacquet et al. | |
| 4,260,703 A | 4/1981 | Hodakowski et al. | |
| 4,324,780 A | 4/1982 | Jacquet et al. | |
| 4,481,093 A | 11/1984 | Murphy et al. | |
| 4,814,101 A | 3/1989 | Schieferstein et al. | |
| 5,240,835 A | 8/1993 | Pettrone et al. | |
| 5,442,090 A | 8/1995 | Beck et al. | |
| 5,880,252 A | 3/1999 | Kim et al. | |
| 6,177,535 B1 | 1/2001 | Schwalm et al. | |
| 6,191,181 B1 | 2/2001 | Weikard et al. | |
| 6,207,744 B1 | 3/2001 | Paulus et al. | |
| 6,524,564 B1 | 2/2003 | Kim et al. | |
| 6,617,413 B1 | 9/2003 | Bruchmann et al. | |
| 6,649,323 B2 | 11/2003 | Pappas et al. | |
| 6,800,276 B2 | 10/2004 | Kim et al. | |
| 6,805,872 B2 * | 10/2004 | Mougin | 424/401 |
| 6,932,964 B1 * | 8/2005 | Kim et al. | 424/70.12 |
| 7,164,037 B2 | 1/2007 | Dietsche et al. | |
| 2002/0010264 A1 | 1/2002 | Pappas et al. | |
| 2005/0283733 A1 | 12/2005 | Ellinger et al. | |

FOREIGN PATENT DOCUMENTS

| | | |
|---|---|---|
| AU | 750044 B2 | 3/2001 |
| CA | 2066226 A1 | 3/1991 |
| CA | 2159265 A1 | 3/1996 |
| DE | 1165574 | 3/1964 |
| DE | 2024051 | 12/1971 |
| DE | 2150557 | 6/1972 |
| DE | 2726041 A1 | 12/1977 |
| DE | 2817369 A1 | 10/1978 |
| DE | 3708451 A1 | 10/1988 |
| DE | 3929973 A1 | 3/1991 |
| DE | 4007146 A1 | 9/1991 |
| DE | 4333238 A1 | 4/1995 |
| DE | 4434554 A1 | 4/1996 |
| DE | 19732902 A1 | 2/1999 |
| DE | 19838852 A1 | 3/2000 |
| DE | 10246112 A1 | 5/2004 |
| EP | 0036813 B1 | 10/1978 |
| EP | 0100890 A2 | 2/1984 |
| EP | 0100890 B1 | 2/1984 |
| EP | 0203161 | 12/1986 |
| EP | 0824563 | 2/1998 |
| EP | 0903363 B1 | 3/1999 |
| EP | 0934956 A1 | 8/1999 |
| EP | 0942022 B1 | 9/1999 |
| EP | 1002818 B1 | 5/2000 |
| EP | 1035144 B1 | 9/2000 |
| EP | 1084696 B1 | 3/2001 |
| GB | 962919 | 7/1964 |
| GB | 1333475 | 10/1973 |
| GB | 1443715 | 7/1976 |
| JP | 59157112 A | 9/1984 |

(Continued)

OTHER PUBLICATIONS

Von Wilfried Umbach, H., "Kosmetik and Hygiene von Kopf bis Fuss" 3. Auflage, Wiley-VCH, pp. 235-236, (2004).
International Cosmetic Ingredient Dictionary and Handbook (vol. 4, Herausgeber: RC. Pepe, J.A. Wenninger, G.N., McEwen, The Cosmetic, Toiletry and Fragrance Assoc., 9. Auflage, 2002), Sec. 4.
Macromolecules, vol. 2, 2nd Ed., H.G. Elias, Plenum Press, 1984, New York, Kapitel 20 und 21.
P.K.T. Oldring, Chemistry and Technology of UV- and EB-Formulations for Coatings, Inks and Pains, vol. 11, SITA Technology, London, 1991, pp. 73-123.
S. P. Pappas, J. Rad. Cur., Jul. 1987, S. 6.

(Continued)

*Primary Examiner* — Gina C Justice
(74) *Attorney, Agent, or Firm* — Drinker Biddle & Reath LLP

(57) ABSTRACT

The present invention relates to aqueous skin or hair cosmetic preparations which comprise at least one polymer A which comprises, in copolymerized form, at least one ester of (meth)acrylic acid, at least one olefinically unsaturated, free-radically polymerizable anionogenic or anionic compound, at least one free-radically polymerizable olefinically unsaturated urethane-group-containing compound which comprises no silicone groups and, if appropriate, further free-radically polymerizable compounds.

8 Claims, No Drawings

(56) References Cited

FOREIGN PATENT DOCUMENTS

| | | | |
|---|---|---|---|
| JP | 63297369 A | 12/1988 | |
| WO | WO-86/03145 A1 | 6/1986 | |
| WO | WO-94/25537 A1 | 11/1994 | |
| WO | WO-97/00664 A1 | 1/1997 | |
| WO | WO-97/32917 A1 | 9/1997 | |
| WO | WO-98/06783 A1 | 2/1998 | |
| WO | WO-00/39183 A1 | 7/2000 | |
| WO | WO-01/72862 A3 | 10/2001 | |
| WO | WO-2004/050888 A1 | 6/2004 | |
| WO | WO-2004/052843 A1 | 6/2004 | |
| WO | WO-2004/067599 A1 | 8/2004 | |

\* cited by examiner

COPOLYMERS FOR COSMETIC APPLICATIONS

RELATED APPLICATIONS

This application is a national stage application (under 35 U.S.C. §371) of PCT/EP2006/064952, filed Aug. 2, 2006, which claims benefit of European application 05107388.0, filed Aug. 11, 2005.

The present invention relates to aqueous skin or hair cosmetic preparations which comprise at least one polymer A which comprises, in copolymerized form, at least one ester of (meth)acrylic acid, at least one olefinically unsaturated free-radically polymerizable anionogenic or anionic compound, at least one free-radically polymerizable olefinically unsaturated urethane-group-containing compound comprising no silicone groups and, if appropriate, further free-radically polymerizable compounds.

PRIOR ART

Stricter environmental regulations and a growing ecological awareness increasingly demand ever lower fractions of volatile organic components (VOCs) in, for example, hairsprays.

The VOC content in hairsprays is essentially determined by the nonaqueous solvents and the propellants. For this reason, instead of nonaqueous solvents, recourse is currently and increasingly being made to water as solvent. However, this replacement of the organic solvents has a number of problems particularly in the field of hairspray formulations.

Thus, formulations of the film-forming polymers known from the prior art which satisfy the corresponding VOC regulations are not, for example, sprayable, or are only sprayable following further dilution and are thus only of limited suitability for use in hairsprays. This in turn leads to films which sometimes do not have the required mechanical quality and thus inadequate setting effect and poor hold for the hair.

OBJECT AND SOLUTION

One object of the present invention was to provide polymers for skin or hair cosmetic preparations which can readily be formulated as pump or aerosol spray in solvents or solvent mixtures with an increased water fraction, whose formulations are readily sprayable in the form of small uniform droplets and, during and after application, have the lowest possible tendency for foaming and whose films then formed are not sticky and have good mechanical properties.

Besides the good compatibility with the customary hair cosmetic ingredients, the applied polymers should dry rapidly and impart good setting and prolonged hold to the hair even at increased atmospheric humidity, have a good ability to be washed out and be able to be formulated as optically clear VOC 55 aerosols (i.e. with a VOC fraction of at most 55% by weight). In addition, the treated hair should have good haptic properties such as, in particular, a good feel to the touch.

Surprisingly, these objects were achieved by aqueous skin or hair cosmetic preparations comprising at least one polymer A which comprises in copolymerized form, a) at least one ester of (meth)acrylic acid or ethacrylic acid,
b) at least one olefinically unsaturated, free-radically polymerizable anionogenic or anionic compound,
c) at least one olefinically unsaturated free-radically polymerizable urethane-group-containing compound which comprises no silicone groups and
d) if appropriate further free-radically polymerizable compounds.

WO 97/000664 describes nail varnish preparations based on partially crosslinked acrylic resins which can be prepared by polymerizing 0.1-15% by weight of difunctional urethane (meth)acrylates, 2-20% by weight of an $\alpha,\beta$-olefinically unsaturated $C_3$-$C_{10}$-carboxylic acid, in each case 8-75% by weight of an acrylic ester and a methacrylic ester.

DE-A 198 38 852 describes hair cosmetic preparations comprising polymers which comprise, in incorporated form, as monomer building block, free-radically polymerizable, siloxane-group-containing urethane (meth)acrylates which comprises a) at least one compound which comprises at least one active hydrogen atom and at least one free-radically polymeriable, $\alpha,\beta$-olefinically unsaturated double bond per molecule, b) at least one diisocyanate, c) at least one compound which comprises two active hydrogen atoms per molecule, c) at least one compound which comprises at least one active hydrogen atom and at least one siloxane group per molecule.

Within the scope of the present invention, the expression alkyl comprises straight-chain and branched alkyl groups. Suitable short-chain alkyl groups are, for example, straight-chain or branched $C_1$-$C_{12}$-alkyl, preferably $C_1$-$C_6$-alkyl and particularly preferably $C_1$-$C_4$-alkyl groups. These include, in particular, methyl, ethyl, propyl, isopropyl, n-butyl, 2-butyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methyl propyl, n-heptyl, 2-heptyl, 3-heptyl, 2-ethyl pentyl, 1-propylbutyl, octyl etc.

Suitable longer-chain $C_8$-$C_{30}$-alkyl or $C_8$-$C_{30}$-alkenyl groups are straight-chain and branched alkyl or alkenyl groups. These are preferably predominantly linear alkyl radicals as also arise in natural or synthetic fatty acids and fatty alcohols and also oxo alcohols, which may, if appropriate, additionally be mono-, di- or polyunsaturated. These include, for example, n-hexyl(ene), n-heptyl(ene), n-octyl(ene), n-nonyl(ene), n-decyl(ene), n-undecyl(ene), n-dodecyl(ene), n-tridecyl(ene), n-tetradecyl(ene), n-pentadecyl(ene), n-hexadecyl(ene), n-heptadecyl(ene), n-octadecyl(ene), n-nonadecyl(ene) etc.

Cycloalkyl is preferably $C_5$-$C_8$-cycloalkyl, such as cyclopentyl, cyclohexyl, cycloheptyl or cyclooctyl.

For the purposes of the present invention, the expression heterocycloalkyl comprises saturated, cycloaliphatic groups having generally 4 to 7, preferably 5 or 6, ring atoms, in which 1 or 2 of the ring carbon atoms are replaced by heteroatoms chosen from the elements oxygen, nitrogen and sulfur and which may, if appropriate, be substituted, where in the case of a substitution, these heterocycloaliphatic groups can carry 1, 2 or 3, preferably 1 or 2, particularly preferably 1, substituent chosen from alkyl, aryl, COOR, $COO^-M^+$ and $NE^1E^2$, preferably alkyl. Examples of such heterocycloaliphatic groups which may be mentioned are pyrrolidinyl, piperidinyl, 2,2,6,6-tetramethyl-piperidinyl, imidazolidinyl, pyrazolidinyl, oxazolidinyl, morpholidinyl, thiazolidinyl, isothiazolidinyl, isoxazolidinyl, piperazinyl, tetrahydrothiophenyl, tetrahydrofuranyl, tetrahydropyranyl, dioxanyl.

Aryl comprises unsubstituted and substituted aryl groups and is preferably phenyl, tolyl, xylyl, mesityl, naphthyl, fluorenyl, anthracenyl, phenanthrenyl, naphthacenyl and, in particular, phenyl, tolyl, xylyl or mesityl.

Substituted aryl radicals preferably have 1, 2, 3, 4 or 5, in particular 1, 2 or 3, substituents chosen from alkyl, alkoxy, carboxyl, carboxylate, trifluoromethyl, —SO$_3$H, sulfonate, NE$^1$E$^2$, alkylene-NE$^1$E$^2$, nitro, cyano or halogen.

Hetaryl is preferably pyrrolyl, pyrazolyl, imidazolyl, indolyl, carbazolyl, pyridyl, quinolinyl, acridinyl, pyridazinyl, pyrimidinyl or pyrazinyl.

Arylalkyl is groups which comprise both alkyl and aryl radicals, these arylalkyl groups being joined to the compound carrying them via the aryl radical or via the alkyl radical.

Component a)

Component a) is chosen, for example, from the group consisting of methyl (meth)acrylate, ethyl(meth)acrylate, n-propyl(meth)acrylate, isopropyl(meth)acrylate, methyl ethacrylate, ethyl ethacrylate, n-propyl ethacrylate, isopropyl ethacrylate, n-butyl ethacrylate, tert-butyl ethacrylate, isobutyl ethacrylate, n-butyl(meth)acrylate, tert-butyl(meth)acrylate, isobutyl(meth)acrylate, sec-butyl(meth)acrylate, 2-pentyl(meth)acrylate, 3-pentyl(meth)acrylate, isopentyl acrylate, neopentyl acrylate, n-octyl(meth)acrylate, 1,1,3,3-tetramethylbutyl(meth)acrylate, ethylhexyl(meth)acrylate, n-nonyl(meth)acrylate, n-decyl(meth)acrylate, n-undecyl (meth)acrylate, tridecyl(meth)acrylate, myristyl(meth)acrylate, pentadecyl(meth)acrylate, palmityl(meth)acrylate, heptadecyl(meth)acrylate, nonadecyl(meth)acrylate, arrachinyl (meth)acrylate, behenyl(meth)acrylate, lignocerenyl(meth) acrylate, cerotinyl(meth)acrylate, melissinyl(meth)acrylate, palmitoleinyl(meth)acrylate, oleyl(meth)acrylate, linolyl (meth)acrylate, linolenyl(meth)acrylate, stearyl(meth)acrylate, lauryl(meth)acrylate, phenoxyethyl acrylate, 4-t-butylcyclohexyl acrylate, cyclohexyl(meth)acrylate, ureido(meth) acrylate, tetrahydrofurfuryl(meth)acrylate and mixtures thereof.

Component a) is preferably chosen from the esters of (meth)acrylic acid.

Component a) is particularly preferably chosen from mixtures of methacrylates and acrylates. Preferred (meth)acrylates are C$_1$-C$_{10}$-alkyl(meth)acrylates and in particular C$_1$-C$_4$alkyl(meth)acrylates.

Component a) is very particularly preferably chosen from the group consisting of methyl methacrylate, ethyl methacrylate, n-propyl methacrylate, isopropyl methacrylate, n-butyl methacrylate, tert-butyl methacrylate, isobutyl methacrylate, sec-butyl methacrylate and mixtures thereof.

Component a) is still further preferably chosen from the group consisting of methyl methacrylate, ethyl methacrylate and mixtures thereof.

Component a) is most preferably methyl methacrylate (MMA).

Polymer A comprises preferably 50-95, particularly preferably 65-85 and in particular 70-80% by weight of component a) in copolymerized form.

Component b)

Component b) is an olefinically unsaturated, free-radically polymerizable anionogenic or anionic compound. In this context, an anionogenic compound is understood as meaning a compound which can be converted into the corresponding anionic form by deprotonation with customary, preferably cosmetically acceptable, organic or inorganic bases.

Component b) is preferably chosen from the group of olefinically unsaturated, free-radically polymerizable carboxylic acids and salts thereof.

Component b) is particularly preferably chosen from the group consisting of acrylic acid, methacrylic acid, ethacrylic acid, alpha-chloroacrylic acid, crotonic acid, maleic acid, maleic anhydride, itaconic acid, citraconic acid, mesaconic acid, glutaconic acid, aconitic acid, fumaric acid, half-esters of olefinically unsaturated dicarboxylic acids having 4 to 10, preferably 4 to 6, carbon atoms and salts thereof.

Component b) is very particularly preferably chosen from the group consisting of acrylic acid, methacrylic acid, salts thereof and mixtures thereof.

Polymer A comprises preferably 4-30, particularly preferably 10-30 and in particular 15-28% by weight of component b) in copolymerized form.

Component c)

At least one olefinically unsaturated urethane-group-containing compound which comprises no silicone groups is used as component c). Within the scope of the present invention, olefinically unsaturated urethane-group-containing compounds are understood as meaning compounds which comprise at least one urethane group and at least one polymerizable, preferably free-radically polymerizable, olefinic double bond.

Olefinically unsaturated urethane-group-comprising prepolymers suitable as component c) for the polymers A according to the invention are given, for example, in P.K.T. Oldring (Ed.), Chemistry and Technology of UV- and EB-Formulations for Coatings, Inks and Paints, Vol. 11, SITA Technology, London, 1991, pp. 73-123, which is hereby incorporated in its entirety by reference.

Urethane (meth)acrylates are known to the person skilled in the art. They can be obtained by reacting a di- or polyisocyanate with a chain-extending agent from the group of diols/polyols and/or diamines/polyamines and/or dithiols/polythiols and/or alkanolamines and then reacting the remaining free isocyanate groups with at least one hydroxyalkyl (meth)acrylate or hydroxyalkyl ester of other ethylenically unsaturated carboxylic acids. The amounts of chain-extending agent, di- or polyisocyanate and hydroxyalkyl ester are preferably chosen so that 1. the equivalent ratio of the NCO groups to the reactive groups of the chain-extending agent (hydroxyl, amino or mercaptyl groups) is between 3:1 and 1:2, preferably 2:1, and
2. the OH groups of the hydroxyalkyl esters of the ethylenically unsaturated carboxylic acids are present in stoichiometric amounts with regard to the isocyanate groups of the prepolymer of isocyanate and chain-extending agent which are still free. Furthermore, it is possible to prepare the polyurethane (meth)acrylates by firstly reacting some of the isocyanate groups of a di- or polyisocyanate with at least one hydroxyalkyl ester and then reacting the remaining isocyanate groups with a chain-extending agent. In this case too, the amounts of chain-extending agent, isocyanate and hydroxyalkyl ester are chosen so that the equivalent ratio of the NCO groups to the reactive groups of the chain-extending agent is between 3:1 and 1:2, preferably 2:1, and the equivalent ratio of the remaining NCO groups to the OH groups of the hydroxyalkyl ester is 1:1. All intermediate forms of these two processes are of course also possible. For example, some of the isocyanate groups of a diisocyanate can firstly be reacted with a dial, then some of the other isocyanate groups can be reacted with the hydroxyalkyl ester and, after this, the remaining isocyanate groups can be reacted with a diamine. These various preparation processes for polyurethane(meth)acrylates are known (e.g. from EP-A 0 203 161) and therefore do not require precise description.

Urethane(meth)acrylates suitable as component c) are described in DE-A 198 38 852 p. 3, I. 45 to p. 9, I. 20, which is hereby incorporated in its entirety by reference. The Si component referred to there as d) is, however, not a constituent of those urethane(meth)acrylates which are used within the scope of the present invention as component c).

Urethane(meth)acrylates are understood as meaning compounds which comprise, in incorporated form, I. at least one compound which comprises at least one active hydrogen atom and at least one free-radically polymerizable, α,β-ethylenically unsaturated double bond per molecule,
II. at least one diisocyanate and
III. at least one compound which comprises two active hydrogen atoms per molecule,
and the salts thereof.

Component I

Suitable compounds I are, for example, the customary vinyl compounds known to the person skilled in the art which additionally have at least one group which is reactive toward isocyanate groups and which is preferably chosen from hydroxyl groups, and primary and secondary amino groups. These include, for example, the esters of α,β-ethylenically unsaturated mono- and dicarboxylic acids with at least dihydric alcohols. α/β-Ethylenically unsaturated mono- and/or dicarboxylic acids which can be used are, for example, acrylic acid, methacrylic acid, fumaric acid, maleic acid, crotonic acid, itaconic acid etc. and mixtures thereof. Suitable alcohols are customary diols, triols and polyols, e.g. 1,2-ethanediol, 1,3-propanediol, 1,4-butanediol, 1,5-pentanediol, 1,6-hexanediol, 1,10-decanediol, diethylene glycol, 2,2,4-trimethylpentanediol-1,5, 2,2-dimethylpropanediol-1,3, 1,4-dimethylolcyclohexane, 1,6-dimethylolcyclohexane, glycerol, trimethylolpropane, erythritol, pentaerythritol, sorbitol etc. The compounds I) are then, for example, hydroxymethyl (meth)acrylate, hydroxyethyl ethacrylate, 2-hydroxyethyl (meth)acrylate, 2-hydroxypropyl(meth)acrylate, 3-hydroxypropyl(meth)acrylate, 3-hydroxybutyl(meth)acrylate, 4-hydroxybutyl(meth)acrylate, 6-hydroxyhexyl(meth)acrylate, 3-hydroxy-2-ethylhexyl(meth)acrylate, and di(meth)acrylic esters of 1,1,1-trimethylolpropane or of glycerol. Suitable compounds I are also the esters and amides of the abovementioned α/β-ethylenically unsaturated mono- and dicarboxylic acids with $C_2$- to $C_{12}$-aminoalcohols which have a primary or secondary amino group. These include aminoalkyl acrylates and aminoalkyl methacrylates and N-monoalkyl derivatives thereof which carry, for example, a N—$C_1$- to $C_8$-monoalkyl radical, such as aminomethyl (meth)acrylate, aminoethyl(meth)acrylate, N-methylaminomethyl(meth)acrylate, N-ethylaminomethyl(meth)acrylate, N-ethylaminoethyl(meth)acrylate, N-(n-propyl)aminomethyl(meth)acrylate, N-isopropylaminomethyl (meth)acrylate and preferably tert-butylaminoethyl acrylate and tert-butylaminoethyl methacrylate. These also include N-(hydroxy-$C_1$- to $C_{12}$-alkyl)(meth)acrylamides, such as N-hydroxymethyl(meth)acrylamide, N-hydroxyethyl(meth)acrylamide etc.

Suitable compounds I are also the amides of the abovementioned α/β-ethylenically unsaturated mono- and dicarboxylic acids with di- and polyamines which have at least two primary or two secondary or one primary and one secondary amino group(s). These include, for example, the corresponding amides of acrylic acid and methacrylic acid, such as aminomethyl(meth)acrylamide, aminoethyl(meth)acrylamide, aminopropyl(meth)acrylamide, amino-n-butyl(meth)acrylamide, methylaminoethyl(meth)acrylamide, ethylaminoethyl (meth)acrylamide, methylaminopropyl(meth)acrylamide, ethylaminopropyl(meth)acrylamide, methylamino-n-butyl (meth)acrylamide etc.

Suitable compounds I are also the reaction products of epoxide compounds which have at least one epoxide group with the abovementioned α,β-ethylenically unsaturated mono- and/or dicarboxylic acids and anhydrides thereof. Suitable epoxide compounds of, for example, glycidyl ethers, such as bisphenol A diglycidyl ether, resorcinol diglycidyl ether, 1,3-propanedioldiglycidyl ether, 1,4-butanediol diglycidylether, 1,5-pentanediol diglycidyl ether, 1,6-hexanediol diglycidyl ether etc.

Component II

The component II is customary aliphatic, cycloaliphatic and/or aromatic diisocyanate, such as tetramethylene diisocynate, hexamethylene diisocyanate, methylenediphenyl diisocyanate, 2,4- and 2,6-tolylene diisocyanate and isomer mixtures thereof, o- and m-xylylene diisocyanate, 1,5-naphthylene diisocyanate, 1,4-cyclohexylene diisocyanate, dicyclohexylmethane diisocyanate and mixtures thereof. Preferably, component II is hexamethylene diisocyanate, isophorone diisocyanate, o- and m-xylylene diisocyanate, dicyclohexylmethane diisocyanate and mixtures thereof. If desired, up to 3 mol % of the specified compounds can be replaced by triisocyanates.

Component III

Suitable compounds of component III are, for example, diols, diamines, aminoalcohols, and mixtures thereof. The molecular weight of these compounds is preferably in a range from about 56 to 280. If desired, up to 3 mol % of the specified compounds can be replaced by triols or triamines.

Suitable dials III are, for example, ethylene glycol, propylene glycol, butylene glycol, neopentyl glycol, cyclohexanedimethylol, di-, tri-, tetra-, penta- or hexaethylene glycol and mixtures thereof. Preference is given to using neopentyl glycol and/or cyclohexanedimethylol.

Suitable aminoalcohols III are, for example, 2-aminoethanol, 2-(N-methylamino)ethanol, 3-aminopropanol, 4-aminobutanol, 1-ethyl aminobutan-2-ol, 2-amino-2-methyl-1-propanol, 4-methyl-4-aminopentan-2-ol etc.

Suitable diamines III are, for example, ethylenediamine, propylenediamine, 1,4-diaminobutane, 1,5-diaminopentane and 1,6-diaminohexane.

Preferred compounds of component III are polymers with a number-average molecular weight in the range from about 300 to 5000, preferably about 400 to 4000, in particular 500 to 3000. These include, for example, polyesterdiols, polyetherols, α,ω-diaminopolyethers and mixtures thereof. Preference is given to using polymers which contain ether groups.

The polyetherols III are preferably polyalkylene glycols, e.g. polyethylene glycols, polypropylene glycols, polytetrahydrofurans etc., block copolymers of ethylene oxide and propylene oxide or block copolymers of ethylene oxide, propylene oxide and butylene oxide which comprise the copolymerized alkylene oxide units in random distribution or in the form of blocks.

Suitable α,ω-diaminopolyethers III can be prepared, for example, by amination of polyalkylene oxides with ammonia.

Suitable polytetrahydrofurans III can be prepared by cationic polymerization of tetrahydrofuran in the presence of acidic catalysts, such as, for example, sulfuric acid or fluorosulfuric acid. Such preparation processes are known to the person skilled in the art.

Polyesterdiols III which can be used preferably have a number-average molecular weight in the range from about 400 to 5000, preferably 500 to 3000, in particular 600 to 2000.

Suitable polyesterdiols are all those which are usually used for preparing polyurethanes, in particular those based on aromatic dicarboxylic acids, such as terephthalic acid, isophthalic acid, phthalic acid, Na or K sulfoisophthalic acid etc., aliphatic dicarboxylic acids, such as adipic acid or succinic acid etc., and cycloaliphatic dicarboxylic acids, such as 1,2-, 1,3- or 1,4-cyclohexanedicarboxylic acid. Suitable diols are, in particular, aliphatic dials, such as ethylene glycol, propylene glycol, 1,6-hexanediol, neopentyl glycol, diethylene glycol, polyethylene glycols, polypropylene glycols, 1,4-dimethylolcyclohexane, and poly(meth)acrylatediols of the formula

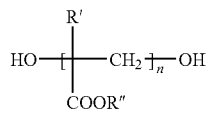

in which R' is H or $CH_3$ and R'' is $C_1$-$C_{18}$-alkyl (in particular $C_1$-$C_{12}$- or $C_1$-$C_8$-alkyl), which have a molar mass of up to about 3000. Such diols can be prepared in the usual manner and are available commercially (Tegomer® grades MD, BD and OD from Goldschmidt).

Preference is given to polyesterdiols based on aromatic and aliphatic dicarboxylic acids and aliphatic diols, in particular those in which the aromatic dicarboxylic acid constitutes 10 to 95 mol %, in particular 40 to 90 mol % and preferably 50 to 85 mol %, of the total amount of dicarboxylic acid (remainder aliphatic dicarboxylic acids).

Particularly preferred polyesterdiols are the reaction products of phthalic acid/diethylene glycol, isophthalic acid/1,4-butanediol, isophthalic acid/adipic acid/1,6-hexanediol, 5-$NaSO_3$-isophthalic acid/phthalic acid/adipic acid/1,6-hexanediol, adipic acid/ethylene glycol, isophthalic acid/adipic acid/neopentyl glycol, isophthalic acid/adipic acid/neopentyl glycol/diethylene glycol/dimethylolcyclohexane and 5-$NaSO_3$-isophthalic acid/isophthalic acid/adipic acid/neopentyl glycol/diethylene glycol/dimethylolcyclohexane.

The compounds of component III can be used individually or as mixtures. Further possible constituents of these urethane (meth)acrylates are to be found in DE-A 198 38 852 p. 5, I. 40 to p. 9, I. 20.

Suitable components c) which may be mentioned are also
c1) Reaction products of the reaction of hydroxy(meth)acrylates with diols and/or OH-terminated polyols and/or OH-terminated polyesters and/or diamines and diisocyanates. Such difunctional urethane acrylate oligomers and their preparation are described, for example, in WO 97/00664, p. 5, I. 17 to p. 6, I. 8 and the corresponding examples, which is hereby incorporated in its entirety by reference.
c2) Carbamoyl oxycarboxylates of the general formula I

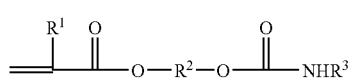

where
$R^1$ is H, halogen or C1-C8-alkyl,
$R^2$ is optionally substituted $C_1$-$C_{12}$-alkylene, -arylene, -alkylarylene or -arylalkylene, polyoxyalkylene,
$R^3$ is $C_1$-$C_8$-alkyl.

Such carbamoyl oxycarboxylates of the general formula I are disclosed in U.S. Pat. No. 3,479,328 and U.S. Pat. No. 3,674,838, which is hereby incorporated in its entirety by reference.
c3) The divinylurethanes disclosed in GB 1 443 715 of the general formula II

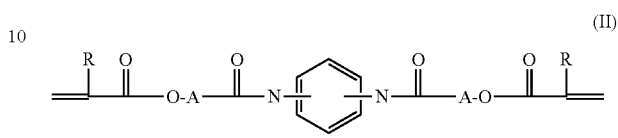

where
R is H or methyl
A is (poly)alkyleneoxy
and vinylurethanes of the general formula III

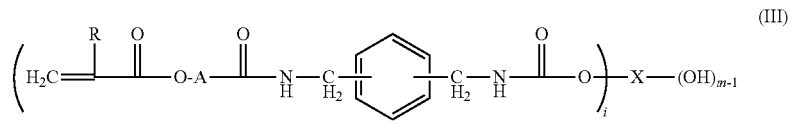

where R and A are as defined in formula II and X and n are as defined in GB 1 443 715 p. 2, II. 9-13. The vinylurethanes likewise described in GB 1 443 715, which is hereby incorporated in its entirety by reference, are further possible components c) of the polymers according to the invention.
c4) The N-substituted carbamoyl oxyalkyleneoxyalkyl (meth)acrylates described in EP-A 0 036 813, which is hereby incorporated in its entirety by reference, of the general formula IV

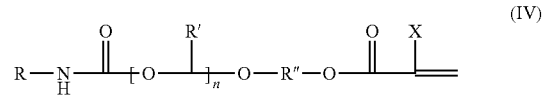

where R, R', R'' and X are as defined in EP-A 0 036 813, p. 2, II. 13-28 and n is an integer from 0 to 20, preferably from 1 to 6 and particularly preferably from 1 to 4.
c5) The urethane acrylate compounds known from DE-A-4 007 146, which is hereby incorporated in its entirety by reference, which are available by reacting polyisocyanates with hydroxyalkyl acrylates, followed by a reaction with primary or secondary amines.
c6) Products of the reaction of isocyanates with polyols and hydroxyalkyl acrylates as described, for example, in DE 27 26 041 A, U.S. Pat. No. 4,260,703 and U.S. Pat. No. 4,481,093 and products of the reaction of isocyanates with hydroxyalkyl acrylates as described in JP 63297369 and JP 59157112, which is hereby incorporated in its entirety by reference.
c7) The urethane-group-comprising prepolymers described in EP-A 0 903 363, which is hereby incorporated in its entirety by reference, which can be prepared by a process in which an isocyanate-group-comprising component A is reacted with an OH-group-comprising component B, where component A comprises at least one trifunctional isocyanate compound A1 and, if appropriate, one or more difunctional isocyanate compounds A2, and the OH-group-comprising component B comprises at least one olefinically unsaturated compound B1 with at least one reactive OH group and, if appropriate, OH-group-comprising compounds B2 different therefrom, where either component A comprises two different isocyanate compounds A1 or one isocyanate compound A1 and at least one isocyanate compound A2, or component B comprises at least two different compounds B2.

c8) Polyurethane polymers which comprise, in copolymerized form, A) 40 to 80% by weight, based on the total weight of components A) to F), of at least one hydroxyl-group-containing prepolymer with at least one free-radically or photochemically polymerizable α,β-ethylenically unsaturated double bond, where the prepolymer A) is a reaction product or a mixture of a) at least one polyester acrylate and/or polyether acrylate and/or polyurethane acrylate and b) at least one epoxy acrylate,
B) 0.1 to 20% by weight, based on the total weight of components A) to F), of at least one compound with at least one hydroxyl and/or primary or secondary amino group which is reactive toward isocyanate groups and additionally at least one polar functional group,
C) 0.1 to 10% by weight, based on the total weight of components A) to F), of at least one compound chosen from diamines, polyamines and mixtures thereof,
D) 0 to 20% by weight, based on the total weight of components A) to F), of at least one further compound, different from A), B), C) and E), with at least two groups which are reactive toward isocyanate groups, which are hydroxyl groups and mixtures of hydroxyl groups and/or primary or secondary amino groups,
E) 0 to 20% by weight, based on the total weight of components A) to F), of at least one compound with a group which is reactive toward isocyanate groups,
F) 10 to 50% by weight, based on the total weight of components A) to F), of at least one polyisocyanate, and the salts thereof, wherein the sum of the hydroxyl numbers of the components A) and D) is in a range from 121 to 300 mg of KOH/g.

These polyurethane polymers are described in EP-A 0 942 022, which is hereby incorporated in its entirety by reference.

c9) The reaction products described in EP-A 1 002 818 (which are hereby incorporated in their entirety by reference) of a) isocyanate trimer (mixtures) based on aliphatic or cycloaliphatic diisocyanates which consist of up to 100 mol % of compounds of the iminooxadiazinedione structure type of the formula A

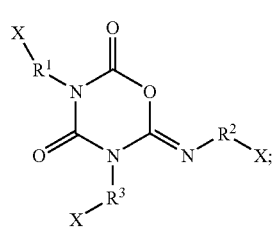

in which $R^1$, $R^2$ and $R^3$, independently of one another, are optionally branched $C_4$-$C_{20}$-(cyclo)alkylene, and X is identical or different radicals of isocyanate or of isocyanate secondary products which of the iminooxadiazinedione, isocyanurate, uretdione, urethane, allophanate, biuret or oxadiazinetrione structure type and carry the abovementioned radicals $R^1$, $R^2$ and $R^3$ in the N position, with b) an alcohol component which comprises at least one monovalent hydroxy-functional optionally branched $C_1$-$C_{12}$-alkyl ester of (meth)acrylic acid.

c10) The allyl-group-comprising polyurethanes of the general formula V, as disclosed in WO 01/72862, which is hereby incorporated in its entirety by reference:

The meanings of R, $R^1$, y, m and n are described in WO 01/72862 on p. 3, l. 29 to p. 4, l. 10.

c11) The urethane-group-containing (meth)acrylic esters described in WO 04/050888, which is hereby incorporated in its entirety by reference, which can be prepared by reacting a urethane-group-containing alcohol with (meth)acrylic acid or an ester of (meth)acrylic acid with a saturated alcohol and, if appropriate, purification of the reaction mixture, the reaction being carried out in the presence of an enzyme (E).

c12) The urethane(meth)acrylate oligomers described in WO 98/06783, which is incorporated at this point in its entirety by reference, in particular on p. 1, l. 22 to p. 2, l. 6.

c13) The polyurethanes described in DE 44 34 554 A1, which is incorporated at this point in its entirety by reference, in particular on p. 2, l. 42 to p. 4, l. 27.

c14) The urethane (meth)acrylate oligomers described in WO 04/067599, which is hereby incorporated in its entirety by reference, in particular on p. 10, l. 24 to p. 12, l. 13.

c15) The urethane acrylates described in U.S. Pat. No. 5,240, 835, which is incorporated at this point in its entirety by reference, which can be prepared by the transesterification of alkyl acrylates with alcohols with catalysis of a biocatalyst from Corynebacterium oxydans.

c16) The carbamoyl oxy(meth)acrylates described in WO 04/052843, which is incorporated at this point in its entirety by reference, which can be prepared by a process as described on p. 3, l. 34 to p. 10, l. 28 of WO 04/052843.

c17) The carbamyl oxy(meth)acrylates which are described in WO 94/25537 p. 8, l. 29 to p. 9, l. 32, which is incorporated at this point in its entirety by reference.

c18) The polyisocyanate secondary products described in DE-A 102 46 112, which is hereby incorporated in its entirety by reference, comprising at least one allophanate group which carries at least one acrylate, methacrylate or vinyl ether double bond on the oxygen atom of the allophanate group bonded via two single bonds, wherein a polyisocyanate or polyisocyanate secondary product comprising at least one oxadiazine trione group reacts with an alcohol comprising acrylate, methacrylate or vinyl ether double bond at temperatures between −20 to 100° C.

c19) WO 00/39183, which is hereby incorporated in its entirety by reference, describes compounds with isocyanate groups or capped isocyanate groups, allophanate groups and free-radically polymerizable C—C double bonds, where the C—C double bonds are activated by a carbonyl group bonded directly thereto or an O atom in ether function (activated double bonds), derived from polyisocyanates and alcohols A which also carry an activated double bond besides the alcohol group.

According to the invention, these compounds are preferably reacted with alcohols RON which carry only one OH group, or with amines $RNH_2$ or RR'NH in at least an amount which suffices to convert all of the isocyanate groups and capped isocyanate groups into urethane or urea groups.

Here, R and R', independently of one another, are $C_1$-$C_{12}$-alkyl, -aryl, -alkylaryl or -arylalkyl, polyoxyalkylene, where the radicals may, if appropriate, be functionalized with hydroxyl groups.

Preferred alcohols for this reaction are $C_1$-$C_{12}$-, in particular $C_1$-$C_4$-alkanols, such as, for example, methanol, ethanol, n-propanol, isopropanol, n-butanol, isobutanol, sec-butanol, tert-butanol.

Preferred amines for this reaction are $C_1$-$C_{12}$-, in particular $C_1$-$C_4$-(di)alkylamines, (di)alkanolamines, alkylalkanolamines, such as, for example, ethylamine, butylamine, diethylamine, ethanolamine, diethanolamine, 2-amino-2-methylpropanol.

In this way, compounds of the following general formulae, for example, are obtained:

from the reaction with alcohols:

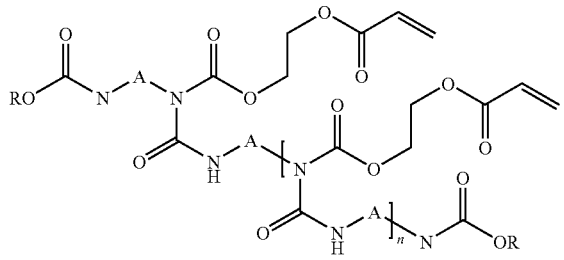

from the reaction with amines:

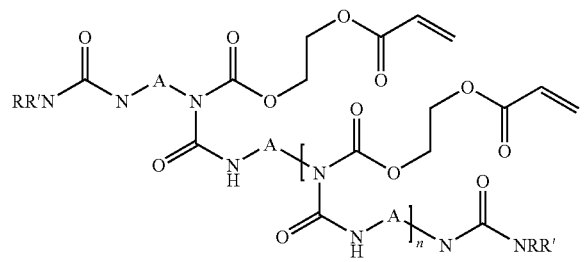

where
R is $C_1$-$C_{12}$-alkyl, -aryl, -alkylaryl or -arylalkyl, polyoxyalkylene, if appropriate functionalized with hydroxyl groups
R' is H, $C_1$-$C_{12}$-alkyl, -aryl, -alkylaryl or -arylalkyl, polyoxyalkylene, if appropriate functionalized with hydroxyl groups
n is 0 to 10, preferably 0 to 5, particularly preferably 0 to 2
A is $C_1$-$C_{12}$-alkylene, -arylene, -alkylarylene or -arylalkylene, polyoxyalkylene
and mixtures thereof.

It is of course also possible to use the corresponding methacrylate derivatives of these compounds as component c).

Suitable components c) are, for example, also c20) N-butyl-2-hydroxyethyl carbamates (CAS 63225-53-6) of the formula

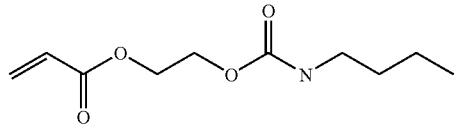

(commercially available as, for example, Ebecryl®CL 1039 (UCB)) and the corresponding methacrylic acid derivative, c21) N-methyl-2-hydroxyethyl carbamates (CAS 52607-81-5) of the formula

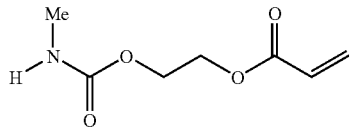

and the corresponding methacrylic acid derivative, c22) one of the or a mixture of the two components of the following formulae (the mixture is referred to here as monomer C22 (see also the examples)):

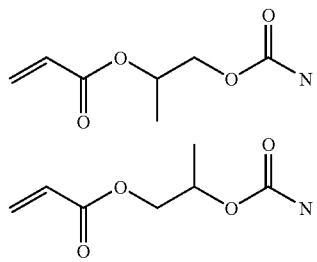

and the corresponding methacrylic acid derivatives, c23) one of the or a mixture of the two components of the following formulae

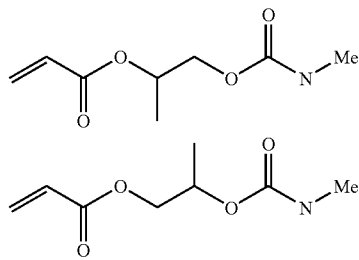

and the corresponding methacrylic acid derivatives, c24) compound of the following formula:

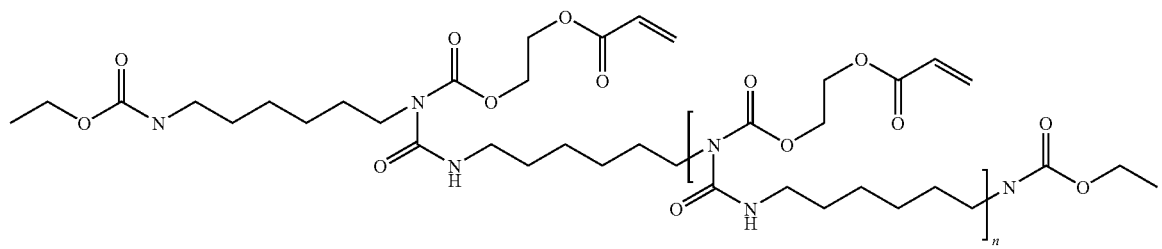

where n is 0 to 10, preferably 0 to 4, particularly preferably 0 to 2, and the corresponding methacrylic acid derivatives.

c25) Diurethane dimethacrylate 7,7,9-(or 7,9,9-)trimethyl-4,13-dioxo-3,14-dioxa-5,12-diazahexadecane-1,16-diol dimethacrylate (CAS 72869-86-4), which is commercially available, for example, as PLEX®6661-O (Degussa).

Polyurethane (meth)acrylates suitable as component e) as polyurethane mono-, di-, tri-, tetra-, penta- or hexa(meth)acrylates are commercially available under the brands Laromer® (BASF), Photomer® (Cognis), Sartomer® (Sartomer) or Ebecryl® (UCB).

They can be used in pure form (without diluents), as solutions in solvents such as ethanol or butyl acetate or as solutions in reactive diluents (such as, for example, tripropylene glycol diacrylate (TPGDA), hexanediol diacrylate (HDDA), dipropylene glycol diacrylate (DPGDA), trimethylolpropane formal monoacrylate (Laromer®LR 8887), trimethylolpropane triacrylate (TMPTA), propoxylated glyceryl triacrylate (GPTA), ethoxylated trimethylolpropane triacrylate (EO3TMPTA), ethoxyethoxyethyl acrylate (EOEOEA), PEG 400 diacrylate (PEG400DA), isobornyl acrylate (IBOA), propoxylated neopentyl glycol diacrylate (PO2NPGDA), 2-phenoxyethyl acrylate (POEA), butanediol diacrylate (BDDA), butanediol acrylate (BDMA), dihydrodicyclopentadienyl acrylate (DCPA), triethylene glycol divinyl ether, ethyl digycol acrylate (EDGA), lauryl acrylate (LA), 4-t-butylcyclohexyl acrylate (TBCH) or as aqueous emulsions.

Such polyurethane (meth)acrylates are:

Laromer® grades Laromer grades LR 8949, LR 9005, LR 8983, UA 19 T, UA 9030V, UA 9028V, UA 9029V, UA 9033V, UA 9031V and LR 8987, Photomer® grades 6891, 6892, 6893-20R, 6572, 6010, 6019, 6184, 6210, 6217, 6230, 6363 and 6008

Sartomer®CN grades, such as, for example, the aliphatic urethane acrylates CN 934 CN 934X50, ON 944B85, CN 945A60, CN 945B85, CN 953B70, CN 961 E75, CN 961 H81, CN 962, CN 963A80, CN 963880, CN 963E75, CN 963E80, CN 963J85, ON 964, CN 964A85, CN 964B85, CN 964H90, CN 964E75, CN 965, CN 965A80, CN 966A80, CN 966B385, CN 966H90, CN 966180, CN 966J75, CN 966R60, CN 968, CN 982E75, CN 982P90, CN 983, CN 983B88, CN 984, CN 985B88 and the aromatic urethane acrylates CN 970A60, CN 970E60, CN 970H75, CN 971A80, CN 972, CN 973A80, CN 973H85, CN 973J75, CN 975, CN 977C70, CN 978, CN 980, CN 980M50, CN 981, CN 981A75, CN 981B88, CN 982A75, CN 982B88

Ebecryl® grades, such as, for example, 220, 230, 244, 264, 265, 270.

As component c), particular preference is given to carbamoyl oxycarboxylates of the general formula VIII

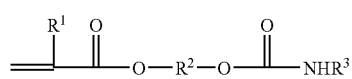

(VIII)

where
$R^1$ is H, halogen, $C_1$-$C_8$-alkyl, preferably H or methyl,
$R^2$ is optionally substituted $C_1$-$C_{12}$-alkylene, -arylene, -alkylarylene or -arylalkylene, optionally hydroxy-substituted polyoxyalkylene,
$R^3$ is H, $C_1$-$C_8$-alkyl.

In general, preference is given to those components c) which comprise at most 4, preferably at most 3 and particularly preferably at most 2, free-radically polymerizable double bonds per molecule.

Polymer A comprises preferably 0.1-20, particularly preferably 0.5-10 and most preferably 0.5-5% by weight of component c) in copolymerized form.

In one embodiment of the invention, polymer A comprises
a) methylmethacrylate,
b) methacrylic acid and/or acrylic acid,
c) N-butyl-2-hydroxyethyl carbamates of the general formula

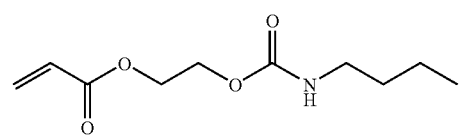

in copolymerized form.

In a further embodiment of the invention, polymer A comprises
a) ethyl methacrylate,
b) methacrylic acid and/or acrylic acid,
c) N-butyl-2-hydroxyethyl carbamates of the general formula

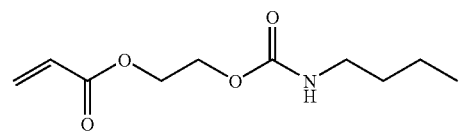

in copolymerized form.

In a further embodiment of the invention, polymer A comprises
a) methyl methacrylate,
b) methacrylic acid and/or acrylic acid,
c) a mixture of the two components of the following formulae

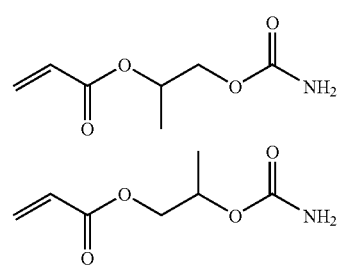

in copolymerized form.

In a further embodiment of the invention, polymer A comprises
a) ethyl methacrylate,
b) methacrylic acid and/or acrylic acid,
c) a mixture of the two components of the following formulae

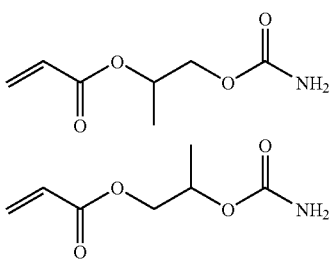

in copolymerized form.

Component d)

Suitable components d) are generally all free-radically polymerizable, unsaturated compounds which are different from the components a) to c) and which can be copolymerized with components a) to c).

Preferred components d) are
d1) compounds containing amide groups different from d2),
d2) (meth)acrylamides,
d3) cationogenic monomers,
d4) cationic monomers and
d5) compounds with at least two polymerizable double bonds, which are usually also referred to as crosslinkers.

Component d1)

The compounds d1) containing amide groups are preferably chosen from compounds which are different from d2) and of the general formula VI

(VI)

where $R^1$ is a group of the formula $CH_2=CR_4-$ where $R^4=H$ or $C_1$-$C_4$-alkyl and $R^2$ and $R^3$, independently of one another, are H, alkyl, cycloalkyl, heterocycloalkyl, aryl or hetaryl or $R^2$ and $R^3$ together with the nitrogen atom to which they are bonded are a five- to eight-membered nitrogen heterocycle or $R^2$ is a group of the formula $CH_2=CR^4-$ and $R^1$ and $R^3$, independently of one another, are H, alkyl, cycloalkyl, heterocycloalkyl, aryl or hetaryl or Wand $R^3$ together with the amide group to which they are bonded are a lactam having 5 to 8 ring atoms.

Preferred components d1) are N-vinyllactams. Suitable components d1) are unsubstituted N-vinyllactams and N-vinyllactam derivatives, which can, for example, have one or more $C_1$-$C_6$-alkyl substituents, such as methyl, ethyl, n-propyl, isopropyl, n-butyl, sec-butyl, tert-butyl etc. These include, for example, N-vinylpyrrolidone, N-vinylpiperidone, N-vinylcaprolactam, N-vinyl-5-methyl-2-pyrrolidone, N-vinyl-5-ethyl-2-pyrrolidone, N-vinyl-6-methyl-2-piperidone, N-vinyl-6-ethyl-2-piperidone, N-vinyl-7-methyl-2-caprolactam, N-vinyl-7-ethyl-2-caprolactam etc. and mixtures thereof.

Preferred components d1) are those for which, in formula VI, $R^2$ is $CH_2=CH-$ and $R^1$ and $R^3$ together with the amide group to which they are bonded are a lactam having 5 ring atoms.

Particular preference is given to using N-vinylpyrrolidone, N-vinylcaprolactam, N-vinylformamide, acrylamide or mixtures thereof, with N-vinylpyrrolidone being most preferred.

Component d2)

Suitable components d2) are the amides of (meth)acrylic acid different from d3) and d4). Such amides are, for example, (meth)acrylamide, N-methyl(meth)acrylamide, N-ethyl (meth)acrylamide, N-n-propyl(meth)acrylamide, N-i-propyl (meth)acrylamide, N-(n-butyl)methacrylamide, N-(sec-butyl)methacrylamide, N-(tert-butyl)methacrylamide, N-(n-pentyl)(meth)acrylamide, N-(n-hexyl)(meth)acrylamide, N-(n-heptyl)(meth)acrylamide, N-(n-octyl)(meth)acrylamide, N-(tert-octyl)(meth)acrylamide N-(1,1,3,3-tetramethylbutyl)(meth)acrylamide, N-ethylhexyl(meth)acrylamide, N-(n-nonyl)(meth)acrylamide, N-(n-decyl)(meth)acrylamide, N-(n-undecyl)(meth)acrylamide, N-tridecyl(meth) acrylamide, N-myristyl(meth)acrylamide, N-pentadecyl (meth)acrylamide, N-palmityl(meth)acrylamide, N-heptadecyl(meth)acrylamide, N-nonadecyl(meth)acrylamide, N-arrachinyl(meth)acrylamide, N-behenyl(meth)acrylamide, N-lignocerenyl(meth)acrylamide, N-cerotinyl(meth) acrylamide, N-melissinyl(meth)acrylamide, N-palmitoleinyl (meth)acrylamide, N-oleyl(meth)acrylamide, N-linolyl (meth)acrylamide, N-linolenyl(meth)acrylamide, N-stearyl (meth)acrylamide, N-lauryl(meth)acrylamide.

Suitable components d2) are also 2-hydroxyethylacrylamide, 2-hydroxyethylmethacrylamide, 2-hydroxyethylethacrylamide, 2-hydroxypropylacrylamide, 2-hydroxypropylmethacrylamide, 3-hydroxypropylacrylamide, 3-hydroxypropylmethacrylamide, 3-hydroxybutylacrylamide, 3-hydroxybutylmethacrylamide, 4-hydroxybutylacrylamide, 4-hydroxybutylmethacrylamide, 6-hydroxyhexylacrylamide, 6-hydroxyhexylmethacrylamide, 3-hydroxy-2-ethylhexylacrylamide and 3-hydroxy-2-ethylhexylmethacrylamide.

Components d3) and d4)

The components d3) and d4) are monomers which comprise at least one cationogenic and/or cationic group per molecule.

Preferably, the cationogenic and cationic groups are nitrogen-containing groups, such as primary, secondary and tertiary amino groups, and quaternary ammonium groups. The nitrogen-containing groups are preferably tertiary amino groups.

The components d3) and d4) are preferably used for the polymerization in uncharged form. However, use in charged form is also suitable.

Charged cationic groups can be produced, for example, from the amine nitrogen atoms by protonation, for example with monobasic or polybasic carboxylic acids, such as lactic acid or tartaric acid, or mineral acids, such as phosphoric acid, sulfuric acid and hydrochloric acid.

The components d3) and d4) are preferably chosen from
  esters of α,β-olefinically unsaturated mono- and dicarboxylic acids with amino alcohols, which may be mono- or dialkylated on the amine nitrogen,
  amides of α,β-olefinically unsaturated mono- and dicarboxylic acids with diamines which have at least one primary or secondary amino group,
  N,N-diallylamine,
  N,N-diallyl-N-alkylamines and derivatives thereof,
  vinyl- and allyl-substituted nitrogen heterocycles,
  vinyl- and allyl-substituted heteroaromatic compounds and
  mixtures thereof.

Suitable components d3) and d4) are also the esters of α,β-olefinically unsaturated mono- and dicarboxylic acids with amino alcohols. Preferred amino alcohols are $C_2$-$C_{12}$-aminoalcohols which are $C_1$-$C_8$-mono- or -dialkylated on the amine nitrogen. Suitable acid components of these esters are, for example, acrylic acid, methacrylic acid, fumaric acid, maleic acid, itaconic acid, crotonic acid, maleic anhydride, monobutyl maleate and mixtures thereof. Preference is given to using acyrlic acid, methacrylic acid and mixtures thereof.

Particularly preferred components d3) and d4) are N-methylaminoethyl(meth)acrylate, N-ethylaminoethyl(meth)acrylate, N-(n-propyl)aminoethyl(meth)acrylate, N-(n-butyl)aminoethyl(meth)acrylate, N-(tert-butyl)aminoethyl(meth)acrylate, N,N-dimethylaminomethyl(meth)acrylate, N,N-dimethylaminoethyl(meth)acrylate, N,N-diethylaminoethyl(meth)acrylate, N,N-dimethylaminopropyl(meth)acrylate, N,N-diethylaminopropyl(meth)acrylate and N,N-dimethylaminocyclohexyl(meth)acrylate.

In particular, the components d3) and d4) used are N-(tert-butyl)aminoethyl acrylate and N-(tert-butyl)aminoethyl methacrylate.

Suitable components d3) and d4) are also the amides of the abovementioned α,β-olefinically unsaturated mono- and dicarboxylic acids with diamines which have at least one primary or secondary amino group.

Preference is given to diamines which have one tertiary and one primary or secondary amino group. As components d3) and d4), preference is given to using N-[2-(dimethylamino)ethyl]acrylamide, N[2-(dimethylamino)ethyl]methacrylamide, N-[3-(dimethylamino)propyl]acrylamide, N-[3-(dimethylamino)propyl]methacrylamide, N-[4-(dimethylamino)butyl]acrylamide, N-[4-(dimethylamino)butyl]methacrylamide, N-[2-(diethylamino)ethyl]acrylamide, N-[4-(dimethylamino)cyclohexyl]acrylamide and N-[4-(dimethylamino)cyclohexyl]methacrylamide.

Particular preference is given to using N[3-(dimethylamino)propyl]acrylamide and/or N-[3-(dimethylamino)propyl]methacrylamide.

Suitable components d3) and d4) are also N,N-diallyiamines and N,N-diallyl-N-alkylamines and acid addition salts thereof. Alkyl here is preferably $C_1$-$C_{24}$-alkyl. Preference is given to N,N-diallyl-N-methylamine.

Suitable components d3) and d4) are also vinyl- and allyl-substituted nitrogen heterocycles, such as N-vinylimidazole, N-vinylimidazole derivatives, e.g. N-vinyl-2-methylimidazole, vinyl- and allyl-substituted heteroaromatic compounds, such as 2- and 4-vinylpyridine, 2- and 4-allylpyridine, and the salts thereof.

Suitable components d3) and d4) are also N-vinylimidazoles of the general formula VII in which $R^1$ to $R^3$ are hydrogen, $C_1$-$C_4$-alkyl or phenyl

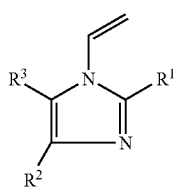

(VII)

Examples of compounds of the general formula VII are given in table 1 below:

TABLE 1

| $R^1$: | $R^2$: | $R^3$: |
|---|---|---|
| H | H | H |
| Me | H | H |
| H | Me | H |

TABLE 1-continued

| $R^1$: | $R^2$: | $R^3$: |
|---|---|---|
| H | H | Me |
| Me | Me | H |
| H | Me | Me |
| Me | H | Me |
| Ph | H | H |
| H | Ph | H |
| H | H | Ph |
| Ph | Me | H |
| Ph | H | Me |
| Me | Ph | H |
| H | Ph | Me |
| H | Me | Ph |
| Me | H | Ph |

Me = methyl;
Ph = phenyl

The components d3) and d4) are particularly preferably chosen from N-(tert-butyl-amino)ethyl(meth)acrylate, N,N-dimethylaminoethyl(meth)acrylate, N-[3-(dimethylamino)propyl](meth)acrylamide, vinylimidazole and mixtures thereof.

If the polymers A according to the invention comprise components d3) and/or d4) in copolymerized form, then they comprise at least 0.1% by weight, preferably at least 1% by weight, particularly preferably at least 2% by weight and in particular at least 3% by weight and at most 30% by weight, preferably at most 20% by weight, particularly preferably at most 15% by weight and in particular at most 10% by weight of the components d3) and/or d4), based on the total weight of the components a) to d) used.

The charged cationic groups can be produced from the amine nitrogens by quaternization with so-called alkylating agents. Examples of suitable alkylating agents are $C_1$-$C_4$-alkyl halides or sulfates, such as ethyl chloride, ethyl bromide, methyl chloride, methyl bromide, dimethyl sulfate and diethyl sulfate. A quaternization can generally take place either before or after the polymerization.

Component d5)

Component d5) are compounds with at least two free-radically polymerizable nonconjugated double bonds per molecule.

Suitable components d5) are, for example, acrylates, methacrylates, allyl ethers or vinyl ethers of at least dihydric alcohols. The OH groups of the parent alcohols here may be completely or partially etherified or esterified; however, the components d5) comprise at least two free-radically polymerizable unsaturated groups.

Examples of the parent alcohols are dihydric alcohols, such as 1,2-ethanediol, 1,2-propanediol, 1,3-propanediol, 1,2-butanediol, 1,3-butanediol, 2,3-butanediol, 1,4-butanediol, but-2-ene-1,4-diol, 1,2-pentanediol, 1,5-pentanediol, 1,2-hexanediol, 1,6-hexanediol, 1,10-decanediol, 1,2-dodecanediol, 1,12-dodecanediol, neopentyl glycol, 3-methylpentane-1,5-diol, 2,5-dimethyl-1,3-hexanediol, 2,2,4-trimethyl-1,3-pentanediol, 1,2-cyclohexanediol, 1,4-cyciohexanediol, 1,4-bis(hydroxymethyl)cyclohexane, neopentyl glycol monohydroxypivalate, 2,2-bis(4-hydroxyphenyl)propane, 2,2-bis[4-(2-hydroxypropyl)phenyl]propane, diethylene glycol, triethylene glycol, tetraethylene glycol, dipropylene glycol, tri propylene glycol, tetrapropylene glycol, 3-thiopentane-1,5-dial, and polyethylene glycols, polypropylene glycols and polytetrahydrofurans with molecular weights of in each case 200 to 10 000.

Apart from the homopolymers of ethylene oxide and propylene oxide, it is also possible to use block copolymers of ethylene oxide or propylene oxide or copolymers which comprise incorporated ethylene oxide and propylene oxide groups.

Examples of parent alcohols with more than two OH groups are trimethylolpropane, glycerol, pentaerythritol, 1,2,5-pentanetriol, 1,2,6-hexanetriol, triethoxycyanuric acid, sorbitan, sugars, such as sucrose, glucose, mannose. Preferred polyhydric alcohols in this connection are also di- and trisaccharides.

The polyhydric alcohols can of course also be used following reaction with ethylene oxide or propylene oxide in the form of the corresponding ethoxylates or propoxylates. The polyhydric alcohols can also firstly be converted to the corresponding glycidyl ethers by reaction with epichlorohydrin.

Further suitable components d5) are the vinyl esters or the esters of monohydric, unsaturated alcohols with olefinically unsaturated $C_3$- to $C_6$-carboxylic acids, for example acyrlic acid, methacrylic acid, itaconic acid, maleic acid or fumaric acid. Examples of such alcohols are allyl alcohol, 1-buten-3-ol, 5-hexen-1-ol, 1-octen-3-ol, 9-decen-1-ol, dicyclopentenyl alcohol, 10-undecen-1-ol, cinnamyl alcohol, citronellol, crotyl alcohol or cis-9-octadecen-1-ol. However, it is also possible to esterify the monohydric unsaturated alcohols with polybasic carboxylic acids, for example malonic acid, tartaric acid, trimellitic acid, phthalic acid, terephthalic acid, citric acid or succinic acid.

Further suitable components d5) are esters of unsaturated carboxylic acids with the above-described polyhydric alcohols, for example oleic acid, crotonic acid, cinnamic acid or 10-undecenoic acid.

Suitable components d5) are also straight-chain or branched, linear or cyclic, aliphatic or aromatic hydrocarbons which have at least two double bonds which, in the case of aliphatic hydrocarbons, must not be conjugated, e.g. divinylbenzene, divinyltoluene, 1,7-octadiene, 1,9-decadiene, 4-vinyl-1-cyclohexene, trivinylcyclohexane or polybutadienes with molecular weights of from 200 to 20 000.

Further suitable components d5) are also the amides of (meth)acrylic acid, itaconic acid and maleic acid, and N-allylamines of at least difunctional amines. Such amines are, for exmaple, 1,2-diaminomethane, 1,2-diaminoethane, 1,3-diaminopropane, 1,4-diaminobutane, 1,6-diaminohexane, 1,12-dodecanediamine, piperazine, diethylenetriamine or isophoronediamine. Likewise suitable are the amides of allylamine and unsaturated carboxylic acids, such as acrylic acid, methacrylic acid, itaconic acid, maleic acid, or at least dibasic carboxylic acids, as have been described above.

Also suitable are triallylamine and triallylmonoalkylammonium salts, e.g. triallylmethylammonium chloride or methyl sulfate, as component d5).

Also suitable are N-vinyl compounds of urea derivatives, at least difunctional amides, cyanurates or urethanes, for example of urea, ethyleneurea, propyleneurea or tartramide, e.g. N,N'-divinylethyleneurea or N,N'-divinylpropyleneurea.

Also suitable as alkylenebisacrylamides, such as methylenebisacrylamide and N,N'-(2,2)butane and 1,1'-bis(3,3'-vinylbenzimidazolith-2-one)-1,4-butane.

Other suitable components d5) are, for example, alkylene glycol di(meth)acrylates, such as ethylene glycol diacrylate, ethylene glycol dimethacrylate, tetraethylene glycol acrylate, tetraethylene glycol dimethacrylate, diethylene glycol acrylate, diethylene glycol methacrylate, vinyl acrylate, allyl acrylate, allyl methacrylate, divinyldioxane, pentaerythritol allyl ether and mixtures of these components d5).

Further suitable components d5) are divinyldioxane, tetraallylsilane or tetravinylsilane.

Particularly preferred components d5) used are, for example, methylenebisacrylamide, triallylamine and triallylalkylammonium salts, divinylimidazole, pentaerythritol triallyl ether, N,N'-divinylethyleneurea, reaction products of polyhydric alcohols with acrylic acid or methacrylic acid, methacrylic esters and acrylic esters of polyalkylene oxides or polyhydric alcohols which have been reacted with ethylene oxide and/or propylene oxide and/or epichlorohydrin.

Very particularly preferred components d5) are pentaerythritol triallyl ether, methylenebisacrylamide, N,N'-divinylethyleneurea, triallylamine and triallylmonoalkylammonium salts, and acrylic esters of glycol, butanediol, trimethylolpropane or glycerol or acrylic esters of glycol, butanediol, trimethylolpropane and glycerol reacted with ethylene oxide and/or epichlorohydrin.

Mixtures of the abovementioned compounds can of course also be used. The component d5) is preferably soluble in the reaction medium. If the solubility of component d5) in the reaction medium is low, then it can be dissolved in a monomer or in a monomer mixture, or else be metered in in dissolved form in a solution which is miscible with the reaction medium. Particular preference is given to those components d5) which are soluble in the monomer mixture.

If the component d5) is used to prepare the polymer A) according to the invention, then the amount used is at least 0.01, preferably at least 0.05, particularly preferably at least 0.1 and at most 5, preferably at most 2 and particularly preferably at most 1% by weight, based on the total amount of the components a) to d).

If the polymers A according to the invention are to comprise a component d5) in copolymerized form, then it is particularly advantageous to use mixtures of components c) and d5). Such mixtures are commercially available and, besides the component c), comprise substances usually referred to as reactive thinners, such as, for example tripropylene glycol diacrylate (TPGDA), hexanediol diacrylate (HDDA), dipropylene glycol diacrylate (DPGDA), trimethyloipropane formal monoacrylate (e.g. Laromer®LR 8887), trimethylolpropane triacrylate (TMPTA), propoxylated glyceryl triacrylate (GPTA), ethoxylated trimethylolpropane triacrylate (EO3TMPTA), ethoxyethoxyethyl acrylate (EOEOEA), PEG 400 diacrylate (PEG400DA), isobornyl acrylate (IBOA), propoxylated neopentyl glycol diacrylate (PO2NPGDA), 2-phenoxyethyl acrylate (POEA), butanediol diacrylate (BDDA), butanediol acrylate (BOMA), dihydrodicyclopentadienyl acrylate (DCPA), triethylene glycol divinyl ether, ethyl diglycol acrylate (EDGA), lauryl acrylate (LA), 4-t-butylcyclohexyl acrylate (TBCH).

As component d) it is also possible to use vinyl acetate, vinyl propionate, vinyl butyrate, ethylene, propylene, isobutylene, butadiene, styrene, α-methylstyrene, acrylonitrile, methacrylonitrile, vinyl chloride, vinylidene chloride, vinyl fluoride, vinylidene fluoride and mixtures thereof.

The components d) can also be silicone-containing compounds, in particular also silicone groups (poly)urethane acrylates.

The polymers A present in the preparations according to the invention preferably comprise
a) 50-95% by weight of component a),
b) 4-30% by weight of component b),
c) 0.1-20% by weight of component c) and
d) 0-30% by weight of component d)
    in copolymerized form, with the proviso that the amounts of components a) to d) add up to 100% by weight.

The polymers A present in the preparations according to the invention particularly preferably comprise
a) 65-85% by weight of component a),
b) 10-30% by weight of component b),
c) 0.5-10% by weight of component c) and
d) 0-30% by weight of component d)
in copolymerized form, with the proviso that the amounts of components a) to d) add up to 100% by weight.

In one embodiment of the invention, the polymers A present in the preparations according to the invention comprise, in copolymerized form
a) 70-80% by weight of component a) chosen from the group consisting of methyl methacrylate, ethyl methacrylate and mixtures thereof,
b) 15-28% by weight of component b) chosen from the group consisting of acrylic acid, methacrylic acid and mixtures thereof,
c) 0.5-5% by weight of urethane-group-containing (meth) acrylates
d) 0-30% by weight of component d),
with the proviso that the amounts of the components a) to d) add up to 100% by weight.

Preparation of the Polymers A According to the Invention

The polymers A according to the invention can be prepared, for example, by solution polymerization, precipitation polymerization, suspension polymerization or emulsion polymerization. Such processes are in principle known to the person skilled in the art. The preparation is preferably by solution polymerization. It is preferred to prepare the polymers A by free-radical solution polymerization.

Preferred solvents for the polymerization are alcoholic or alcoholic/aqueous solvents, such as ethanol and mixtures of ethanol with water and/or further alcohols, such as methanol, n-propanol, ispropanol, n-butanol, sec-butanol, tert-butanol, n-hexanol and cyclohexanol, and glycols, such as ethylene glycol, propylene glycol and butylene glycol, and the methyl or ethyl ethers of the dihydric alcohols such as diethylene glycol, triethylene glycol, polyethylene glycols with number-average molecular weights up to about 3000, glycerol and dioxane.

The polymerization is particularly preferably in alcohol, for example in ethanol or in an alcohol/water mixture, for example in an ethanol/water mixture.

The polymerization temperatures are preferably in a range from about 30 to 120° C., particularly preferably 40 to 100° C. The polymerization usually takes place under atmospheric pressure, although it can also proceed under reduced or increased pressure. A suitable pressure range is between 1 and 5 bar.

For the copolymerization, the monomers can be polymerized with the help of initiators which form free radicals.

Initiators which can be used for the free-radical polymerization are the peroxo and/or azo compounds customary therefor, for example alkali metal or ammonium peroxydisulfates, diacetyl peroxide, dibenzoyl peroxide, succinyl peroxide, di-tert-butyl peroxide, tert-butyl perbenzoate, tert-butyl perpivalate, tert-butyl peroxy-2-ethylhexanoate, tert-butyl permaleate, cumene hydroperoxide, diisopropyl peroxy-dicarbamate, bis(o-toloyl) peroxide, didecanoyl peroxide, dioctanoyl peroxide, dilauroyl peroxide, tert-butyl perisobutyrate, tert-butyl peracetate, di-tert-amyl peroxide, tert-butyl hydroperoxide, azobisisobutyronitrile, 2,2'-azobis(2-amidinopropane)hydrochloride (Wako V-50®), 2,2'-azobis[2-(2-imidazolin-2-yl)propane] (Wako VA-061®), 2,2'-azobis(2-methylbutyronitrile) (Wako V-59®), dimethyl 2,2'-azobis(2-methylpropionate) (Wako V-601®), 2,2'-azobis(2,4-dimethylvaleronitrile), 1,1'-azobis(1-cyclohexanecarbonitrile), 4,4'-azobis(4-cyanovaleric acid) or 2-(carbamoylazo)isobutyronitrile.

Also suitable are initiator mixtures or redox initiator systems, such as, for example, ascorbic acid/iron(II) sulfate/ sodium peroxodisulfate, tert-butyl hydroperoxide/sodium disulfite, tert-butyl hydroperoxide/sodium hydroxymethanesulfinate, $H_2O_2/Cu^I$.

Suitable oxidizing agents for redox initiator systems are essentially the peroxides given above. Corresponding reducing agents which can be used are sulfur compounds with a low oxidation state, such as alkali metal sulfites, for example potassium and/or sodium sulfite, alkali metal hydrogensulfites, for example potassium and/or sodium hydrogensulfite, alkali metal metabisulfites, for example potassium and/or sodium metabisulfite, formaldehyde sulfoxylates, for example potassium and/or sodium formaldehyde sulfoxylate, alkali metal salts, specifically potassium and/or sodium salts of aliphatic sulfinic acids and alkali metal hydrogensulfides, such as, for example, potassium and/or sodium hydrogensulfide, salts of polyvalent metals, such as iron(II) sulfate, iron (II) ammonium sulfate, iron(II) phosphate, enediols, such as dihydroxy-maleic acid, benzoin and/or ascorbic acid, and reducing saccharides, such as sorbose, glucose, fructose and/ or dihydroxyacetone.

Suitable initiators are described in chapters 20 and 21 of Macromolecules, Vol. 2, 2nd Ed., H. G. Elias, Plenum Press, 1984, New York, which is hereby incorporated in its entirety by reference. Furthermore, suitable photoinitiators are described in S. P. Pappas, J. Rad. Cur., July 1987, p. 6, which is hereby incorporated in its entirety by reference.

The initiators are usually used in amounts up to 10, preferably 0.02 to 5, % by weight, based on the monomers to be polymerized.

To adjust the molecular weight, the polymerization can be carried out in the presence of at least one chain transfer reagent (regulator). Chain transfer reagents which can be used are the customary compounds known to the person skilled in the art, such as, for example, sulfur compounds, e.g. mercaptoethanol, 2-ethylhexyl thioglycolate, thioglycolic acid, alkanethiols, and tribromochloromethane or other compounds which have a regulating effect on the molecular weight of the polymers obtained.

The alkanethiols used are linear and branched alkanethiols with a carbon chain length of from $C_{10}$ to $C_{22}$. Particular preference is given to linear alkanethiols, and further preference is given to alkanethiols with a chain length of from $C_{12}$ to $C_{22}$, in particular from $C_{12}$ to $C_{18}$. Preferred alkanethiols which may be mentioned are n-decanethiol, n-dodecanethiol, tert-dodecanethiol, n-tetradecanethiol, n-pentadecanethiol, n-hexadecanethiol, n-heptadecanethiol, n-octadecanethiol, n-nonadecanethiol, n-eicosanethiol, n-docosanethiol. Particular preference is given to linear, even-numbered alkanethiols. The alkanethiols can also be used in mixtures.

The alkanethiols are usually used in amounts of from 0.1 to 5% by weight, in particular 0.25 to 2% by weight, based on the monomers to be polymerized. Usually, the alkanethiols are added to the polymerization together with the monomers.

If, in the polymerization, alkanethiols with a carbon chain length of from $C_{10}$ to $C_{13}$ are used, subsequent hydrogen peroxide treatment is required in order to obtain polymers with a neutral odor. For this hydrogen peroxide treatment which follows the polymerization, use is usually made of 0.01 to 2.0% by weight, in particular 0.02 to 1.0% by weight, preferably 0.3 to 0.8% by weight, further preferably 0.03 to 0.15% by weight, of hydrogen peroxide, based on the monomers to be polymerized. It has proven to be advantageous to carry out the hydrogen peroxide treatment at a temperature of from 20 to 100° C., in particular from 30 to 80° C. The hydrogen peroxide treatment is usually carried out for a period of from 30 min to 240 min, in particular for a period of from 45 min to 90 min.

If alkanethiols with a carbon chain length of from C14 to C22 are used, the hydrogen peroxide treatment can be dispensed with. In a further embodiment of the invention, however, a hydrogen peroxide treatment can be added even when using alkanethiols with a chain length of from C14 to C22.

To achieve the purest possible polymers A with a low residual monomer content, the polymerization (main polymerization) can be followed by at least one after-polymerization step. The after-polymerization can take place in the presence of the same initiator system as the main polymerization, or a different initiator system. Preferably, the after-polymerization takes place at least at the same temperature as the main polymerization, preferably at a higher temperature. If desired, following the polymerization or between the first and the second polymerization step, the reaction mixture can be subjected to stripping with water vapor or to a water vapor distillation.

The copolymerization takes place in accordance with the customary processing techniques of solution polymerization, e.g. according to the so-called batch polymerization, in which the monomers and, if appropriate, polymerization regulators and initiator are initially introduced in a solvent and heated to the polymerization temperature. The reaction mixture is preferably stirred at the polymerization temperature until the conversion of the monomers is more than 99.9%. In these processes, the initiators can, if appropriate, also be added once the polymerization temperature has been reached.

Further process barriers are feed methods, which are preferably used. In these, individual reaction participants or all of the reaction participants are added, completely or partially, in batches or continuously, together or in separate feeds, to a reaction mixture. Thus, for example, it is possible, for example, if appropriate to add a solution of the polymerization regulator and an initiator solution continuously or batchwise to a mixture of the monomers and of a solvent at the polymerization temperature within a given time. It is also possible to meter a mixture of initiator and, if appropriate, regulator into the initial charge heated to polymerization temperature. Another variant consists in adding the initiator to the initial charge below or at the polymerization temperature and, if a regulator is to be used, to only add the regulator or a solution of the regulator to the reaction mixture within a pregiven time after the polymerization temperature has been reached.

The organic solvent used in the preparation of the polymers can be removed by customary methods known to the person skilled in the art, e.g. by distillation at reduced pressure. The mixtures which form during the polymerization can be subjected to a physical or chemical after-treatment following the polymerization process. Such processes are, for example, the known processes for reducing residual monomers, such as, for example, after-treatment by adding polymerization initiators or mixtures of two or more polymerization initiators at suitable temperatures or heating the polymerization solution to temperatures above the polymerization temperature, after-treatment of the polymer solution by means of water vapor or stripping with nitrogen or treating the reaction mixture with oxidizing or reducing reagents, adsorption processes such as the adsorption of contamination onto selected media such as, for example, activated carbon, or ultrafiltration. The known work-up steps can also follow, for example suitable drying processes such as spray-drying, freeze-drying or drum-drying, or agglomeration processes following drying. The mixtures with a low residual monomer content obtained by the process according to the invention can also be sold directly.

Pulverulent polymers have the disadvantage of better storage properties, easier transportation and generally have a lower tendency for microbial attack.

Neutralization

The polymers A according to the invention can be partially or completely neutralized. Particularly for using the polymers in hair cosmetic preparations, partial or complete neutralization is advantageous. In preferred embodiments, the polymers are neutralized, for example, to at least 10%, preferably to at least 30%, further preferably to at least 40%, particularly preferably to at least 50%, very particularly preferably to at least 70% and in particular to at least 90 to 100%. It may also be advantageous to neutralize the polymers to at least 99% and in particular to at least 100%.

The neutralization can take place during or after the polymerization.

It is also advantageous if the neutralizing agent is added in a more than equivalent amount, equivalent amount being understood as meaning the amount which is required in order to neutralize all of the neutralizable groups of the polymers.

The neutralization can be carried out, for example, with
- a mono-, di- or trialkanolamine having 2 to 5 carbon atoms in the alkanol radical, which is present, if appropriate, in etherified form, for example mono-, di- and triethanolamine, mono-, di and tri-n-propanolamine, mono-, di- and triisopropanolamine, 2-amino-2-methylpropanol and di(2-methoxyethyl)amine,
- an alkanediolamine having 2 to 5 carbon atoms, for example 2-amino-2-methylpropane-1,3-diol and 2-amino-2-ethylpropane-1,3-diol, or
- a primary, secondary or tertiary alkylamine having in total 5 to 10 carbon atoms, for example N,N-diethylpropylamine or 3-diethylamino-1-propylamine.

Suitable alkali metal hydroxides for the neutralization are primarily sodium hydroxide, or potassium hydroxide and ammonium hydroxide. The preferred alkali metal hydroxide is potassium hydroxide.

Good neutralization results are often obtained with 2-amino-2-methylpropanol, triisopropanolamine, 2-amino-2-ethylpropane-1,3-diol, N,N-dimethylaminoethanol or 3-diethylamino-1-propylamine.

For neutralizing the polymers in the preparations and compositions according to the invention, silicone polymers comprising amino groups in particular are suitable, Suitable silicone polymers comprising amino groups are, for example, the silicone-aminopolyalkylene oxide block copolymers of WO 97/32917, the products Silsoft®A-843 (dimethicone bisamino hydroxypropyl copolyol) and Silsoft®A-858 (trimethylsilyl amodimethicone copolymer) (both Witco). In addition, the neutralization polymers of EP-A 1 035 144 and in particular the silicone-containing neutralization polymers according to claim 12 of EP-A 1 035 144 are also suitable.

Hair Cosmetic Preparations

The polymers A described above are exceptionally suitable for producing hair cosmetic preparations, in particular as low-VOC preparations. They serve here, for example, as polymeric film formers. They can be used and formulated universally into a very wide variety of hair cosmetic preparations and are compatible with the customary components.

The term VOC is known to the person skilled in the art. VOC (volatile organic compounds) are organic chemical compounds which boil at atmospheric pressure in a range up to about 260° C. and can thus enter the atmosphere in gaseous form. Volatile organic compounds include numerous solvents and propellants.

| Classification of organic compounds in interiors (according to: WHO—World Health Organization 1989) | | |
|---|---|---|
| Compounds | Abbreviation | Boiling point range [° Celsius] |
| Very volatile organic compounds | VVOC | <0 to 50° C. (up to 100° C.) |
| Volatile organic compounds | VOC | 50 to 250° C. (100 to 260° C.) |
| Semi volatile organic compounds) | SVOC | 250 to 380° C. (260 to 400° C.) |

The polymers A are advantageously suitable for producing elastic hairstyles coupled with strong setting (even at high atmospheric humidity). The polymers A according to the invention are characterized by good propellant gas compatibility, good solubility in aqueous/alcoholic solvent mixtures, in particular by suitability for use as optically clear low-VOC formulations and by good ability to be washed out. In addition, they generally also have good conditioning properties, i.e. they improve hair treated with them in its sensorially perceptible properties, such as feel, volume, handlability, etc. Hairspray formulations based on the polymers A according to the invention are characterized by good sprayability and good rheological properties and exceptionally low stickiness of the resulting films. The hair cosmetic preparations according to the invention comprising the polymers A do not have a tendency to form foam following application. Besides the good compatibility with the customary hair cosmetic ingredients, the applied polymers A dry quickly.

Cosmetically Acceptable Carrier B)

The aqueous preparations according to the invention also have at least one cosmetically acceptable carrier B) which is chosen from
i) water-miscible organic solvents, preferably $C_2$-$C_4$-alkanols, in particular ethanol,
ii) oils, fats, waxes,
iii) esters of $C_6$-$C_{30}$-monocarboxylic acids with mono-, di- or trihydric alcohols which are different from iii),
iv) saturated acyclic and cyclic hydrocarbons,
v) fatty acids,
vi) fatty alcohols,
vii) propellants (propellant gases) and
viii) mixtures thereof.

Suitable carriers B and further active ingredients and additives to be used advantageously are described in detail below.

Suitable cosmetically and pharmaceutically compatible oil and fat components B) are described in Karl-Heinz Schrader, Grundlagen and Rezepturen der Kosmetika, [Fundamentals and formulations of cosmetics], 2nd Edition, Verlag Hüthig, Heidelberg, pp. 319-355, which is hereby incorporated by reference. The preparations according to the invention can, for example, have an oil or fat component B) which is chosen from: hydrocarbons of low polarity, such as mineral oils; linear saturated hydrocarbons, preferably having more than 8 carbon atoms, such as tetradecane, hexadecane, octadecane, etc.; cyclic hydrocarbons, such as decahydronaphthalene; branched hydrocarbon; animal and vegetable oils; waxes; wax esters; vaseline; esters, preferably esters of fatty acids, such as, for example, the esters of $C_1$-$C_{24}$-monoalcohols with $C_1$-$C_{22}$-monocarboxylic acids, such as isopropyl isostearate, n-propyl myristate, isopropyl myristate, n-propyl palmitate, isopropyl palmitate, hexacosanyl palmitate, octacosanyl palmitate, triacontanyl palmitate, dotriacontanyl palmitate, tetratriacontanyl palmitate, hexacosanyl stearate, octacosanyl stearate, triacontanyl stearate, dotriacontanyl stearate, tetratriacontanyl stearate; salicylates, such as $C_1$-$C_{10}$-salicylates, e.g. octyl salicylate, benzoate esters, such as $C_{10}$-$C_{15}$-alkyl benzoates, benzyl benzoate; other cosmetic esters, such as fatty acid triglycerides, propylene glycol monolaurate, polyethylene glycol monolaurate, $C_{10}$-$C_{15}$-alkyl lactates, etc. and mixtures thereof.

Suitable silicone oils B) are, for example, linear polydimethylsiloxanes, poly(methylphenylsiloxanes), cyclic siloxanes and mixtures thereof. The number-average molecular weight of the polydimethylsiloxanes and poly(methylphenylsiloxanes) is preferably in a range from about 1000 to 150 000 g/mol. Preferred cyclic siloxanes have 4- to 8-membered rings. Suitable cyclic siloxanes are commercially available, for example, under the name cyclomethicone.

Preferred oil and fat components B) are chosen from paraffin and paraffin oils; vaseline; natural fats and oils, such as castor oil, soybean oil, peanut oil, olive oil, sunflower oil, sesame oil, avocado oil, cocoa butter, almond oil, persic oil, ricinus oil, cod liver oil, lard, spermaceti, spermaceti oil, sperm oil, wheatgerm oil, macadamia nut oil, evening primrose oil, jojoba oil; fatty alcohols, such as lauryl alcohol, myristyl alcohol, cetyl alcohol, stearyl alcohol, oleyl alcohol, cetyl alcohol; fatty acids, such as myristic acid, stearic acid, palmitic acid, oleic acid, linoleic acid, linolenic acid and saturated, unsaturated and substituted fatty acids different therefrom; waxes, such as beeswax, carnauba wax, candelilla wax, spermaceti and mixtures of the abovementioned oil and fat components.

Suitable hydrophilic carriers B) are chosen from water, 1-, 2- or polyhydric alcohols having preferably 1 to 8 carbon atoms, such as ethanol, n-propanol, isopropanol, propylene glycol, glycerol, sorbitol, etc.

Preferably, the preparations according to the invention which comprise the polymers A are in the form of a spray, gel, foam, ointment, cream, emulsion, suspension, lotion, milk or paste. If desired, liposomes or microspheres can also be used.

The preparations according to the invention preferably have a pH of from 2.0 to 9.3. The pH range is particularly preferably between 4 and 8. Organic solvents or a mixture of solvents with a boiling point below 400° C. may be present as additional cosolvents in an amount of from 0.1 to 15% by weight, preferably from 1 to 10% by weight. Particularly suitable additional cosolvents are unbranched or branched hydrocarbons, such as pentane, hexane, isopentane and cyclic hydrocarbons, such as cyclopentane and cyclohexane. Further particularly preferred water-soluble solvents are glycerol, ethylene glycol and propylene glycol in an amount up to 30% by weight.

In a preferred embodiment of the invention, the preparations according to the invention have a fraction of volatile organic components of at most 80% by weight, preferably at most 55% by weight and in particular at most 35% by weight. A preferred subject-matter are thus hair cosmetic preparations which correspond to the low-VOC standard, i.e. VOC-80 or VOC-55 standard.

Preference is given to the use of the polymers A in particular in hairspray preparations which comprise the following constituents:
partially or completely neutralized polymer A;
water;
cosmetically customary organic solvent such as, for example, ethanol, isopropanol and dimethoxymethane, in addition also acetone, n-propanol, n-butanol, 2-methoxypropan-1-ol, n-pentane, n-hexane, cyclohexane, n-heptane, n-octane or dichloromethane or mixtures thereof;

cosmetically customary propellant such as, for example, n-propane, isopropane, n-butane, isobutane, 2,2-dimethylbutane, n-pentane, isopentane, dimethyl ether, difluoroethane, fluorotrichloromethane, dichlorodifluoromethane or dichlorotetrafluoroethane, HFC-152 A (1,1-difluoroethane), HFC-134a (1,1,2,2-tetrafluoroethane), $N_2$, $N_2O$ and CO or mixtures thereof.

To neutralize the polymers A according to the invention and hence the component b) and to adjust the pH of the hair cosmetic preparations, alkanolamines are advantageously used. Examples (INCI) are aminomethylpropanol, diethanolamine, diisopropanolamine, ethanolamine, methylethanolamine, N-lauryldiethanolamine, triethanolamine, triisopropanolamine, etc. It is possible to use alkanolamines carrying either primary amino groups or secondary amino groups.

Furthermore, alkali metal hydroxides (e.g. NaOH, preferably KOH) and other bases can be used for the neutralization (e.g. histidine, arginine, lysine or ethylenediamines, diethylenetriamine, melamine, benzoguanamine). All of the bases given can be used on their own or as a mixture with other bases for the neutralization of acid-containing cosmetic products.

Accordingly, the present invention provides aqueous hair cosmetic preparations which, besides the at least one polymer A and the carrier B, also comprises at least one active ingredient or additive chosen from the group consisting of viscosity-modifying substances, haircare substances, hair-setting substances, silicone compounds, photoprotective substances, fats, oils, waxes, preservatives, pigments, soluble dyes, particulate substances, and surfactants.

Propellants (Propellant Gases)

Of the specified compounds, the propellants (propellant gases) used are primarily the hydrocarbons, in particular propane, n-butane, n-pentane and mixtures thereof, and also dimethyl ether and difluoroethane. If appropriate, one or more of the specified chlorinated hydrocarbons are co-used in propellant mixtures, but only in small amounts, for example up to 20% by weight, based on the propellant mixture.

The hair cosmetic preparations according to the invention are also particularly suitable for pump spray preparations without the addition of propellants or else for aerosol sprays with customary compressed gases, such as nitrogen, compressed air or carbon dioxide as propellant.

A hydrous standard aerosol spray formulation has, for example, the following composition:
polymer neutralized to 100% with 2-amino-2-methylpropanol
ethanol
water
dimethyl ether and/or propane/n-butane and/or propane/isobutane.

Here, the total amount of volatile organic components is preferably at most 80% by weight, particularly preferably at most 55% by weight, of the preparation.

Preferably, the hair cosmetic preparations according to the invention comprise at least one polymer A, at least one cosmetically acceptable carrier B) as defined above and at least one further active ingredient or additive different therefrom which is chosen from cosmetically active ingredients, emulsifiers, surfactants, preservatives, perfume oils, thickeners, hair polymers, hair conditioners, graft polymers, water-soluble or dispersible silicone-containing polymers, photoprotective agents, bleaches, gel formers, care agents, colorants, tints, tanning agents, dyes, pigments, consistency regulators, humectants, refitting agents, collagen, protein hydrolysates, lipids, antioxidants, antifoams, antistats, emollients, lanolin components, protein hydrolysates and softeners.

Further Polymers

To adjust the properties of hair cosmetic preparations in a targeted manner, it may be advantageous to use the polymers according to the invention in mixture with further (hair) cosmetically customary polymers.

In a further preferred embodiment, the composition according to the invention comprises 0.01 to 15% by weight, preferably 0.5 to 10% by weight, of at least one synthetic or natural nonionic, preferably a film-forming polymer. Natural polymers are also understood as meaning chemically modified polymers of natural origin. Film-forming polymers are understood as meaning those polymers which, when applied in 0.01 to 5% strength aqueous, alcoholic or aqueous-alcoholic solution, are able to deposit a polymer film on the hair.

Suitable such further customary polymers for this are, for example, anionic, cationic, amphoteric, zwitterionic and neutral polymers.

Examples of such further polymers are
copolymers of ethyl acrylate and methacrylic acid
copolymers of N-tert-butylacrylamide, ethyl acrylate and acrylic acid,
polyvinylpyrrolidones
polyvinylcaprolactams
polyurethanes
copolymers of acrylic acid, methyl methacrylate, octylacrylamide, butylaminoethyl methylacrylate and hydroxypropyl methacrylate,
copolymers of vinyl acetate and crotonic acid and/or (vinyl)neodecanoate,
copolymers of vinyl acetate and/or vinyl propionate and N-vinylpyrrolidone,
carboxy-functional copolymers of vinylpyrrolidone, t-butyl acrylate, methacrylic acid,
copolymers of tert-butyl acrylate, methacrylic acid and dimethicone copolyol.

Surprisingly, it has been found that hair cosmetic preparations which comprise the polymers A in combination with further polymers have unexpected properties. The hair cosmetic preparations according to the invention are superior to the preparations from the prior art especially with regard to the totality of their hair cosmetic properties.

Copolymers of ethyl acrylate and methacrylic acid (INCI name: Acrylates Copolymer) are available, for example, as commercial products Luviflex®Soft (BASF).

Copolymers of N-tert-butylacrylamide, ethyl acrylate and acrylic acid (INCI name: acrylates/acrylamide copolymer) are available, for example, as commercial products Ultrahold Strong®, Ultrahold 8® (BASF).

Polyvinylpyrrolidones (INCI name: PVP) are available, for example, under the trade names Luviskol®K, Luviskol®K30 (BASF) and PVP K® (ISP).

Polyvinylcaprolactams (INCI: polyvinylcaprolactams) are available, for example, under the trade name Luviskol Plus® (BASF).

Polyurethanes (INCI: Polyurethane-1) are available, for example, under the trade name Luviset®PUR.

Copolymers of acrylic acid, methyl methacrylate, octylacrylamide, butylaminoethyl methylacrylate, hydroxypropyl methacrylate (INCI: Octylacrylamide/Acrylates/Butylaminoethyl Methacrylate Copolymer) are known, for example, under the trade names Amphomer®28-4910 and Amphomer®LV-71 (National Starch).

Copolymers of vinyl acetate and crotonic acid (INCI: VA/Crotonate/Copolymer) are available, for example, under the trade names Luviset®CA 66 (BASF), Resyn®28-1310 (National Starch), Gafset® (GAF) or Aristoflex®A (Celanese).

Copolymers of vinyl acetate, crotonic acid and (vinyl) neodecanoate (INCI: VA/Crotonates/Neodecanoate Copolymer) are available, for example, under the trade names Resyn®28-2930 (National Starch) and Luviset®CAN (BASF).

Copolymers of vinyl acetate and N-vinylpyrrolidone (INCI: PVPNA) are available, for example, under the trade names Luviskol VA® (BASF) and PVPNA (ISP).

Carboxyfunctional copolymers of vinylpyrrolidone, t-butyl acrylate, methacrylic acid are available, for example, under the trade name Luviskol®VBM (BASF).

Copolymers of tert-butyl acrylate, methacrylic acid and dimethicone copolyol are available, for example, under the trade name Luviflex®Silk (BASF).

Suitable anionic polymers are homopolymers and copolymers of acrylic acid and methacrylic acid or salts thereof which are different from the polymers A, copolymers of acrylic acid and acrylamide and salts thereof, sodium salts of polyhydroxycarboxylic acids, copolymers of acrylic acid and methacrylic acid with, for example, hydrophobic monomers, e.g. $C_4$-$C_{30}$-alkyl esters of (meth)acrylic acid, $C_4$-$C_{30}$-alkylvinyl esters, $C_4$-$C_{30}$-alkyl vinyl ethers and hyaluronic acid and also further polymers known under the trade names Amerhold®DR-25, Ultrahold®, Luviset®P.U.R., Acronal®, Acudyne®, Lovocryl®, Versatyl®, Amphomer® (28-4910, LV-71), Placise®L53, Gantrez®ES 425, Advantage Plus®, Omnirez®2000, Resyn®28-1310, Resyn 28-2930, Balance®(0/55), Acudyne®255, Aristoflex®A or Eastman AQ®.

In addition, the group of suitable polymers comprises, for example, Balance®CR (National Starch), Balance®47 (National Starch; octylacrylamide/acrylates/butylaminoethyl methacrylates copolymer), Aquaflex®FX 64 (ISP; isobutylene/ethylmaleimide/hydroxyethylmaleimide copolymer), Aquaflex®SF-40 (ISP/National Starch; VP/vinyl caprolactam/DMAPA acrylates copolymer), Allianz®LT-120 (ISP/Rohm & Haas; acrylate/C1-2 succinate/hydroxyacrylate copolymer), Aquarez® HS (Eastman; Polyester-1).

Also suitable are the polymers under the trade names Diaformer®Z-400 (Clariant; methacryloylethylbetaine/methacrylate copolymer), Diaformer®Z-711 (Clariant; methacryloylethyl N-oxide/methacrylate copolymer), Diaformer®Z-712 (Clariant; methacryloylethyl N-oxide/methacrylate copolymer), Omnirez®2000 (ISP; monoethyl ester of poly(methyl vinyl ether/maleic acid in ethanol), Amphomer®HC (National Starch; acrylate/octylacrylamide copolymer), Amphomer®28-4910 (National Starch; octylacrylamide/acrylate/butylaminoethyl methacrylate copolymer), Advantage®HC 37 (ISP; terpolymer of vinylcaprolactam/vinylpyrrolidone/dimethylaminoethyl methacrylate), Advantage®LC55 and LC80 or LC A and LC E, Advantage Plus (ISP; VA/butyl maleate/isobornyl acrylate copolymer), Aculyne®258 (Rohm & Haas; acrylate/hydroxy ester acrylate copolymer), Luviset®P.U.R. (BASF, Polyurethane-1), Eastman®AQ 48 (Eastman), Styleze®CC-10 (ISP; VP/DMAPA acrylates copolymer), Styleze® 2000 (ISP; VP/acrylatesflaurylmethacrylate copolymer), DynamX® (National Starch; polyurethane-14 AMP acrylates copolymer), Resyn®XP (National Starch; acrylates/octylacrylamide copolymer), Fixomer® A-30 (Ondeo Nalco; polymethacrylic acid (and) acrylamidomethylpropanesulfonic acid), Fixate® G-100 (Noveon; AMP acrylates/allyl methacrylate copolymer).

Suitable polymers are also copolymers of (meth)acrylic acid and polyether acrylates, where the polyether chain is terminated with a $C_8$-$C_{30}$-alkyl radical. These include, for example, acrylate/beheneth-25 methacrylate copolymers, which are available under the name Aculyn® (Rohm+Haas). Particularly suitable polymers are also copolymers of t-butyl acrylate, ethyl acrylate, methacrylic acid (e.g. Luvimer®100P, Luvimer®Pro55) and copolymers of ethyl acrylate and methacrylic acid (e.g. Luvimer®MAE).

Also suitable are crosslinked polymers of acrylic acid, as are available under the INCI name Carbomer. Such crosslinked homopolymers of acyrlic acid are commercially available, for example, as Carbopol® (Noveon). Preference is also given to hydrophobically modified crosslinked polyacrylate polymers, such as Carbopol®Ultrez 21 (Noveon). Such further polymers can also be used for modifying the rheology of the preparations, i.e. as thickeners.

Further suitable additional polymers are water-soluble or water-dispersible polyesters, polyureas, polyurethanes, polyurethaneureas, maleic anhydride copolymers reacted, if appropriate, with alcohols, or anionic polysiloxanes.

In addition, polymers suitable for use together with the polymers A are, for example, also cationic and cationogenic polymers. These include, for example, copolymers of N-vinylpyrrolidone/N-vinylimidazolium salts (available, for example, under the trade names Luviquat®FC, Luviquat®HM, Luviquat®MS, Luviquat®Care, Luviquat® UltraCare (BASF), copolymers of N-vinylcaprolactam/N-vinylpyrrolidone/N-vinylimidazolium salts (available, for example, under the trade name Luviquat®Hold), copolymers of N-vinylpyrrolidone/dimethylaminoethyl methacrylate, quaternized with diethyl sulfate (available, for example, under the trade name Luviquat®PQ11), cationic cellulose derivatives (polyquaternium-4 and -10), acrylamide copolymers (polyquaternium-7), guar hydroxypropyltrimethylammonium chloride (INCI: Hydroxypropyl Guar Hydroxypropyltrimonium Chloride), polyethyleneimines and salts thereof, polyvinylamines and salts thereof, polymers based on dimethyldiallylammonium chloride (Merquat®), polymers which are formed by reacting polyvinylpyrrolidone with quaternary ammonium compounds (Gafquat®), hydroxyethylcellulose with cationic groups (Polymer®JR) and cationic plant-based polymers, e.g. guar polymers, such as the Jaguar® grades (Rhodia).

Suitable as further hair cosmetic polymers are also neutral polymers, such as polyvinylpyrrolidones, copolymers of N-vinylpyrrolidone and vinyl acetate and/or vinyl propionate, polysiloxanes, polyvinylcaprolactams and copolymers with N-vinylpyrrolidone, cellulose derivatives, polyaspartic acid salts and derivatives, polyamides, e.g. based on itaconic acid and aliphatic diamines, as described in DE-A-43 33 238.

The abovementioned types of polymer include those known under the trade names Luviskol® (K, VA, Plus), PVP K, PVPNA, Advantage®HC, Luviflex®Swing, Kollicoat®IR, $H_2$OLD®EP-1.

Furthermore, suitable further polymers are also biopolymers, i.e. polymers which are obtained from naturally renewable raw materials and are constructed from natural monomer building blocks, e.g. cellulose derivatives, chitin, chitosan, DNA, hyaluronic acid and RNA derivatives.

Suitable mixing partners for the polymers according to the invention are also zwitterionic polymers, as are disclosed, for example, in the German patent applications DE 39 29 973, DE 21 50 557, DE 28 17 369 and DE 37 08 451, and methacroylethylbetaine/methacrylate copolymers which are commercially available under the name Amersette® (Amerchol), or copolymers of hydroxyethyl methacrylate, methyl methacrylate, N,N-dimethylaminoethyl methacrylate and acrylic acid (Jordapon®).

Further suitable polymers are also betainic polymers, such as Yukaformers (R205, SM) and Diaformers.

Polymers suitable as mixing partners are also nonionic, siloxane-containing, water-soluble or -dispersible polymers, e.g. polyether siloxanes, such as Tegopren® (Goldschmidt) or Belsil® (Wacker).

Cosmetically and/or Dermatologically Active Ingredients

Suitable cosmetically and/or dermatologically active ingredients are, for example, coloring active ingredients, skin and hair pigmentation agents, tints, tanning agents, bleaches, keratin-hardening substances, antimicrobial active ingredients, photo filter active ingredients, repellant active ingredients, hyperemic substances, keratolytic and keratoplastic substances, antidandruff active ingredients, antiphlogistics, keratinizing substances, antioxidative active ingredients or active ingredients which act as free-radical scavengers, substances which moisten the skin or keep the skin moist, refatting active ingredients, antierythimatous or antiallergic active ingredients and mixtures thereof.

Preferred hair cosmetic care and active ingredients are ARA acids, fruit acids, ceramides, phytantriol, collagen, vitamins and provitamins, for example vitamin A, E and C, retinol, bisabolol and panthenol. A particularly preferred hair cosmetic care substance in the preparations according to the invention is panthenol, which is commercially available, for example, as D-Panthenol®USP, D-Panthenol®50 P, D-Panthenol®75 W, D,L-Panthenol 50 W.

Artificially skin-tanning active ingredients which are suitable for tanning the skin without natural or artificial irradiation with UV rays are, for example, dihydroxyacetone, alloxan and walnut shell extract.

Suitable keratin-hardening substances are generally active ingredients as are also used in antiperspirants, such as, for example, potassium aluminum sulfate, aluminum hydroxychloride, aluminum lactate, etc.

Antimicrobial active ingredients are used to destroy microorganisms or to inhibit their growth and thus serve both as preservatives and also as deodorizing substance which reduces the formation or the intensity of body odor. These include, for example, customary preservatives known to the person skilled in the art, such as p-hydroxy-benzoic esters, imidazolidinylurea, formaldehyde, sorbic acid, benzoic acid, salicylic acid, etc. Such deodorizing substances are, for example, zinc ricinoleate, triclosan, undecylenic acid alkylolamides, triethyl citrate, chlorhexidine, etc. The preparations according to the invention comprise preferably 0.01 to 5% by weight, particularly preferably 0.05 to 1% by weight, of at least one preservative. Suitable further preservatives are the substances listed in the International Cosmetic Ingredient Dictionary and Handbook, 9th Edition with the function "Preservatives", e.g. phenoxyethanol, benzyl paraben, butyl paraben, ethyl paraben, isobutyl paraben, isopropyl paraben, methyl paraben, propyl paraben, iodopropynyl butylcarbamate, methyldibromoglutaronitrile, DMDM hydantoin.

UV Filter Substances

In one embodiment, the preparations according to the invention can comprise oil-soluble and/or water-soluble UVA and/or UVB filters.

The total amount of the filter substances is preferably 0.01 to 10% by weight or from 0.1 to 5% by weight, particularly preferably from 0.2 to 2% by weight, based on the total weight of the preparations.

The majority of the photoprotective agents in the preparations serving to protect the human epidermis consists of compounds which absorb UV light in the UV-B region. For example, the fraction of UV-A absorbers to be used according to the invention is 10 to 90% by weight, preferably 20 to 50% by weight, based on the total amount of UV-B and UV-A absorbing substances.

The UVB filters may be oil-soluble or water-soluble. Advantageous UVB filter substances are, for example:
i) benzimidazolsulfonic acid derivatives, such as, for example, 2-phenylbenzimidazol-5-sulfonic acid and salts thereof
ii) benzotriazole derivatives, such as, for example, 2,2'-methylenebis(6-(2H-benzotriazol-2-yl)-4-(1,1,3,3-tetramethylbutyl)phenol)
iii) 4-aminobenzoic acid derivatives, preferably 2-ethylhexyl 4-(dimethylamino)benzoate, amyl 4-(dimethylamino)benzoate;
iv) esters of benzalmalonic acid, preferably di(2-ethylhexyl) 4-methoxybenzalmalonate;
v) esters of cinnamic acid, preferably 2-ethylhexyl 4-methoxycinnamate, isopentyl 4-methoxycinnamate;
vi) derivatives of benzophenone, preferably 2-hydroxy-4-methoxybenzophenone, 2-hydroxy-4-methoxy-4'-methyl benzophenone, 2,2'-dihydroxy-4-methoxybenzophenone;
vii) methylidenecamphor derivatives, preferably 4-methylbenzylidenecamphor, benzylidenecamphor;
viii) triazine derivatives, preferably tris(2-ethylhexyl) 4,4',4"-(1,3,5-triazine-2,4,6-triyilmino)trisbenzoate [INCI: Diethylhexyl Butamido Triazine, UVA-Sorb® HEB (Sigma 3V)] and 2,4,6-tris[anilino(p-carbo-2'-ethyl-1'-hexyloxy)]-1,3,5-triazine [INCI: Octyl Triazone, Uvinul®150 (BASF)].

Water-soluble UVB filter substances to be used advantageously are, for example, sulfonic acid derivatives of 3-benzylidenecamphor, such as, for example, 4-(2-oxo-3-bornylidenemethyl)benzenesulfonic acid, 2-methyl-5-(2-oxo-3-bornylidenemethyl)sulfonic acid and salts thereof.

UVA filters to be used advantageously are, for example:
1,4-phenylenedimethinecamphorsulfonic acid derivatives, such as, for example, 3,3'-(1,4-phenylenedimethine)bis (7,7-dimethyl-2-oxobicyclo[2.2.1]heptane-1-methanesulfonic acid and its salts
1,3,5-triazine derivatives, such as 2,4-bis{[(2-ethylhexyloxy)-2-hydroxy)phenyl}-6-(4-methoxyphenyl)-1,3,5)-triazine (e.g. Tinosorb®S (Ciba))
dibenzoylmethane derivatives, preferably 4-isopropyldibenzoylmethane, 4-(tert-butyl)-4'-methoxydibenzoylmethane
benzoxazole derivatives, for example 2,4-bis[4-[5-(1,1-dimethylpropyl)benzoxazol-2-yl]phenylimino]-6-[(2-ethylexyl)imino]-1,3,5-triazine (CAS No. 288254-16-0, Uvasorb®K2A (3V Sigma))
hydroxybenzophenones, for example hexyl 2-(4'-diethylamino-2'-hydroxybenzoyl)benzoate (also: aminobenzophenone) (Uvinul®A Plus (BASF))

In addition, it may, if appropriate, be advantageous according to the invention to provide preparations with further UVA and/or UVB filters, for example certain salicylic acid derivatives, such as 4-isopropylbenzyl salicylate, 2-ethylhexyl salicylate, octyl salicylate, homomenthyl salicylate. The total amount of salicylic acid derivatives in the cosmetic preparations is advantageously chosen from the range from 0.1-15.0% by weight, preferably 0.3-10.0% by weight, based on the total weight of the preparations. A further photoprotective filter to be used advantageously according to the invention is ethylhexyl 2-cyano-3,3-diphenylacrylate (octocrylene, Uvinul®N 539 (BASF)).

The table below lists by way of example some of the photoprotective filters suitable for use in the preparations according to the invention:

| No. | Substance | CAS No. |
|---|---|---|
| 1 | 4-Aminobenzoic acid | 150-13-0 |
| 2 | 3-(4'-Trimethylammonium)benzylidenebornan-2-one methyl sulfate | 52793-97-2 |
| 3 | 3,3,5-Trimethylcyclohexyl salicylate (homosalate) | 118-56-9 |
| 4 | 2-Hydroxy-4-methoxybenzophenone (oxybenzone) | 131-57-7 |
| 5 | 2-Phenylbenzimidazole-5-sulfonic acid and its potassium, sodium and triethanolamine salts | 27503-81-7 |
| 6 | 3,3'-(1,4-Phenylenedimethine)bis(7,7-dimethyl-2-oxobicyclo[2.2.1]heptane-1-methanesulfonic acid) and its salts | 90457-82-2 |
| 7 | Polyethoxyethyl 4-bis(polyethoxy)aminobenzoate | 113010-52-9 |
| 8 | 2-Ethylhexyl 4-dimethylaminobenzoate | 21245-02-3 |
| 9 | 2-Ethylhexyl salicylate | 118-60-5 |
| 10 | 2-Isoamyl 4-methoxycinnamate | 71617-10-2 |
| 11 | 2-Ethylhexyl 4-methoxycinnamate | 5466-77-3 |
| 12 | 2-Hydroxy-4-methoxybenzophenone-5-sulfonic acid (sulisobenzone) and the sodium salt | 4065-45-6 |
| 13 | 3-(4'-sulfobenzylidene)bornan-2-one and salts | 58030-58-6 |
| 14 | 3-Benzylidenebornan-2-one | 16087-24-8 |
| 15 | 1-(4'-Isopropylphenyl)-3-phenylpropane-1,3-dione | 63260-25-9 |
| 16 | 4-Isopropylbenzyl salicylate | 94134-93-7 |
| 17 | 3-Imidazol-4-ylacrylic acid and its ethyl ester | 104-98-3 |
| 18 | Ethyl 2-cyano-3,3-diphenylacrylate | 5232-99-5 |
| 19 | 2'-Ethylhexyl 2-cyano-3,3-diphenylacrylate | 6197-30-4 |
| 20 | Menthyl o-aminobenzoate or: 5-methyl-2-(1-methylethyl)-2-aminobenzoate | 134-09-8 |
| 21 | Glyceryl p-aminobenzoate or: 1-glyceryl 4-aminobenzoate | 136-44-7 |
| 22 | 2,2'-Dihydroxy-4-methoxybenzophenone (dioxybenzone) | 131-53-3 |
| 23 | 2-Hydroxy-4-methoxy-4-methylbenzophenone (mexenone) | 1641-17-4 |
| 24 | Triethanolamine salicylate | 2174-16-5 |
| 25 | Dimethoxyphenylglyoxalic acid or: 3,4-dimethoxyphenylglyoxal acidic sodium | 4732-70-1 |
| 26 | 3-(4'Sulfobenzylidene)bornan-2-one and its salts | 56039-58-8 |
| 27 | 4-tert-Butyl-4'-methoxydibenzoylmethane | 70356-09-1 |
| 28 | 2,2',4,4'-Tetrahydroxybenzophenone | 131-55-5 |
| 29 | 2,2'-methylenebis[6-(2H-benzotriazol-2-yl)-4-(1,1,3,3,-tetramethylbutyl)phenol] | 103597-45-1 |
| 30 | 2,2'-(1,4-phenylene)bis-1H-benzimidazole-4,6-disulfonic acid, Na salt | 180898-37-7 |
| 31 | 2,4-bis[4-(2-Ethylhexyloxy)-2-hydroxy]phenyl-6-(4-methoxyphenyl)(1,3,5)-triazine | 187393-00-6 |
| 32 | 3-(4-methylbenzylidene)camphor | 36861-47-9 |
| 33 | Polyethoxyethyl 4-bis(polyethoxy)paraaminobenzoate | 113010-52-9 |
| 34 | 2,4-Dihydroxybenzophenone | 131-56-6 |
| 35 | 2,2'-Dihydroxy-4,4'-dimethoxybenzophenone 5,5'-disodium sulfonate | 3121-60-6 |
| 36 | Benzoic acid, 2-[4-(diethylamino)-2-hydroxybenzoyl]-, hexyl ester | 302776-68-7 |
| 37 | 2-(2H-Benzotriazol-2-yl)-4-methyl-6-[2-methyl-3-[1,3,3,3-tetramethyl-1-[(trimethylsilyl)oxy]disiloxanyl]propyl]phenol | 155633-54-8 |
| 38 | 1,1-[(2,2'-Dimethylpropoxy)carbonyl]-4,4-diphenyl-1,3-butadiene | 363602-15-7 |

Suitable UV photoprotective filters with the CAS No. 113010-52-9 are commercially available, for example, under the name Uvinul®P 25.

Polymeric or polymer-bound filter substances can also be used according to the invention.

Metal oxides such as titanium dioxide or zinc oxide can likewise be used advantageously for protecting against harmful solar radiation. Their effect is essentially based on reflection, scattering and absorption of the harmful UV radiation and essentially depends on the primary particle size of the metal oxides. The hair cosmetic preparations according to the invention can, furthermore, advantageously comprise inorganic pigments based on metal oxides and/or other metal compounds which are insoluble or sparingly soluble in water, chosen from the group of oxides of zinc (ZnO), iron (e.g. $Fe_2O_3$), zirconium ($ZrO_2$), silicon ($SiO_2$), manganese (e.g. MnO), aluminum ($Al_2O_3$), cerium (e.g. $Ce_2O_3$), mixed oxides of the corresponding metals, and mixtures of such oxides. They are particularly preferably pigments based on ZnO.

The inorganic pigments can here be present in coated form, i.e. that they are treated superficially. This surface treatment can, for example, consist in providing the pigments with a thin hydrophobic layer by a method known per se, as described in DE-A-33 14 742.

Photoprotective agents suitable for use in the preparations according to the invention are the compounds specified in EP-A 1 084 696 in paragraphs [0036] to [0053], which is hereby incorporated in its entirety at this point by reference. Of suitability for the use according to the invention are all UV photoprotective filters which are specified in Annex 7 (to §3b) of the German Cosmetics Directive under "Ultraviolet filters for cosmetic compositions".

The list of specified UV photoprotective filters which can be used in the preparations according to the invention is not exhaustive.

Thickeners

Suitable thickeners are specified in "Kosmetik and Hygiene von Kopf bis Fuß" [Cosmetics and hygiene from head to foot], Ed. W. Umbach, 3rd Edition, Wiley-VCH, 2004, pp. 235-236, which is hereby incorporated in its entirety at this point by reference.

Consistency regulators allow the desired viscosity of, for example, shampoos to be set. Thickeners which have a viscosity-increasing effect due to the surfactant micelles increasing in size or due to swelling of the water phase originate from chemically very different classes of substances.

Suitable thickeners for the preparations according to the invention are crosslinked polyacrylic acids and derivatives thereof, polysaccharides such as xanthan gum, guar guar, agar agar, alginates or tyloses, cellulose derivatives, e.g. carboxymethylcellulose or hydroxycarboxymethylcellulose, also higher molecular weight polyethylene glycol mono- and diesters of fatty acids, fatty alcohols, monoglycerides and fatty acids, polyvinyl alcohol and polyvinylpyrrolidone.

Suitable thickeners are also polyacrylates, such as Carbopol® (Noveon), Ultrez® (Noveon), Luvigel® EM (BASF), Capigel®98 (Seppic), Synthalene® (Sigma), the Aculyn® grades from Rohm and Haas, such as Aculyn® 22 (copolymer of acrylates and methacrylic acid ethoxylates with stearyl radical (20 EO units)) and Aculyn® 28 (copolymer of acrylates and methacrylic acid ethoxylates with behenyl radical (25 EO units)).

Suitable thickeners are also, for example, Aerosil grades (hydrophilic silicas), polyacrylamides, polyvinyl alcohol and polyvinylpyrrolidone, surfactants such as, for example, ethoxylated fatty acid glycerides, esters of fatty acids with polyols, such as, for example, pentaerythritol or trimethylolpropane, fatty alcohol ethoxylates with a narrowed homolog distribution or alkyl oligoglucosides, and electrolytes, such as sodium chloride and ammonium chloride.

Particularly preferred thickeners for producing gels are Ultrez®21, Aculyn®28, Luvigel® EM and Capigel®98.

Particularly in the case of more highly concentrated shampoo formulations it is also possible, to regulate the consistency, to add substances which reduce the viscosity of the formulation, such as, for example, propylene glycol and glycerol. These substances influence the product properties only slightly.

Gel Formers

If the use of gel formers is desired for the preparations according to the invention, then all gel formers customary in cosmetics can be used. These include slightly crosslinked polyacrylic acid, for example Carbomer (INCI), cellulose derivatives, e.g. Hydroxypropylcellulose, Hydroxyethylcellulose, cationically modified celluloses, polysaccharides, e.g. Xanthan gum, Caprylic/Capric Triglyceride, Sodium Acrylates Copolymer, Polyquaternium-32 (and) Paraffinum Liquidum (INCI), Sodium Acrylates Copolymer (and) Paraffinum Liquidum (and) PPG-1 Trideceth-6, Acrylamidopropyl Trimonium Chloride/Acrylamide Copolymer, Steareth-10 Allyl Ether Acrylates Copolymer, Polyquaternium-37 (and) Paraffinum Liquidum (and) PPG-1 Trideceth-6, Polyquaternium 37 (and) Propylene Glycole Dicaprate Dicaprylate (and) PPG-1 Trideceth-6, Polyquaternium-7, Polyquaternium-44.

Emulsifiers

Suitable emulsifiers are, for example, nonionogenic surfactants from at least one of the following groups:

Addition products of from 2 to 30 mol of ethylene oxide and/or 0 to 5 mol of propylene oxide onto linear fatty alcohols having 8 to 22 carbon atoms, onto fatty acids having 12 to 22 carbon atoms and onto alkylphenols having 8 to 15 carbon atoms in the alkyl group;

C12/18 fatty acid mono- and diesters of addition products of from 1 to 30 mol of ethylene oxide onto glycerol;

glycerol mono- and diesters and sorbitan mono- and diesters of saturated and unsaturated fatty acids having 6 to 22 carbon atoms and ethylene oxide addition products thereof;

alkyl mono- and oligoglycosides having 8 to 22 carbon atoms in the alkyl radical and ethoxylated analogues thereof;

addition products of from 15 to 60 mol of ethylene oxide onto castor oil and/or hydrogenated castor oil;

polyol and in particular polyglycerol esters, such as, for example, polyglycerol polyricinoleate, polyglycerol poly-12-hydroxystearate or polyglycerol dimerate. Likewise suitable are mixtures of compounds from two or more of these classes of substance;

addition products of from 2 to 15 mol of ethylene oxide onto castor oil and/or hydrogenated castor oil;

partial esters based on linear, branched, unsaturated or saturated $C_6/_{22}$-fatty acids, ricinoleic acid and 12-hydroxystearic acid and glycerol, polyglycerol, pentaerythritol, dipentaerythritol, sugar alcohols (e.g. sorbitol), alkyl glucosides (e.g. methyl glucoside, butyl glucoside, lauryl glucoside) and polyglucosides (e.g. cellulose);

mono-, di- and trialkyl phosphates, and mono-, di- and/or tri-PEG alkyl phosphates and salts thereof;

wool wax alcohols;

polysiloxane-polyalkyl-polyether copolymers and corresponding derivatives;

mixed esters of pentaerythritol, fatty acids, citric acid and fatty alcohol according to German patent 1165574 and/ or mixed esters of fatty acids having 6 to 22 carbon atoms, methylglycose and polyols, preferably glycerol or polyglycerol and polyalkylene glycols.

The addition products of ethylene oxide and/or of propylene oxide onto fatty alcohols, fatty acids, alkylphenols, glycerol mono- and diesters, and also sorbitan mono- and diesters of fatty acids or onto castor oil are known, commercially available products. These are homolog mixtures whose average degree of alkoxylation corresponds to the ratio of the quantitative amounts of ethylene oxide and/or propylene oxide and substrate with which the addition reaction is carried out. $C_{12}$ to $C_{18}$-fatty acid mono- and diesters of addition products of ethylene oxide onto glycerol are known from German patent 2024051 as refatting agents for cosmetic preparations. $C_8$ to $C_{18}$-alkyl mono- and oligoglycosides, their preparation and their use are known from the prior art.

Their preparation takes place in particular by reacting glucose or oligosaccharides with primary alcohols having 8 to 18 carbon atoms. With regard to the glycoside ester, both monoglycosides in which a cyclic sugar radical is glycosidicaliy bonded to the fatty alcohol, and also oligomeric glycosides with a degree of oligomerization up to preferably about 8 are suitable. The degree of oligomerization here is a statistical average value which is based on a homolog distribution customary for such technical-grade products.

In addition, zwitterionic surfactants can be used as emulsifiers. Zwitterionic surfactants is the term used to refer to those surface-active compounds which carry at least one quaternary ammonium group and at least one carboxylate group and/or one sulfonate group in the molecule. Particularly suitable zwitterionic surfactants are the so-called betaines, such as the N-alkyl-N,N-dimethylammonium glycinates, for example cocoalkyldimethylammonium glycinate, N-acylaminopropyl-N,N-dimethylammonium glycinates, for example cocoacylaminopropyldimethylammonium glycinate, and 2-alkyl-3-carboxymethyl-3-hydroxyethylimidazolines each having 8 to 18 carbon atoms in the alkyl or acyl group, and cocoacylaminoethyl hydroxyethylcarboxymethyl glycinate.

Particular preference is given to the fatty acid amide derivative known under the CTFA name Cocamidopropyl Betaine. Likewise suitable emulsifiers are ampholytic surfactants. Ampholytic surfactants are understood as meaning those surface-active compounds which, apart from a $C_8$ to $C_{18}$ alkyl or -acyl group in the molecule, comprise at least one free amino group and at least one —COON and/or —$SO_3H$ group and are capable of forming internal salts. Examples of suitable ampholytic surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids having in each case about 8 to 18 carbon atoms in the alkyl group. Particularly preferred ampholytic surfactants are N-cocoalkylaminopropionate, cocoacylaminoethylaminopropionate and $C_{12}$ to $C_{18}$-acylsarcosine.

Besides the ampholytic emulsifiers, quaternary emulsifiers are also suitable, particular preference being given to those of the esterquat type, preferably methyl-quaternized difatty acid triethanolamine ester salts.

Antioxidants

An additional content of antioxidants in the preparations may be advantageous. According to the invention, antioxidants which may be used are all antioxidants which are customary or suitable for cosmetic applications. The antioxidants are advantageously chosen from the group consisting of amino acids (e.g. glycine, histidine, tyrosine, tryptophan) and derivatives thereof, imidazoles (e.g. urocanic acid) and derivatives thereof, peptides, such as D,L-carnosine, D-carnosine, L-carnosine and derivatives thereof (e.g. anserine), carotenoids, carotenes (e.g. α-carotene, β-carotene, γ-lycopene) and derivatives thereof, chlorogenic acid and derivatives thereof, lipoic acid and derivatives thereof (e.g. dihydrolipoic acid), aurothioglucose, propylthiouracil and other thiols (e.g. thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts), and sulfoximine compounds (e.g. buthionine sulfoximines, homocysteine sulfoximine, buthionine sulfones, penta-, hexa-, heptathionine sulfoxamine) in very low tolerated doses (e.g. pmol to μmol/kg), also (metal)chelating agents (e.g. α-hydroxy fatty acids, palmitic acid, phytic acid, lactoferrin), α-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof (e.g. γ-linolenic acid, linoleic acid, oleic acid), folic acid and derivatives thereof, furfurylidenesorbitol and derivatives thereof, ubiquinone and ubiquinol and derivatives thereof, vitamin C and derivatives (e.g. ascorbyl palmitate, Mg ascorbyl phosphate, ascorbyl acetate), tocopherols and derivatives (e.g. vitamin E acetate), vitamin A and derivatives (vitamin A palmitate), and coniferyl benzoate of benzoin resin, rutinic acid and derivatives thereof, α-glycosylrutin, ferulic acid, furfurylideneglucitol, carnosine, butylhydroxytoluene, butylhydroxyanisol, nordihydroguaiacic acid, nordihydroguaiaretic acid, trihydroxybutyrophenone, uric acid and derivatives thereof, mannose and derivatives thereof, zinc and derivatives thereof (e.g. ZnO, $ZnSO_4$), selenium and derivatives thereof (e.g. selenomethionine), stilbenes and derivatives thereof (e.g. stilbene oxide, trans-stilbene oxide) and the derivatives (salts, esters, ethers, sugars, nucleotides, nucleosides, peptides and lipids) suitable according to the invention of these specified active ingredients.

The amount of the abovementioned antioxidants (one or more compounds) in the preparations is preferably 0.001 to 30% by weight, particularly preferably 0.05 to 20% by weight, in particular 0.1 to 10% by weight, based on the total weight of the preparation.

If vitamin E and/or derivatives thereof are the antioxidant or the antioxidants, it is advantageous to provide these in concentrations of from 0.001 to 10% by weight, based on the total weight of the preparation.

If vitamin A or vitamin A derivatives, or carotenes or derivatives thereof are the antioxidant or the antioxidants, it is advantageous to provide these in concentrations of from 0.001 to 10% by weight, based on the total weight of the preparation.

Perfume Oils

The skin or hair cosmetic preparations can comprise perfume oils. Perfume oils which may be mentioned are, for example, mixtures of natural and synthetic fragrances. Natural fragrances are extracts of flowers (lily, lavendar, rose, jasmine, neroli, ylang-ylang), stems and leaves (geranium, patchouli, petitgrain), fruits (anise, coriander, caraway, juniper), fruit peels (bergamot, lemon, orange), roots (mace, angelica, celery, cardamom, costus, iris, calmus), woods (pine wood, sandalwood, guaiac wood, cedar wood, rosewood), herbs and grasses (tarragon, lemongrass, sage, thyme), needles and branches (spruce, fir, pine, dwarf-pine), resins and balsams (galbanum, elemi, benzoin, myrrh, olibanum, opoponax). Also suitable are animal raw materials, such as, for example, civet and castoreum. Typical synthetic fragrance compounds are products of the ester, ether, aldehyde, ketone, alcohol and hydrocarbon type. Fragrance compounds of the ester type are, for example, benzyl acetate, phenoxyethyl isobutyrate, 4-tert-butylcyclohexyl acetate, linalyl acetate, dimethylbenzylcarbinyl acetate, phenylethyl acetate, linalyl benzoate, benzyl formate, ethylmethylphenyl glycinate, allyl cyclohexyl propionate, styrallyl propionate and benzyl salicylate. The ethers include, for example, benzyl ethyl ether, the aldehydes include, for example, the linear alkanals having 8 to 18 carbon atoms, citral, citronellal, citronellyloxyacetaldehyde, cyclamenaldehyde, hydroxycitronellal, lilial and bourgeonal, the ketones include, for example, the ionones, cc-isomethylionone and methyl cedryl ketone, the alcohols include anethol, citronellol, eugenol, isoeugenol, geraniol, linalool, phenylethyl alcohol and terpineol, and the hydrocarbons include primarily the terpenes and balsams. However, preference is given to using mixtures of different fragrances which together produce a pleasing scent note. Essential oils of lower volatility, which are mostly used as aroma components, are also suitable as perfume oils, e.g. sage oil, camomile oil, oil of cloves, melissa oil, mint oil, cinnamon leaf oil, linden blossom oil, juniper berry oil, vetiver oil, olibanum oil, galbanum oil, labdanum oil and lavandin oil. Preference is given to using bergamot oil, dihydromyrcenol, lilial, lyral, citronellol, phenylethyl alcohol, a-hexylcinnamaldehyde, geraniol, benzyl acetone, cyclamenaldehyde, linalool, boisambrene forte, ambroxan, indole, hedione, sandelice, lemon oil, mandarin oil, orange oil, allyl amyl glycolate, cyclovertal, lavandin oil, clary sage oil, β-damascone, geranium oil bourbon, cyclohexyl salicylate, vertofix coeur, iso-E-super, Fixolide NP, evernyl, iraldein gamma, phenylacetic acid, geranyl acetate, benzyl acetate, rose oxide, rommilat, irotyl and floramat alone or in mixtures.

Superfatting Agents

Superfatting agents which may be used are substances such as, for example, lanolin and lecithin, and polyethoxylated or acylated lanolin and lecithin derivatives, polyol fatty acid esters, monoglycerides and fatty acid alkanolamides, the latter serving as foam stabilizers at the same time.

Silicone Compounds

In one embodiment, the preparations according to the invention comprise, as haircare additive, at least one silicone compound in an amount of preferably 0.01 to 15% by weight, particularly preferably from 0.1 to 5% by weight. The silicone compounds comprise volatile and nonvolatile silicones and silicones which are insoluble or soluble in the composition. In one embodiment, they are high molecular weight silicones with a viscosity of from 1000 to 2 000 000 cSt at 25° C., preferably 10 000 to 1 800 000 or 100 000 to 1 500 000. The silicone compounds comprise polyalkyl- and polyaryl-siloxanes, in particular with methyl, ethyl, propyl, phenyl, methylphenyl and phenylmethyl groups. Preference is given to polydimethylsiloxanes, polydiethylsiloxanes, polymethylphenylsiloxane. Preference is also given to shine-imparting, arylated silicones with a refractive index of at least 1.46, or at least 1.52. The silicone compounds comprise in particular the substances with the INCI names cyclomethicone, dimethicone, dimethiconol, dimethicone copolyol, phenyl trimethicone, amodimethicone, trimethylsilylamodimethicone, stearyl siloxysilicate, polymethylsilsesquioxane, dimethicone crosspolymer. Also suitable are silicone resins and silicone elastomers, which are highly crosslinked siloxanes.

Preferred silicones are cyclic dimethylsiloxanes, linear polydimethylsiloxanes, block polymers of polydimethylsiloxane and polyethylene oxide and/or polypropylene oxide, polydimethylsiloxanes with terminal or lateral polyethylene oxide or polypropylene oxide radicals, polydimethylsiloxanes with terminal hydroxyl groups, phenyl-substituted polydimethylsiloxanes, silicone emulsions, silicone elastomers, silicone waxes, silicone gums and amino-substituted silicones.

Hair Conditioners

In one embodiment, the preparations according to the invention comprise 0.01 to 20% by weight, preferably from 0.05 to 10% by weight, particularly preferably from 0.1 to 5% by weight, of at least one conditioner.

Conditioners preferred according to the invention are, for example, all compounds which are listed in the International Cosmetic Ingredient Dictionary and Handbook (Volume 4, Editor: R. C. Pepe, J. A. Wenninger, G. N. McEwen, The Cosmetic, Toiletry, and Fragrance Association, 9th Edition, 2002) under Section 4 under the keywords Hair Conditioning Agents, Humectants, Skin-Conditioning Agents, Skin-Conditioning Agents-Emollient, Skin-Conditioning Agents-Humectant, Skin-Conditioning Agents-Miscellaneous, Skin-Conditioning Agents-Occlusive and Skin Protectants, and all of the compounds listed in EP-A 934 956 (pp. 11-13) under "water soluble conditioning agent" and "oil soluble conditioning agent". Further advantageous conditioning agents are, for example, the compounds referred to in accordance with INCI as polyquaternium (in particular Polyquaternium-1 to Polyquaternium-56).

Suitable conditioning agents include, for example, also polymeric quaternary ammonium compounds, cationic cellulose derivatives, chitosan derivatives and polysaccharides.

The conditioner is preferably chosen from betaine, panthenol, panthenyl ethyl ether, sorbitol, protein hydrolysates, plant extracts; A-B block copolymers of alkyl acrylates and alkyl methacrylates; A-B block copolymers of alkylmethacrylates and acrylonitrile; A-B-A block copolymers of lactide and ethylene oxide; A-B-A block copolymers of caprolactone and ethylene oxide; A-B-C block copolymers of alkylene or alkadiene compounds, styrene and alkyl methacrylates; A-B-C block copolymers of acrylic acid, styrene and alkyl methacrylates, star-shaped block copolymers, hyperbranched polymers, dendrimers, intrinsically electrically conductive 3,4-polyethylenedioxythiophenes and intrinsically electrically conductive polyanilines.

Further conditioners advantageous according to the invention are cellulose derivatives and quaternized guar gum derivatives, in particular guar hydroxypropylammonium chloride (e.g. Jaguar Excel®, Jaguar C 162® (Rhodia), CAS 65497-29-2, CAS 39421-75-5).

Nonionic poly-N-vinylpyrrolidone/polyvinyl acetate copolymers (e.g. Luviskol®VA 64 (BASF)), anionic acrylate copolymers (e.g. Luviflex®Soft (BASF)), and/or amphoteric amidefacrylate/methacrylate copolymers (e.g. Amphomer® (National Starch)) can also be used advantageously according to the invention as conditioning agents.

Hydrotropes

To improve the flow behavior, hydrotropes, such as, for example, ethanol, isopropyl alcohol, or polyols, can also be used. Polyols which are suitable here have preferably 2 to 15 carbon atoms and at least two hydroxyl groups. Typical examples are glycerol;

alkylene glycols, such as, for example, ethylene glycol, diethylene glycol, propylene glycol, butylene glycol, hexylene glycol, and polyethylene glycols with an average molecular weight of from 100 to 1000 daltons;

technical-grade oligoglycerol mixtures with a degree of self-condensation of from 1.5 to 10, such as, for example, technical-grade diglycerol mixtures with a diglycerol content of from 40 to 50% by weight;

methylol compounds, such as, in particular, trimethylolethane, trimethylolpropane, trimethylolbutane, pentaerythritol and dipentaerythritol;

lower alkyl glucosides, in particular those with 1 to 8 carbon atoms in the alkyl radical, such as, for example, methyl and butyl glucoside;

sugar alcohols having 5 to 12 carbon atoms, such as, for example, sorbitol or mannitol;

sugars having 5 to 12 carbon atoms, such as, for example, glucose or sucrose;

amino sugars, such as, for example, glucamine.

Oils, Fats and Waxes

The skin or hair cosmetic preparations according to the invention can also comprise oils, fats or waxes. These are advantageously chosen from the group of lecithins and fatty acid triglycerides, namely the triglycerol esters of saturated and/or unsaturated, branched and/or unbranched alkanecarboxylic acids with a chain length of from 8 to 24, in particular 12 to 18, carbon atoms. The fatty acid triglycerides can, for example, be chosen advantageously from the group of synthetic, semisynthetic and natural oils, such as, for example, olive oil, sunflower oil, soybean oil, peanut oil, rapeseed oil, almond oil, palm oil, coconut oil, castor oil, wheatgerm oil, grapeseed oil, thistle oil, evening primrose oil, macadamia nut oil and the like. Further polar oil components can be chosen from the group of esters of saturated and/or unsaturated, branched and/or unbranched alkanecarboxylic acids with a chain length from 3 to 30 carbon atoms and saturated and/or unsaturated, branched and/or unbranched alcohols with a chain length of from 3 to 30 carbon atoms, and from the group of esters of aromatic carboxylic acids and saturated and/or unsaturated, branched and/or unbranched alcohols with a chain length of from 3 to 30 carbon atoms. Such ester oils can then advantageously be chosen from the group consisting of isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate, dicaprylyl carbonate (Cetiol CC) and cocoglycerides (Myritol 331), butylene glycol dicaprylate/dicaprate and dibutyl adipate, and synthetic, semisynthetic and natural mixtures of such esters, such as, for example, jojoba oil.

In addition, one or more oil components can be chosen advantageously from the group of branched and unbranched hydrocarbons and hydrocarbon waxes, silicone oils, dialkyl ethers, the group of saturated or unsaturated, branched or unbranched alcohols.

Any mixtures of such oil and wax components are also to be used advantageously for the purposes of the present invention. It may also, if appropriate, be advantageous to use waxes, for example cetyl palmitate, as the sole lipid component of the oil phase.

According to the invention, the oil component is advantageously chosen from the group consisting of 2-ethylhexyl isostearate, octyldodecanol, isotridecyl isononanoate, isoeicosane, 2-ethylhexyl cocoate, C12-15-alkyl benzoate, caprylic-capric triglyceride, dicaprylyl ether.

Mixtures of C12-15-alkyl benzoate and 2-ethylhexyl isostearate, mixtures of C12-15-alkyl benzoate and isotridecyl isononanoate, and mixtures of C12-C15-alkyl benzoate, 2-ethylhexyl isostearate and isotridecyl isononanoate are advantageous according to the invention.

According to the invention, particular preference is given to using fatty acid triglycerides, in particular soybean oil and/or almond oil, as oils with a polarity of from 5 to 50 mN/m.

In addition, the oil phase can advantageously be chosen from the group of Guerbet alcohols. These are liquid even at low temperatures and cause virtually no skin irritations. They can be used advantageously as fatting, superfatting and also refatting constituents in cosmetic compositions.

The use of Guerbet alcohols in cosmetics is known per se.

Guerbet alcohols preferred according to the invention are 2-butyloctanol (available commercially, for example, as Isofol®12 (Condea)) and 2-hexyldecanol (available commercially, for example, as Isofol®16 (Condea)).

According to the invention, mixtures of Guerbet alcohols according to the invention are also to be used advantageously, such as, for example, mixtures of 2-butyloctanol and 2-hexyldecanol (commercially available, for example, as Isofol®14 (Condea)).

Any mixtures of such oil and wax components are also to be used advantageously for the purposes of the present invention. Among the polyolefins, polydecenes are the preferred substances.

Fat and/or wax components to be used advantageously according to the invention can be chosen from the group of vegetable waxes, animal waxes, mineral waxes and petrochemical waxes. For example, candelilla wax, carnauba wax, japan wax, esparto grass wax, cork wax, guaruma wax, ricegerm oil wax, sugarcane wax, berry wax, ouricury wax, montan wax, jojoba wax, shea butter, beeswax, shellac wax, spermaceti, lanolin (wool wax), uropygial grease, ceresine, ozokerite (earth wax), paraffin waxes and microwaxes are advantageous.

Further advantageous fat and/or wax components are chemically modified waxes and synthetic waxes, such as, for example, Syncrowax®HRC (glyceryl tribehenate), and Syncrowax®AW 1 C ($C_{18-36}$-fatty acid) and montan ester waxes, sasol waxes, hydrogenated jojoba waxes, synthetic or modified beeswaxes (e.g. dimethicone copolyol beeswax and/or $C_{30-50}$-alkyl beeswax), cetyl ricinoleates, such as, for example, Tegosoft®CR, polyalkylene waxes, polyethylene glycol waxes, but also chemically modified fats, such as, for example, hydrogenated vegetable oils (for example hydrogenated castor oil and/or hydrogenated coconut fatty glycerides), triglycerides, such as, for example, hydrogenated soy glyceride, trihydroxystearin, fatty acids, fatty acid esters and glycol esters, such as, for example, $C_{20-40}$-alkyl stearate, $C_{20-40}$-alkyl hydroxystearoylstearate and/or glycol montanate. Furthermore, certain organosilicon compounds which have similar physical properties to the specified fat and/or wax components, such as, for example, stearoxytrimethylsilane, are also advantageous.

According to the invention, the fat and/or wax components can be used either individually or as a mixture in the compositions.

Any mixtures of such oil and wax components are also to be used advantageously for the purposes of the present invention.

The oil phase is advantageously chosen from the group consisting of 2-ethylhexyl isostearate, octyldodecanol, isotridecyl isononanoate, butylene glycol dicaprylate/dicaprate, 2-ethylhexyl cocoate, $C_{12-15}$alkyl benzoate, caprylic/capric triglyceride, dicaprylyl ether.

Mixtures of octyldodecanol, caprylic/capric triglyceride, dicaprylyl ether, dicaprylyl carbonate, cocoglycerides or mixtures of $C_{12-15}$-alkyl benzoate and 2-ethylhexyl isostearate, mixtures of $C_{12-15}$-alkyl benzoate and butylene glycol dicaprylate/dicaprate and mixtures of $C_{12-15}$-alkyl benzoate, 2-ethylhexyl isostearate and isotridecyl isononanoate are particularly advantageous.

Of the hydrocarbons, paraffin oil, cycloparaffin, squalene, squalane, hydrogenated polyisobutene and polydecene are to be used advantageously for the purposes of the present invention.

The oil component is also advantageously chosen from the group of phospholipids. According to the invention, paraffin oil advantageous according to the invention which may be used is Merkur® white oil Pharma 40 from Merkur Vaseline, Shell Ondina® 917, Shell Ondina® 927, Shell Oil 4222, Shell Ondina®933 from Shell & DEA Oil, Pionier® 6301 S, Pionier® 2071 (Hansen & Rosenthal).

Suitable cosmetically compatible oil and fat components are described in Karl-Heinz Schrader, Grundlagen and Rezepturen der Kosmetika [Fundamentals and formulations of cosmetics], 2nd Edition, Verlag Hüthig, Heidelberg, pp. 319-355, which is hereby incorporated in its entirety by reference.

The content of oils, fats and waxes is at most 30% by weight, preferably 20% by weight, further preferably at most 10% by weight, based on the total weight of the composition.

Pigments

In one embodiment, the preparations according to the invention comprise at least one pigment. These may be colored pigments which impart color effects to the product mass or to the hair, or they may be luster effect pigments which impart luster effects to the product mass or to the hair. The color effects or luster effects on the hair are preferably temporary, i.e. they remain on the hair until the next hair wash and can be removed again by washing the hair with customary shampoos.

The pigments are present in the product mass in undissolved form and may be present in an amount of from 0.01 to 25% by weight, particularly preferably from 5 to 15% by weight. The preferred particle size is 1 to 200 µm, in particular 3 to 150 µm, particularly preferably 10 to 100 µm. The pigments are colorants which are virtually insoluble in the application medium and may be inorganic or organic. Inorganic-organic mixed pigments are also possible. Preference is given to inorganic pigments. The advantage of the inorganic pigments is their excellent stability to light, weather and temperature. The inorganic pigments may be of natural origin, prepared for example from chalk, ochre, umber, green earth, burnt sienna or graphite. The pigments may be white pigments, such as, for example, titanium dioxide or zinc oxide, black pigments, such as, for example, iron oxide black, colored pigments, such as, for example, ultramarine or iron oxide red, luster pigments, metal effect pigments, pearlescent pigments, and fluorescent or phosphorescent pigments, with preferably at least one pigment being a colored, non-white pigment.

Metal oxides, hydroxides and oxide hydrates, mixed phase pigments, sulfur-containing silicates, metal sulfides, complex metal cyanides, metal sulfates, chromates and molybdates, and the metals themselves (bronze pigments) are suitable. Titanium dioxide (CI 77891), black iron oxide (CI 77499), yellow iron oxide (CI 77492), red and brown iron oxide (CI 77491), manganese violet (CI 77742), ultramarine (sodium aluminum sulfosilicates, CI 77007, Pigment Blue 29), chromium oxide hydrate (CI 77289), iron blue (ferric ferrocyanide, CI 77510), carmine (cochineal) are particularly suitable.

Particular preference is given to pearlescent pigments and colored pigments based on mica which are coated with a metal oxide or a metal oxychloride such as titanium dioxide or bismuth oxychloride and, if appropriate, further color-imparting substances, such as iron oxides, iron blue, ultramarine, carmine etc. and where the color can be determined by varying the layer thickness. Such pigments are sold, for example, under the trade names Rona®, Colorona®, Dichrona® and Timiron® by Merck, Germany.

Organic pigments are, for example, the natural pigments sepia, gamboge, bone charcoal, Cassel brown, indigo, chlorophyll and other plant pigments. Synthetic organic pigments are, for example, azopigments, anthraquinoids, indigoids, dioxazine, quinacridone, phthalocyanine, isoindolinone, perylene and perinone, metal complex, alkali blue and diketopyrrolopyrrole pigments.

In one embodiment, the preparations according to the invention comprise 0.01 to 10% by weight, particularly preferably from 0.05 to 5% by weight, of at least one particulate substance. Suitable substances are, for example, substances which are solid at room temperature (25° C.) and are in the form of particles. For example, silica, silicates, aluminates, clay earths, mica, salts, in particular inorganic metal salts, metal oxides, e.g. titanium dioxide, minerals and polymer particles are suitable.

The particles are present in the composition in undissolved, preferably stably dispersed, form and, following application to the application surface and evaporation of the solvent, can be deposited in solid form.

Preferred particulate substances are silica (silica gel, silicon dioxide) and metal salts, in particular inorganic metal salts, with silica being particularly preferred. Metal salts are, for example, alkali metal or alkaline earth metal halides, such as sodium chloride or potassium chloride; alkali metal or alkaline earth metal sulfates, such as sodium sulfate or magnesium sulfate.

Suitable repellent active ingredients are compounds which are able to keep off or drive away certain animals, in particular insects, from people. These include, for example, 2-ethyl-1, 3-hexanediol, N,N-diethyl-m-toluamide etc.

Suitable hyperemic substances, which stimulate the circulation of blood through the skin, are, for example, essential oils, such as dwarf pine, lavender, rosemary, juniper berry, horse chestnut extract, birch leaf extract, hay flower extract, ethyl acetate, camphor, menthol, peppermint oil, rosemary extract, eucalyptus oil, etc.

Suitable keratolytic and keratoplastic substances are, for example, salicylic acid, calcium thioglycolate, thioglycolic acid and its salts, sulfur, etc. Suitable antidandruff active ingredients are, for example, sulfur, sulfur polyethylene glycol sorbitan monooleate, sulfur ricinol polyethoxylate, zinc pyrithione, aluminum pyrithione, etc.

Suitable antiphlogistics, which counteract skin irritations, are, for example, allantoin, bisabolol, dragosantol, camomile extract, panthenol, etc.

Application Form

In a preferred embodiment, the preparations according to the invention are sprayable, for example as aerosol or pump spray preparation.

The preparations according to the invention can be used in various application forms, such as, for example, as lotion, as nonaerosol spray lotion, which is used by means of a mechanical device for spraying, as aerosol spray which is sprayed using a propellant, as aerosol foam or as nonaerosol foam, which is present in combination with a suitable mechanical device for foaming the composition, as hair cream, as hair wax, as gel, as liquid gel, as sprayable gel or as foam gel.

Use in the form of a lotion thickened with a customary thickener is also possible.

In one embodiment, the composition according to the invention is in the form of a gel, in the form of a viscous lotion or in the form of a spray gel which is sprayed using a mechanical device, and comprises at least one of the abovementioned thickeners in an amount of from preferably 0.05 to 10% by weight, particularly preferably from 0.1 to 2% by weight and has a viscosity of at least 250 mPas. The viscosity of the gel is preferably from 500 to 50 000 mPas, particularly preferably from 1000 to 15 000 mPas at 25° C.

In another embodiment, the preparation according to the invention is in the form of an O/W emulsion, a W/O emulsion or a microemulsion and comprises at least one of the abovementioned oils or waxes emulsified in water, and at least one cosmetically customary surfactant.

In a preferred embodiment, the preparation according to the invention is in the form of a spray product, either in combination with a mechanical pump spray device or in combination with at least one of the abovementioned propellants. A preferred aerosol spray additionally comprises propellants in an amount such that the total amount of the volatile organic components does not exceed 80% by weight, in particular 55% by weight of the preparation and is bottled in a pressurized container.

A nonaerosol hairspray is sprayed using a suitable mechanically operated spray device. Mechanical spray devices are understood as meaning those devices which permit the spraying of a composition without use of a propellant. A suitable mechanical spray device which may be used is, for example, a spray pump or an elastic container provided with a spray valve in which the hair cosmetic preparation according to the invention is bottled under pressure, where the elastic container expands and from which the composition is continuously dispensed as a result of the contraction of the elastic container from opening the spray valve.

In a further embodiment, the preparation according to the invention is in the form of a foamable product (mousse) in combination with a device for foaming, comprises at least one customary foam-imparting substance known for this purpose, e.g. at least one foam-forming surfactant or at least one foam-forming polymer. Devices for foaming are understood as meaning those devices which permit the foaming of a liquid with or without use of a propellant. A suitable mechanical foam device which can be used is, for example, a commercially customary pump foamer or an aerosol foam head. The product is present either in combination with a mechanical pump foam device (pump foam) or in combination with at least one propellant (aerosol foam) in an amount of from preferably 1 to 20% by weight, in particular from 2 to 10% by weight. Propellants are, for example, chosen from propane, butane, dimethyl ether and fluorinated hydrocarbons.

The invention thus provides a hair cosmetic preparation in the form of a spray product, where the preparation is present either in combination with a mechanical pump spray device or in combination with at least one propellant chosen from the group consisting of propane, butane, dimethyl ether, fluorinated hydrocarbons and mixtures thereof.

The composition is foamed directly prior to use and incorporated into the hair as foam and can then be rinsed out or left in the hair without rinsing out.

In a further embodiment, the preparation according to the invention is in the form of a hair wax, i.e. it has wax-like consistency and comprises at least one of the abovementioned waxes in an amount of from preferably 0.5 to 30% by weight, and if appropriate further water-insoluble substances. The wax-like consistency is preferably characterized in that the needle penetration index (unit of measurement 0.1 mm, test weight 100 g, test time 5 s, test temperature 25° C.; in accordance with DIN 51 579) is greater than or equal to 10, particularly preferably greater than or equal to 20 and that the solidification point of the product is preferably greater than or equal to 30° C. and less than or equal to 70° C., is particularly preferably in the range from 40 to 55° C. Suitable waxes and water-insoluble substances are, in particular, emulsifiers with a HLB value below 7, silicone oils, silicone waxes, waxes (e.g. wax alcohols, wax acids, wax esters, and in particular natural waxes, such as beeswax, carnauba wax etc.), fatty alcohols, fatty acids, fatty acid esters or hydrophilic waxes, such as, for example, high molecular weight polyethylene glycols with a molecular weight of from 800 to 20 000 g/mol, preferably from 2000 to 10 000 g/mol.

If the hair cosmetic preparation according to the invention is in the form of a hair lotion, then it is present as an essentially non-viscous or low-viscosity, flowable solution, dispersion or emulsion with a content of at least 10% by weight, preferably 20 to 95% by weight, of a cosmetically compatible alcohol. Alcohols which can be used are, in particular, the lower alcohols having 1 to 4 carbon atoms customarily used for cosmetic purposes, e.g. ethanol and isopropanol.

If the hair cosmetic preparation according to the invention is in the form of a hair cream, then it is preferably in the form of an emulsion and comprises either additionally viscosity-imparting ingredients in an amount of from 0.1 to 10% by weight, or the required viscosity and creamy consistency is built up through micelle formation with the help of suitable emulsifiers, fatty acids, fatty alcohols, waxes etc. in the customary way.

Skin Cosmetic Compositions

According to a further preferred embodiment, the preparations according to the invention are skin cosmetic preparations, i.e. preparations for the care and protection of the skin or preparations for decorative cosmetics.

Preparations for nail care are not provided by this invention.

Suitable skin cosmetic preparations are, for example, face tonics, face masks, deodorants and other cosmetic lotions. Compositions for use in decorative cosmetics comprise, for example, concealing sticks, stage makeup, mascara and eye shadows, lipsticks, kohl pencils, eyeliners, blushers, powders and eyebrow pencils.

Furthermore, the polymers A can be used in nose strips for pore cleansing, in antiacne compositions, repellants, shaving compositions, hair-removal compositions, intimate care compositions, foot care compositions, and in baby care.

The skin care compositions according to the invention are, in particular, W/O or O/W skin creams, day and night creams, eye creams, face creams, antiwrinkle creams, moisturizing creams, bleaching creams, vitamin creams, skin lotions, care lotions and moisturizing lotions.

Skin cosmetic and dermatological compositions based on the above-described polymers A exhibit advantageous effects. The polymers can, inter alia, contribute to an improvement in the feel of the skin. By adding the polymers according to the invention, it is possible to achieve a considerable improvement in the skin compatibility in certain formulations.

Skin cosmetic and dermatological preparations comprise preferably at least one polymer A in an amount of from about 0.001 to 30% by weight, preferably 0.01 to 20% by weight, very particularly preferably 0.1 to 12% by weight, based on the total weight of the preparation.

Particularly sunscreen compositions based on the polymers A have the property of increasing the residence time of the UV-absorbing ingredients compared to customary auxiliaries such as polyvinylpyrrolidone.

Depending on the field of use, the preparation according to the invention can be applied in a form suitable for skin care, such as, for example, as cream, foam, gel, stick, mousse, milk, spray (pump spray or propellant-containing spray) or lotion.

Besides the polymers A and suitable carriers, the skin cosmetic preparations can also comprise further active ingredients and auxiliaries customary in skin cosmetics, as described above. These include, preferably, emulsifiers, preservatives, perfume oils, cosmetic active ingredients, such as phytantriol, vitamin A, E and C, retinol, bisabolol, panthenol, photoprotective agents, bleaches, colorants, tints, tanning agents, collagen, protein hydrolyzates, stabilizers, pH regulators, dyes, salts, thickeners, gel formers, consistency regulators, silicones, humectants, refatting agents and further customary additives. The ingredients for the skin cosmetic preparations can also be chosen from the ingredients specified above for the hair cosmetic preparations.

Preferred oil and fat components of the skin cosmetic and dermatological preparations are the abovementioned mineral and synthetic oils, such as, for example, paraffins, silicone oils and aliphatic hydrocarbons having more than 8 carbon atoms, animal and vegetable oils, such as, for example, sunflower oil, coconut oil, avocado oil, olive oil, lanolin, or waxes, fatty acids, fatty acid esters, such as, for example, triglycerides of $C_6$-$C_{30}$-fatty acids, wax esters, such as, for example, jojoba oil, fatty alcohols, vaseline, hydrogenated lanolin and acetylated lanolin, and mixtures thereof.

The polymers according to the invention can also be mixed with conventional polymers if specific properties are to be set.

To set certain properties, such as, for example, improving the feel to the touch, the spreading behavior, the water resistance and/or the binding of active ingredients and auxiliaries, such as pigments, the skin cosmetic and dermatological preparations can additionally also comprise conditioning substances based on silicone compounds. Suitable silicone compounds are, for example, polyalkylsiloxanes, polyarylsiloxanes, polyarylalkylsiloxanes, polyether siloxanes or silicone resins.

The skin cosmetic or dermatological preparations are prepared by customary processes known to the person skilled in the art.

Preferably, the skin cosmetic and dermatological compositions are in the form of emulsions, in particular water-in-oil (W/O) or oil-in-water (O/W) emulsions. It is, however, also possible to choose other types of formulations, for example hydrodispersions, gels, oils, oleogels, multiple emulsions, for example in the form of W/O/W or O/W/O emulsions, anhydrous ointments or ointment bases, etc.

Emulsions are prepared by known methods. Besides at least one polymer A, the emulsions generally comprise customary constituents, such as fatty alcohols, fatty acid esters and, in particular, fatty acid triglycerides, fatty acids, lanolin and derivatives thereof, natural or synthetic oils or waxes and emulsifiers in the presence of water. The choice of additives specific to the type of emulsion and the preparation of suitable emulsions is described, for example, in Schrader, Grundlagen and Rezepturen der Kosmetika [Fundamentals and formulations of cosmetics], Hüthig Buch Verlag, Heidelberg, 2nd edition, 1989, third part, which is hereby expressly incorporated by reference.

A suitable emulsion, e.g. for a skin cream etc., generally comprises an aqueous phase which is emulsified in an oil or fatty phase using a suitable emulsifier system.

The amount of emulsifier system in this type of emulsion is preferably from about 4 to 35% by weight, based on the total weight of the emulsion. Preferably, the amount of fatty phase is about 20 to 60% by weight. Preferably, the amount of aqueous phase is about 20 and 70%, in each case based on the total weight of the emulsion. The emulsifiers are those which are usually used in this type of emulsion. They are chosen, for example, from: $C_{12}$-$C_{18}$-sorbitan fatty acid esters; esters of hydroxystearic acid and $C_{12}$-$C_{18}$-fatty alcohols; mono- and diesters of $C_{12}$-$C_{18}$-fatty acids and glycerol or polyglycerol; condensates of ethylene oxide and propylene glycols; oxypropylenated/oxyethylated $C_{12}$-$C_{18}$-fatty alcohols; polycyclic alcohols, such as sterols; aliphatic alcohols with a high molecular weight, such as lanolin; mixtures of oxypropylenated/polyglycerylated alcohols and magnesium isostearate; succinic esters of polyoxyethylenated or polyoxypropylenated fatty alcohols; and mixtures of magnesium, calcium, lithium, zinc or aluminum lanolate and hydrogenated lanolin or lanolin alcohol.

Preferred fat components which may be present in the fatty phase of the emulsions are: hydrocarbon oils, such as paraffin oil, Purcellin oil, perhydrosqualene and solutions of microcrystalline waxes in these oils; animal or vegetable oils, such as sweet almond oil, avocado oil, calophylum oil, lanolin and derivatives thereof, castor oil, sesame oil, olive oil, jojoba oil, karite oil, hoplostethus oil; mineral oils whose distillation start-point under atmospheric pressure is at about 250° C. and whose distillation end-point is at 410° C., such as, for example, vaseline oil; esters of saturated or unsaturated fatty acids, such as alkyl myristates, e.g. isopropyl, butyl or cetyl myristate, hexadecyl stearate, ethyl or isopropyl palmitate, octanoic or decanoic acid triglycerides and cetyl ricinoleate.

The fatty phase can also comprise silicone oils which are soluble in other oils, such as dimethylpolysiloxane, methylphenylpolysiloxane and the silicone glycol copolymer, fatty acids and fatty alcohols.

In order to favor the retention of oils, besides the polymers A it is also possible to use waxes, such as, for example, carnauba wax, candelilla wax, beeswax, microcrystalline wax, ozokerite wax and Ca, Mg and Al oleates, myristates, linoleates and stearates.

In general, the water-in-oil emulsions are prepared by adding the fatty phase and the emulsifier to a mixing container. This is heated at a temperature of from about 50 to 75° C., then the active ingredients and/or auxiliaries which are soluble in oil are added, and water which has been heated beforehand to approximately the same temperature and in which, if appropriate, the water-soluble ingredients have been dissolved beforehand is added, with stirring. The mixture is stirred until an emulsion of the desired fineness is obtained and is then left to cool to room temperature, if appropriate with less stirring.

In addition, a care emulsion according to the invention can be in the form of an O/W emulsion. Such an emulsion usually comprises an oil phase, emulsifiers which stabilize the oil phase in the water phase, and an aqueous phase which is usually present in thickened form.

The aqueous phase of the O/W emulsion of the preparations according to the invention comprises, if appropriate:
  alcohols, diols or polyols, and ethers thereof, preferably ethanol, isopropanol, propylene glycol, glycerol, ethylene glycol monoethyl ether;
  customary thickeners and gel formers, such as, for example, crosslinked polyacrylic acids and derivatives thereof, polysaccharides, such as xanthan gum or alginates, carboxymethylcellulose or hydroxycarboxymethylcellulose, fatty alcohols, polyvinyl alcohol and polyvinylpyrrolidone.

The oil phase comprises oil components customary in cosmetics, such as, for example:
  esters of saturated and/or unsaturated, branched and/or unbranched $C_3$-$G_{30}$-alkanecarboxylic acids and saturated and/or unsaturated, branched and/or unbranched $C_3$-$C_{30}$-alcohols, of aromatic carboxylic acids and saturated and/or unsaturated, branched and/or unbranched $C_3$-$C_{30}$-alcohols, for example isopropyl myristate, isopropyl stearate, hexyldecyl stearate, oleyl oleate; also synthetic, semisynthetic and natural mixtures of such esters, such as jojoba oil;
  branched and/or unbranched hydrocarbons and hydrocarbon waxes;
  silicone oils, such as cyciomethicone, dimethylpolysiloxane, diethylpolysiloxane, octamethylcyclotetrasiloxane, and mixtures thereof;
  dialkyl ethers;
  mineral oils and mineral waxes;
  triglycerides of saturated and/or unsaturated, branched and/or unbranched $C_8$-$C_{24}$-alkanecarboxylic acids; they can be chosen from synthetic, semisynthetic or natural oils, such as olive oil, palm oil, almond oil or mixtures.

Suitable emulsifiers are, preferably, O/W emulsifiers, such as polyglycerol esters, sorbitan esters or partially esterified glycerides.

The preparation can take place by melting the oil phase at about 80° C.; the water-soluble constituents are dissolved in hot water, added to the oil phase slowly and with stirring; homogenized and stirred until cold.

The nonlimiting examples below serve to illustrate the subject matter of the invention in more detail.

Measurement Methods

Determination of the K Value

The K values are measured in accordance with Fikentscher, Cellulosechemie, Vol. 13, p. 58 to 64 (1932) at 25° C. in N-methylpyrrolidone (NMP) solution and are a measure of the molecular weight. The NMP solution of the polymers comprises 1 g of polymer in 100 ml of solution.

If the polymers are in the form of aqueous dispersions, corresponding amounts of the dispersion are topped up with NMP to 100 ml depending on the polymer content of the dispersion, so that the concentration of 1 g of polymer in 100 ml of solution arise.

The K value is measured in a micro-Ubbelohde capillary type M Ic from Schott.

Determination of the Droplet Size Distribution (PSD) by Means of Malvern® Scattered Light Analysis The droplet size distribution was determined using particle size measurement system for detecting liquid aerosols "Malvern®Master Sizer X" (Malvern instruments Inc., Southborough Mass., USA).

Measurement Principle:

The measurement system is based on the method of laser light diffraction at the particle, which is suitable not only for spray analysis (aerosols, pump sprays), but also for determining the size of solids, suspensions and emulsions in the size range from 0.1 μm to 2000 μm.

A particle collective (=droplet) is illuminated by a laser. At each droplet, some of the incident laser light is scattered. This light is captured on a multielement detector and the corresponding light energy distribution is determined. This data is used to calculate the corresponding particle distribution using the evaluation software.

Procedure:

The aerosols were sprayed at a distance of 29.5 cm from the laser beam. The spray cone was at right angles to the laser beam.

Before each measurement, the aerosol cans were attached to a firmly installed holding device, thus meaning that all of the aerosols to be tested were measured at exactly the same distance.

Before the actual particle measurement, a "background measurement" was carried out. By doing so, the effects of dust and other contaminants within the measurement range were eliminated.

The aerosol was then sprayed into the test space. The entire particle volume was detected for a test period of 2 s and evaluated.

Evaluation:

The evaluation comprises a tabular depiction over 32 class widths from 0.5 μm to 2000 μm and additionally a graphical depiction of the particle size distribution.

Since the spray experiments are an approximately uniform distribution, the mean diameter D (v, 0.5) is given. This numerical value indicates that 50% of the total particle volume measured is below this value.

For readily sprayable aerosol systems in the cosmetics sector, this value is in the range from 30 μm to 80 μm, depending on the polymer content, geometry of the valve and actuator, solvent ratio and amounts of propellant gas.

Determination of the Setting (Flexural Rigidity):

The setting of polymeric film formers was measured not only by a subjective assessment, but also objectively physically as flexural rigidity of thin hair swatches which have been treated with the polymer solution and dried again. Here, a force transducer determines the force required for bending while the overall measurement proceeds under standardized conditions in a climatically controlled room at 65% relative atmospheric humidity.

To measure the flexural rigidity, 3.0% strength by weight solutions of the polymers according to the invention were prepared. The measurement of the flexural rigidity was carried out on 5 to 10 hair swatches (each about 3 g and 24 cm in length) at 20° C. and 65% relative humidity. The weighed, dry hair swatches were dipped into the 3.0% strength by weight polymer solution, where, through triple immersion and removal, then carefully squeezed by squeezing between filter paper. Uniform distribution was then ensured. The excess film-former solution was then stripped out between thumb and forefinger and the hair swatches were shaped by hand so that they had a round cross section.

They were dried overnight in the climatically controlled room at 20° C. and 65% relative humidity.

The tests were carried out in a climatically controlled room at 20° C. and 65% relative humidity using a stress/strain testing device. The hair swatch was placed symmetrically on two cylindrical rolls of the sample holder. In exactly the middle, the swatch was then bent from above using a rounded punch 40 mm (breakage of the polymer film). The force required for this was measured using a weighing cell (50 N) and given in Newton. The values ascertained in this way were placed in relation to those for a standard commercial comparison polymer (Amphomer®LV-71 as standard 100%, as indicated).

Determination of the Ability to be Washed Out:

A hair swatch treated with polymer analogously to the determination of the setting was washed in a ca. 37° C.-hot Texapon®NSO solution (6 ml of Texapon®NSO (28% strength) in 1 l of warm water) for ca. 15 seconds by dipping it in and squeezing it five times. The hair swatch was then rinsed until clear and treated again in the same way. The hair swatch was then squeezed thoroughly on filter paper and left to dry overnight. The dry hair swatch was put in rollers and analyzed for residues.

Determination of the Curl Retention

Basic Formulation: (without 10% Propellant Gas)

2.0% by weight of active ingredient of polymer to be tested
2.0% by weight of Luviquat®Mono LS
0.2% by weight of perfume oil
0.1% by weight of Euxyl®K 100
ad 90.0% by weight of demineralized water.

For each polymer to be tested, 180 g of such a solution were prepared. To determine the curl retention, hair swatches ca. 2 g in weight and 15.5 cm in length and comprising mid-brown, Caucasian human hair were used.

Treatment of the Hair Swatches:

The hair swatches were washed twice with an aqueous Texapon®NSO solution. The hair swatches were then rinsed with warm water until no more foaming was evident and after-rinsed with demineralized water, combed and laid to dry on filter paper placed on filter paper to dry. Before the measurement, the hair swatches were stored in cold demineralized water for about 1 hour.

The wet hair swatch was pressed between filter paper, dipped into the polymer solution (see above), squeezed with the fingers and pressed again between filter paper. This process was carried out a total of three times.

The hair was then wound around a Teflon rod 12 mm in diameter and fastened using filter paper and rubber bands. The hair swatches were then dried in the heating cabinet for 90 min at 70-80° C. After cooling to room temperature, the curls were slipped off while retaining the shape and hung up on a frame and the curl length ($L_0$) was determined.

To determine a curl retention value, 5 hair curls were used. The curls were suspended in a climatically controlled chamber at 20° C. and 75% or 90% relative atmospheric humidity. After 5 hours, the length ($L_t$) was read off.

The curl retention is calculated as follows:

$$\text{Curl Retention in \%} = \frac{L - L_t}{L - L_0} * 100$$

L=Length of the hair (15.5 cm)
$L_0$=Length of the hair curl after drying
$L_t$=Length of the hair curl after climatic treatment The mean value from the 5 individual measurements after 5 h at 20° C. and 75% or 90% relative humidity is given as curl retention.

Determination of the Stickiness

Firstly, a clear, 20% strength by weight ethanolic or ethanolic/aqueous solution of the polymer to be characterized is prepared. In order to obtain a clear solution it is if appropriate necessary to neutralize the polymer. A doctor knife (120 μm slit width) is then used to apply a film of the polymer from the ethanolic or ethanolic/aqueous solution on a glass plate. This rectangular glass plate has a length of ca. 20 cm and a width of ca. 6.5 m. The polymer film applied thereto has in each case a length of ca. 16 to 18 cm and a width of ca. 5.5 cm.

The film is then dried in the air for ca. 10 hours and then stored in the climatically controlled cabinet for a further 12 hours at 20° C. and 80% relative humidity.

Then, under these conditions, in the climatically controlled cabinet, a plastic carbon ribbon (e.g. Pelikan® 2060, 50 mm wide) located on a round rubber punch (diameter 400 mm, Shore A hardness 60±5) was pressed onto the polymer film with a force of about 250 N for 10 seconds.

The amount of black pigment which remains adhering to the polymer film after the punch has been removed corresponds to the stickiness of the film. A visual assessment of the black coloration of the film was made. The assessment scale ranges from 0 to 5, where 0 is not sticky and 5 is very considerably sticky.

Determination of the Appearance of the Aerosol Formulation

The preparation comprising 5% by weight of the particular polymer neutralized with AMP, 40% by weight of DME, 15% by weight of ethanol and 40% by weight of water were poured into a transparent glass aerosol container. The propellant gas was added and the clarity of the resulting liquid/propellant gas mixture was then assessed visually.

EXAMPLES

The following examples illustrate the invention without limiting it.

Abbreviations used:
t-BA Tert-butyl acrylate
MAA Methacrylic acid
AA Acrylic acid
ITS Itaconic acid
EA Ethyl acrylate
MMA Methyl methacrylate
EMA Ethyl methacrylate
t-BMA Tert-butyl methacrylate
i-BMA Isobutyl methacrylate
CD completely demineralized Preparation of Urethane Acrylate c26 (Component c)

672.0 g of a polyester of adipic acid and neopentyl glycol with an OH number of about 200, 140.0 g of hydroxyethyl acrylate, 0.6 g of hydroquinone monomethyl ether, 1.20 g of 2,6-di-tert-butyl-4-methylphenol, 0.12 g of tetrabutyl orthotitanate were initially introduced into a round-bottomed flask and heated to 50° C. 400.0 g of isophorone diisocyanate were then added dropwise over the course of 30 minutes. The mixture was left to react for a further 7 hours at 90-95° C., during which the NCO content dropped to 0.56%. The mixture was cooled to 60° C., then 520.0 g of ethanol were added and the mixture was left to react further for about 2 hours at 65-70° C. until the isocyanate content (NCO value) had dropped to 0. The resulting resin was filtered over a 50 μm filter and bottled.

Preparation of Urethane Acrylate c27 (Component c)

672.0 g of a polyester of adipic acid and neopentyl glycol with an OH number of about 200, 140.0 g of hydroxyethyl acrylate, 0.6 g of hydroquinone monomethyl ether, 1.21 g of 2,6-di-tert-butyl-4-methylphenol, 0.12 g of cesium acetate were initially introduced into a round-bottomed flask and heated to 50° C. 400.0 g of isophorone diisocyanate were then added dropwise over the course of 30 minutes. The mixture was left to react for a further 7 hours at 90-95° C., during which the NCO content dropped to 0.56%. The mixture was cooled to 60° C., then 520.0 g of ethanol were added and the mixture was left to react further for about 2 hours at 65-70° C. until the isocyanate content (NCO value) had dropped to 0. The resulting resin was filtered over a 50 μm filter and bottled.

Preparation of Urethane Acrylate c28 (Component c)

672.0 g of a polyester of adipic acid and neopentyl glycol with an OH number of about 200, 140.0 g of hydroxyethyl acrylate, 0.6 g of hydroquinone monomethyl ether, 1.21 g of 2,6-di-tert-butyl-4-methylphenol were initially introduced into a round-bottomed flask and heated to 50° C. 400.0 g of isophorone diisocyanate were then added dropwise over the course of 30 minutes. The mixture was left to react for a further 20 hours at 90-95° C., during which the NCO content dropped to 0.1%. The mixture was cooled to 60° C., then 10.0 g of methanol were added and the mixture was left to react further for about 4 hours at 90-95° C. until the isocyanate content (NCO value) had dropped to 0. The resulting resin was mixed at room temperature with 510.0 g of tripropylene glycol diacrylate and filtered over a 50 μm filter and bottled.

I. Polymers A: Preparation and Characterization

Polymer 10:

| Feed 1 | 109.50 g | methyl methacrylate |
|---|---|---|
|  | 22.50 g | methacrylic acid |
|  | 15.00 g | acrylic acid |
|  | 3.00 g | Laromer ® UA 19 T |
|  | 100.00 g | ethanol cosm. |
| Feed 2 | 2.25 g | Wako ® V 59 |
|  | 50.00 g | ethanol cosm. |

As initial charge, 37.50 g of feed 1 and 13.13 g of feed 2 were mixed with 150.00 g of cosmetic ethanol in a 1 l glass reactor. This initial charge was heated to reflux under a nitrogen atmosphere. After the reflux temperature had been reached, the feeds 1 and 2 were started together. Feed 1 was metered in over 3 hours under reflux and feed 2 was metered in over 4 hours under reflux. The reaction mixture was further polymerized under reflux for 1 hour. Feed 3 (0.68 g of Wako®V 59 and 50.00 g of ethanol cosm.) was then metered in over 30 minutes and the mixture was after-polymerized under reflux for 3 hours.

Polymer 12:

| Feed 1 | 117.00 g | methyl methacrylate |
|---|---|---|
|  | 15.00 g | methacrylic acid |
|  | 15.00 g | acrylic acid |
|  | 3.00 g | Laromer ® UA 19 T |
|  | 100.00 g | ethanol cosm. |
| Feed 2 | 3.00 g | Wako ® V 50 |
|  | 50.00 g | CD water |

As initial charge, 37.50 g of feed 1 and 13.1 g of feed 2 were mixed with 100.00 g of cosmetic ethanol in a 1 l glass reactor. This initial charge was heated to reflux under a nitrogen atmosphere. After the reflux temperature had been reached, the feeds 1 and 2 were started together. Feed 1 was metered in over 3 hours and feed 2 was metered in over 3.5 hours. The reaction mixture was further polymerized under reflux for 1 hour. Feed 3 (0.60 g of Wako®V 50 and 25.00 g of CD water) was then metered in over 30 minutes and the mixture was after-polymerized under reflux for 1.5 hours. Feed 4 (0.60 g of Wake®V-50 and 25.00 g of CD water) was then metered in over 30 minutes and the mixture was again after-polymerized under reflux for 1.5 hours.

Polymer 13:

| Feed 1 | 109.50 g | methyl methacrylate |
|---|---|---|
|  | 30.00 g | methacrylic acid |
|  | 7.50 g | acrylic acid |
|  | 3.00 g | Laromer ® UA 19 T |
|  | 122.50 g | ethanol cosm. |
| Feed 2 | 3.75 g | Wako ® V 50 |
|  | 18.00 g | CD water |

As initial charge, 13.6 g of feed 1 and 1.1 g of feed 2 were mixed with 39.90 g of cosmetic ethanol and 82.10 g of CD water in a 1 liter glass reactor. This initial charge was heated to 30° C. under a nitrogen atmosphere. After the reflux temperature had been reached, the feeds 1 and 2 were started together. Feed 1 was metered in under reflux over 3 hours and feed 2 was metered in under reflux over 4 hours. The reaction mixture was further polymerized under reflux for 2 hours. Feed 3 (0.75 g of tert-butyl perpivalate and 43.75 g of ethanol cosm.) was then metered in over 30 minutes and the mixture was after-polymerized under reflux for 2 hours. Feed 4 (0.75 g of tert-butyl perpivalate and 43.75 g of ethanol cosm.) was then metered in over 30 minutes and the mixture was after-polymerized again under reflux for 2 hours.

Polymer 15:

| Feed 1 | 109.50 g | methyl methacrylate |
|---|---|---|
|  | 30.00 g | methacrylic acid |
|  | 7.50 g | acrylic acid |
|  | 100.00 g | ethanol cosm. |
| Feed 2 | 3.00 g | Laromer ® UA 19 T |
|  | 22.50 g | ethanol cosm. |
| Feed 3 | 3.75 g | Wako ® V-50 |
|  | 22.50 g | CD water |

As initial charge, 12.3 g of feed 1 and 1.1 g of feed 3 were mixed with 39.90 g of cosmetic ethanol and 82.10 g of CD water in a 1 liter glass reactor. This initial charge was heated to reflux under a nitrogen atmosphere. After the reflux temperature had been reached, the feeds 1, 2 and 3 were started together. Feeds 1 and 2 were metered in under reflux over 3 hours and feed 3 was metered in under reflux over 4 hours. The reaction mixture was further polymerized under reflux for 2 hours. Feed 4 (0.75 g of tert-butyl perpivalate and 43.75 g of ethanol cosm.) was then metered in over 30 minutes and the mixture was after-polymerized under reflux for 2 hours. Feed 5 (0.75 g of tert-butyl perpivalate and 43.75 g of ethanol cosm.) was then metered in over 30 minutes and the mixture was after-polymerized again under reflux for 2 hours.

Polymer 16:

| Feed 1 | 234.0 g | methyl methacrylate |
|---|---|---|
|  | 30.00 g | methacrylic acid |
|  | 30.00 g | acrylic acid |
|  | 100.00 g | ethanol cosm. |
|  | 6.00 g | urethane acrylate c26 |
| Feed 2 | 6.0 g | Wako ® V-59 |
|  | 412.50 g | ethanol cosm. |
|  | 68.40 | CD water |

As initial charge, 15.0 g of feed 1 and 24.3 g of feed 2 were mixed with 171.50 g of cosmetic ethanol and 28.60 g of CD water in a 2 l glass reactor. This initial charge was heated to reflux under a nitrogen atmosphere. After the reflux temperature had been reached, the feeds 1 and 2 were started together. Feed 1 was metered in under reflux over 3 hours and feed 2 was metered in under reflux over 4 hours. The reaction mixture was further polymerized under reflux for 2 hours. Feed 3 (1.50 g of tert-butyl perpivalate, 3.0 g of CD water and 17.0 g of ethanol cosm.) was then metered in over 30 minutes and the mixture was after-polymerized under reflux for 2 hours. Feed 4 (1.50 g of tert-butyl perpivalate, 3.0 g of CD water and 17.0 g of ethanol cosm.) was then metered in over 30 minutes and the mixture was after-polymerized again under reflux for 2 hours.

Polymer 17:

| Feed 1 | 234.0 g | methyl methacrylate |
|---|---|---|
|  | 30.00 g | methacrylic acid |
|  | 30.00 g | acrylic acid |
|  | 6.00 g | urethane acrylate c26 |
| Feed 2 | 6.0 g | Wako ® V-59 |
|  | 412.50 g | ethanol cosm. |

As initial charge, 15.0 g of feed 1 and 21.0 g of feed 2 were mixed with 171.50 g of cosmetic ethanol and 103.0 g of CD water in a 2 l glass reactor. This initial charge was heated to reflux under a nitrogen atmosphere. After the reflux temperature had been reached, the feeds 1 and 2 were started together. Feed 1 was metered in under reflux over 3 hours and feed 2 was metered in under reflux over 4 hours. The reaction mixture was further polymerized under reflux for 2 hours. Feed 3 (1.50 g of tert-butyl perpivalate and 17.0 g of ethanol cosm.) was then metered in over 30 minutes and the mixture was after-polymerized under reflux for 2 hours. Feed 4 (1.50 g of tert-butyl perpivalate and 17.0 g of ethanol cosm.) was then metered in over 30 minutes and the mixture was after-polymerized again under reflux for 2 hours.

Unless indicated otherwise, the percentages are percent by weight. The preparation of the polymers 1-9 and 11 in the table below was carried out analogously to the above-described preparation of polymer 10. The preparation of polymers 14, 18, 19 and 20 was carried out analogously to the above-described preparation of polymer 15.

| Polymer | (Meth)acrylate % by wt. | MAA % by wt. | AA % by wt. | Component c) % by wt. | K value [1% in NMP] |
|---|---|---|---|---|---|
| 1 | MMA 75 | 10 | 10 | Ebecryl ® CL 1039 5 | 31.2 |
| 2 | EMA 75 | 10 | 10 | Ebecryl ® CL 1039, 5 | 30.3 |
| 3 | MMA 75 | 10 | 10 | Monomer C22 5 | 31.7 |
| 4 | EMA 75 | 10 | 10 | Monomer C22 5 | 31.6 |
| 5 | MMA 78 | 10 | 10 | Laromer ® UA 19T 2 | 36.4 |
| 6 | EMA 78 | 10 | 10 | Laromer ® UA 19T 2 | 34.5 |
| 7 | MMA 70 | — | 25 | Monomer C22 5 | 35.8 |
| 8 | EMA 70 | 15 | 10 | Monomer C22 5 | 31.7 |
| 9 | MMA 72 | 15 | 10 | Ebecryl ® CL 1039 3 | 31.6 |
| 10 | MMA 73 | 15 | 10 | Laromer ® UA 19T 2 | 37.1 |
| 11 | MMA 74 | 15 | 10 | Plex 6661-0 ® 1 | 35.8 |
| 12 | MMA 78 | 10 | 10 | Laromer ® UA 19T 2 | 34.1 |
| 13 | MMA 73 | 20 | 5 | Laromer ® UA 19T 2 | 30.5 |
| 14 | MMA 78 | 10 | 10 | Laromer ® UA 19T 2 | 32.2 |
| 15 | MMA 73 | 20 | 5 | Laromer ® UA 19T 2 | 31.6 |
| 16 | MMA 78 | 10 | 10 | urethane acrylate c26 2 | 33.2 |
| 17 | MMA 78 | 10 | 10 | urethane acrylate c26 2 | 34.0 |
| 18 | MMA 73 | 20 | 5 | Photomer ® 6891, 2 | 32.0 |
| 19 | MMA 73 | 20 | 5 | Sartomer ® CN981, 2 | 30.5 |
| 20 | MMA 74 | 20 | 5 | Ebecryl ® 265, 1 | — |

Application Properties of the Polymers According to the Invention

| Polymer | Appearance of aerosol | Setting, relative to Amphomer ® LV 71 [%] | Particle size upon spraying a VOC 55 aerosol [mm][a] | Curl Retention [%] | Ability to be washed out | Stickiness (Kempf) |
|---|---|---|---|---|---|---|
| 1 | clear | 88 | 39 | 64 | good | 0 |
| 2 | clear | 89 | 50 | 52 | good | 0 |
| 5 | clear | 106 | 41 | 60 | good | 0 |
| 6 | clear | 108 | 53 | 62 | good | 0 |
| 7 | clear | 97 | 37 | 35 | still good | 2 |
| 8 | clear | 83 | 51 | 66 | still good | 0-1 |
| 9 | clear | 115 | 50 | 78 | good | 0-1 |
| 10 | slightly cloudy | 105 | 42 | 57 | good | 0 |
| 11 | clear | 115 | 39 | 65 | still good | 0 |
| 12 | clear | 125 | 39 | 74 | very good | 0 |
| 13 | clear | 116 | 35 | 74 | good | 1 |
| 14 | almost clear | 114 | 34 | 58 | good | 0 |
| 15 | almost clear | 109 | 35 | 71 | good | 0 |
| 16 | almost clear | 104 | 36 | 89 | good | 0 |
| 17 | almost clear | 108 | 37 | 92 | good | 0 |
| 18 | blue-tinged | 83 | 32 | 75 | still good | 0-1 |
| 19 | blue-tinged | 75 | 34 | 62 | still good | 0 |
| 20 | almost clear | 84 | 33 | 69 | still good | 0 |

[a] VOC 55 Aerosol: 5% of the respective polymer, neutralized completely with AMP, 40% of DME, 15% of ethanol, 40% of water;
Spray device:
Spray head: Kosmos .020D Wirbel .018" 21-6443-20,
Valve: DPV 33876 (Precision Valve)

II) Application Examples

Unless stated otherwise, all of the polymers containing acid groups used are 100% neutralized with AMP. "Water ad 100" means that the amount of water necessary to reach a total amount of 100% by weight is added to the particular preparation.

The quantitative data % are % by weight unless determined in some other way.

The abbreviation "q.s." means "quantum satin", i.e. add as much of an ingredient as is necessary to achieve a desired effect.

Example 1

VOC 55 Aerosol Hairspray

|  | [%] |
|---|---|
| Polymer from example no. 1 (solid) | 5.00 |
| Dimethyl ether | 40.00 |
| Ethanol | 15.00 |
| Water | ad 100 |

Further additives: silicone, perfume, antifoam, UV absorber

The example can be repeated in each case with the polymers 2 to 20 according to the invention. In each case, a VOC 55 aerosol hairspray with good properties is obtained.

Example 2

VOC 55 Aerosol Hairspray

|  | [%] |
|---|---|
| Polymer from example No. 1 (solid) | 5.00 |
| Dimethyl ether | 35.00 |
| Propane/butane | 5.00 |
| Ethanol | 15.00 |
| Water | ad 100 |

Further additives: silicone, perfume, antifoam, UV absorber

The example can be repeated in each case with the polymers 2 to 20. In each case, a VOC 55 aerosol hairspray with good properties is obtained.

Example 3

Aerosol Hairspray with Fluorocarbon Propellants

|  | [%] |
|---|---|
| Polymer from example No. 1 (solid) | 5.00 |
| Ethanol abs. | ad 100 |
| HFC 152A | 40.00 |

Further additives: silicone, perfume, antifoam, UV absorber

The example can be repeated in each case with the polymers 2 to 20. In each case, a low-VOC aerosol hairspray with good properties is obtained.

Example 4

Aerosol Hairspray with Fluorocarbon Propellants

|  | [%] |
|---|---|
| Polymer from example No. 1 (solid) | 5.00 |
| Dist. water | ad 100 |
| HFC 152A | 10.00 |
| Dimethyl ether | 30.00 |
| Ethanol abs. | 30.00 |

Further additives: silicone, perfume, antifoam, UV absorber

The example can be repeated in each case with the polymers 2 to 20. In each case, a low-VOC aerosol hairspray with good properties is obtained.

Example 5

VOC 55 Aerosol Hairspray

|  | [%] |
|---|---|
| Polymer from example No. 1 (solid) | 3.00 |
| Ultrahold ® Strong (solid, BASF) | 1.00 |
| Dimethyl ether | 40.00 |
| Ethanol | 15.00 |
| +AMP | to pH 8.3 |
| Water | ad 100 |

Further additive: silicone, perfume, antifoam

The example can be repeated in each case with the polymers 2 to 20 according to the invention. In each case, a VOC 55 aerosol hairspray with good properties is obtained.

Example 6

VOC 55 Aerosol Hairspray

|  | [%] |
|---|---|
| Polymer from example No. 1 (solid) | 3.00 |
| Luvimer ® Pro55 (solid, BASF) | 1.00 |
| Dimethyl ether | 40.00 |
| Ethanol | 15.00 |
| Water | ad 100 |

Further additive: silicone, perfume, antifoam

The example can be repeated in each case with the polymers 2 to 20 according to the invention. In each case, a VOC 55 aerosol hairspray with good properties is obtained.

Example 7

VOC 55 Aerosol Hairspray

|  | [%] |
|---|---|
| Polymer from example No. 1 (solid) | 3.00 |
| Luvimer ® P.U.R (solid, BASF) | 1.00 |
| Dimethyl ether | 40.00 |
| Ethanol | 15.00 |
| Water | ad 100 |

Further additive: silicone, perfume, antifoam

The example can be repeated in each case with the polymers 2 to 20 according to the invention. In each case, a VOC 55 aerosol hairspray with good properties is obtained.

Example 8

VOC 55 Aerosol Hairspray

|  | [%] |
|---|---|
| Polymer from example No. 1 (solid) | 3.00 |
| Resyn ® 28-2930 (solid, National Starch) | 1.00 |
| Dimethyl ether | 40.00 |
| Ethanol | 15.00 |
| Water | ad 100 |

Further additive: silicone, perfume, antifoam

The example can be repeated in each case with the polymers 2 to 20 according to the invention. A VOC 55 aerosol hairspray with good properties is likewise obtained.

Example 9

VOC 55 Aerosol Hairspray

|  | [%] |
|---|---|
| Polymer from example No. 1 (solid) | 2.00 |
| Stepanhold ® R-1*) (Stepan Chemical Co.) | 1.00 |
| Dimethyl ether | 40.00 |
| Ethanol | 15.00 |
| +AMP | to pH 8.3 |
| Water | ad 100 |

Further additive: silicone, perfume, antifoam
*)Stepanhold ® R-1 = poly(vinylpyrrolidone/ethyl methacrylate/methacrylic acid)

The example can be repeated in each case with the polymers 2 to 20 according to the invention. In each case, a VOC 55 aerosol hairspray with good properties is obtained.

Example 10

VOC 55 Hand Pump Spray

|  | [%] |
|---|---|
| Polymer from example No. 1 (solid) | 7.00 |
| Ethanol | 55.00 |
| Water | ad 100 |

Further additive: silicone, perfume, antifoam

The example can be repeated in each case with the polymers 2 to 20 according to the invention. In each case, a VOC 55 hand pump spray with good properties is obtained.

Example 11

VOC 80 Aerosol Hairspray

|  | [%] |
|---|---|
| Polymer from example No. 1 (solid) | 12.00 |
| Dimethyl ether | 40.00 |
| Ethanol | 40.00 |
| Water | ad 100 |

Further additive: silicone, perfume, antifoam

The example can be repeated in each case with the polymers 2 to 20 according to the invention. In each case, a VOC 80 aerosol hairspray with good properties is obtained.

Example 11

| Aqueous hand pump spray | [%] |
|---|---|
| Polymer from example No. 1 (solid) | 4.00 |
| Luviset ® Clear*) (solid) | 1.00 |
| Water | ad 100 |

Further additive: Water-soluble silicone, perfume, antifoam.
*)Luviset ® Clear: poly(vinylpyrrolidone/methacrylamide/vinylimidazole), BASF The example can be repeated in each case with the polymers 2 to 20 according to the invention. In each case, an aqueous hand pump spray with good properties is obtained.

Example 12

| Aqueous/ethanolic setting solution | [%] |
|---|---|
| Polymer from example No. 1 (solid) | 7.00 |
| Dist. water | ad 100 |
| Ethanol | 52.00 |

Further additive: silicone, perfume, antifoam

The example can be repeated in each case with the polymers 2 to 20 according to the invention. In each case, a setting lotion with good properties is obtained.

Example 13

| Ethanolic setting solution | [%] |
|---|---|
| Polymer from example No. 1 (solid) | 7.0 |
| Ethanol | ad 100 |

Further additive: silicone, perfume, antifoam . . .

The example can be repeated in each case with the polymers 2 to 20 according to the invention. In each case, a setting lotion with good properties is obtained.

Example 14

| Hair gel with Aculyn 28: | [%] |
|---|---|
| Phase 1: |  |
| Polymer from example No. 1 (solid) | 6.00 |
| Aminomethylpropanol (38% strength solution) | 1.0 |

-continued

| Water, dist. | ad 50 |
|---|---|
| Further additive: Preservative, soluble ethoxylated silicone, perfume ... | |
| Phase 2: | |
| Aculyn 28 (1% strength aqueous suspension) | 50.00 |

Preparation:
Phases 1 and 2 are weighed in separately and homogenized. Phase 2 is then slowly stirred into phase 1. An essentially clear, stable gel is formed.

The example can be repeated in each case with the polymers 2 to 20 according to the invention. In each case, a hair gel with Aculyn 28 with good properties is obtained.

Example 15

| Hair gel with hydroxyethylcellulose: | [%] |
|---|---|
| Phase 1: | |
| Polymer from example No. 1 (solid) | 6.00 |
| Water, dist. | ad 50 |
| Further additive: Preservative, soluble ethoxylated silicone, perfume | |
| Phase 2: | |
| Natrosol HR 250 (5% strength solution) | 50.00 |
| Hydroxyethylcellulose (Hercules) | |

Preparation:
Phases 1 and 2 are weighed in separately and homogenized. Phase 2 is then slowly stirred into phase 1. An essentially clear, stable gel is formed.

The example can be repeated in each case with the polymers 2 to 20 according to the invention. In each case, a hair gel with hydroxyethylcellulose with good properties is obtained.

Example 16

| Foam conditioner | [%] |
|---|---|
| Polymer from example No. 1 (solid) | 0.50 |
| Cremophor ® A 25 (Ceteareth 25/BASF) | 0.20 |
| Comperlan ® KD (coamide DEA/Henkel) | 0.10 |
| Propane/butane | 10.00 |
| Further additive: perfume, preservative | |
| Water | ad 100 |

Preparation:
Weigh in and dissolve with stirring. Bottle and add propellant gas.

The example can be repeated in each case with the polymers 2 to 20 according to the invention. In each case, a foam conditioner with good properties is obtained, Example 17

| Conditioner shampoo: | [%] |
|---|---|
| A) Texapon ® NSO 28% strength (sodium laureth sulfate/Henkel) | 50.00 |
| Comperlan ® KS (coamide DEA/Henkel) | 1.00 |
| Polymer from example No. 1 (solid) | 3.00 |
| q.s. Perfume oil | |
| B) Water | 44.5 |
| Sodium chloride | 1.5 |
| q.s. Preservative | |

Preparation:
Phases 1 and 2 are weighed in separately and homogenized. Phase 2 is then slowly stirred into phase 1. An essentially clear, stable gel is formed.

The example can be repeated in each case with the polymers 2 to 20 according to the invention. In each case, a conditioner shampoo with good properties is obtained.

Example 18

| Standard O/W cream: | | |
|---|---|---|
| | [%] | CTFA name |
| Oil phase: | | |
| Cremophor ® A6 | 3.5 | Ceteareth-6 (and) Stearyl Alcohol |
| Cremophor ® A25 | 3.5 | Ceteareth-25 |
| Glycerol monostearate s.e. | 2.5 | Glyceryl stearate |
| Paraffin oil | 7.5 | Paraffin Oil |
| Cetyl alcohol | 2.5 | Cetyl Alcohol |
| Luvitol ® EHO | 3.2 | Cetearyl Octanoate |
| Vitamin E acetate | 1.0 | Tocopheryl Acetate |
| Nip-Nip | 0.1 | Methyl- and Propyl-4-hydroxybenzoate (7:3) |
| Water phase: | | |
| Polymer from example No. 1 (solid) | 0.6 | |
| Water | 77.0 | |
| 1,2-Propylene glycol | 1.5 | propylene glycol |
| Germall II | 0.1 | Imidazolidinylurea |

Preparation:
The oil and water phases are weighed in separately and homogenized at a temperature of about 80° C. The water phase is then slowly stirred into the oil phase and slowly cooled to room temperature with stirring.

The example can be repeated in each case with the polymers 2 to 20 according to the invention. In each case, a standard O/W cream with good properties is obtained.

Example 19

Liquid Makeup

| | A |
|---|---|
| 1.70 | Glyceryl stearate |
| 1.70 | Cetyl alcohol |
| 1.70 | Ceteareth-6 |
| 1.70 | Ceteareth-25 |
| 5.20 | Caprylic/capric triglyceride |
| 5.20 | Mineral oil |
| | B |
| q.s. | Preservative |
| 4.30 | Propylene glycol |
| 2.50 | Polymer from example 1 (solid) |
| ad 100 | Dist. water |
| | C |
| q.s. | Perfume oil |
| | D |
| 2.00 | Iron oxide |
| 12.00 | Titanium dioxide |

Preparation:
Heat phase A and phase B separately from one another to 80° C. Then mix phase B into phase A using a stirrer. Allow everything to cool to 40° C. and add phase C and phase D. Homogenize again.

The example can be repeated in each case with the polymers 2 to 20 according to the invention. In each case, a liquid makeup with good properties is obtained.

Example 20

Oil-Free Makeup

| | A |
|---|---|
| 0.35 | Veegum |
| 5.00 | Butylene glycol |
| 0.15 | Xanthan gum |
| | B |
| 34.0 | Dist. water |
| q.s. | Preservative |
| 0.2 | Polysorbate-20 |
| 1.6 | Tetrahydroxypropylethylenediamine |
| | C |
| 1.0 | Silicon dioxide |
| 2.0 | Nylon-12 |
| 4.15 | Mica |
| 6.0 | Titanium dioxide |
| 1.85 | Iron oxide |
| | D |
| 4.0 | Stearic acid |
| 1.5 | Glyceryl stearate |
| 7.0 | Benzyl laurate |
| 5.0 | Isoeicosane |
| q.s. | Preservative |
| | E |
| 0.5 | Panthenol |
| 0.1 | Imidazolidinylurea |
| 5.0 | Polymer from example 1 (solid) |

Preparation:
Wet phase A with butylene glycol, add to phase B and mix well. Heat phase AB to 75° C. Pulverize phase C feed substances, add to phase AB and homogenize well. Mix feed substances of phase D, heat to 80° C. and add to phase ABC. Mix for some time until everything is homogeneous. Transfer everything to a vessel with propellor mixer. Mix the feed substances of phase E, add to phase ABCD and mix well.

The example can be repeated in each case with the polymers 2 to 20 according to the invention. In each case, an oil-free makeup with good properties is obtained.

Example 21

Shimmering Gel

| | A |
|---|---|
| 32.6 | Dist. water |
| 0.1 | Disodium EDTA |
| 25.0 | Natrosol (4% strength aqueous solution) |
| 0.3 | Preservative |
| | B |
| 0.5 | Dist. water |
| 0.5 | Triethanolamine |
| | C |
| 2.0 | Polymer from example 1 (solid) |
| ad 100 | Dist. water |
| 1.0 | Polyquaternium-46 (20% strength aqueous solution) |
| 5.0 | Iron oxide |
| | D |
| 15.0 | Dist. water |
| 1.0 | D-Panthenol 50 P (panthenol and propylene glycol) |

Preparation:
Using a propeller mixer, thoroughly mix the feed substances of phase A in the order given. Then add phase B to phase A. Stir slowly until everything is homogeneous. Thoroughly homogenize phase C until the pigments are well distributed. Add phase C and phase D to phase AB and mix well.

The example can be repeated in each case with the polymers 2 to 20 according to the invention. In each case, a shimmering gel with good properties is obtained.

Example 22

Sunscreen Gel

| | Phase A |
|---|---|
| 1.00 | hydrogenated castor oil-PEG-40 |
| 8.00 | Octyl methoxycinnamate (Uvinul ® MC 80) |
| 5.00 | Octocrylene (Uvinul ® N 539) |
| 0.80 | Octyl Triazone (Uvinul ® T 150) |
| 2.00 | Butyl Methoxydibenzoylmethane (Uvinul ® BMBM) |
| 2.00 | Tocopheryl acetate |
| q.s. | Perfume oil |
| | Phase B |
| 2.50 | Polymer from example 1 (solid) |
| ad 100 | Dist. water |
| 0.30 | Acrylate/$C_{10-30}$ alkyl acrylate copolymer |
| 0.20 | Carbomer |
| 5.00 | Glycerol |
| 0.20 | Disodium EDTA |
| q.s. | Preservative |
| 62.80 | Dist. water |
| | Phase C |
| 0.20 | Sodium hydroxide |

Preparation:
Mix the components of phase A. Allow phase B to swell and stir into phase A with homogenization. Neutralize with phase C and homogenize again.

The example can be repeated in each case with the polymers 2 to 20 according to the invention. In each case, a sunscreen gel with good properties is obtained.

Example 23

Sunscreen Emulsion with $TiO_2$ and $ZnO_2$

| | Phase A |
|---|---|
| 6.00 | hydrogenated castor oil-PEG-7 |
| 2.00 | PEG-45/Dodecyl Glycol Copolymer |
| 3.00 | Isopropyl myristate |
| 8.00 | Jojoba oil (*Buxus Chinensis*) |
| 4.00 | Octyl Methoxycinnamate (Uvinul ® MC 80) |
| 2.00 | 4-Methylbenzylidenecamphor (Uvinul ® MBC 95) |
| 3.00 | Titanium dioxide, dimethicone |
| 1.00 | Dimethicone |
| 5.00 | Zinc oxide, dimethicone |
| | Phase B |
| 2.0 | Polymer from example 1 (solid) |
| ad 100 | Dist. water |
| 0.20 | Disodium EDTA |
| 5.00 | Glycerol |

-continued

| | |
|---|---|
| q.s. | Preservative |
| 50.80 | Dist. water |
| | Phase C |
| q.s. | Perfume oil |

Preparation:
Heat phases A and B separately to about 85° C. Stir phase B into phase A and homogenize. Cool to about 40° C., add phase C and briefly homogenize again.

The example can be repeated in each case with the polymers 2 to 20 according to the invention. In each case, a sunscreen emulsion with $TiO_2$ and $ZnO_2$ with good properties is obtained.

Example 24

Sunscreen Lotion

| | |
|---|---|
| | Phase A |
| 6.00 | Octyl Methoxycinnamate (Uvinul ® MC 80) |
| 2.50 | 4-Methylbenzylidenecamphor (Uvinul ® MBC 95) |
| 1.00 | Octyl Triazone (Uvinul ® T 150) |
| 2.00 | Butyl Methoxydibenzoylmethane (Uvinul ® BMBM) |
| 2.00 | PVP/Hexadecene copolymer |
| 5.00 | PPG-3 Myristyl Ether |
| 0.50 | Dimethicone |
| 0.10 | BHT, ascorbyl palmitate, citric acid, glyceryl stearate propylene glycol |
| 2.00 | Cetyl alcohol |
| 2.00 | Potassium cetyl phosphate |
| | Phase B |
| 0.50 | Polymer from example 1 (solid) |
| ad 100 | Dist. water |
| 5.00 | Propylene glycol |
| 0.20 | Disodium EDTA |
| q.s. | Preservative |
| 63.92 | Dist. water |
| | Phase C |
| 5.00 | Mineral oil |
| 0.20 | Carbomer |
| | Phase D |
| 0.08 | Sodium hydroxide |
| | Phase E |
| q.s. | Perfume oil |

Preparation:
Heat phases A and B separately to about 80° C. Stir phase B into phase A with homogenization, briefly after-homogenize. Prepare a slurry from phase C, stir into phase AB, neutralize with phase D and after-homogenize. Cool to about 40° C., add phase E, homogenize again.

The example can be repeated in each case with the polymers 2 to 20 according to the invention. In each case, a sunscreen lotion with good properties is obtained.

Example 25

Peelable Face Mask

| | |
|---|---|
| | Phase A |
| 57.10 | Dist. water |
| 6.00 | Polyvinyl alcohol |
| 5.00 | Propylene glycol |
| | Phase B |

-continued

| | |
|---|---|
| 20.00 | Alcohol |
| 4.00 | PEG-32 |
| q.s | Perfume oil |
| | Phase C |
| 5.00 | Polyquaternium-44 |
| 0.50 | Polymer from Example 1 (solid) |
| ad 100 | Dist. water |
| 0.20 | Allantoin |

Preparation:
Heat phase A to at least 90° C. and stir until dissolved. Dissolve phase B at 50° C. and stir into phase A. At about 35° C., compensate for the loss of ethanol. Add phase C and stir in.

The example can be repeated in each case with the polymers 2 to 20 according to the invention. In each case, a peelable face mask with good properties is obtained.

Example 26

Face Mask

| | |
|---|---|
| | Phase A |
| 3.00 | Ceteareth-6 |
| 1.50 | Ceteareth-25 |
| 5.00 | Cetearyl alcohol |
| 6.00 | Cetearyl octanoate |
| 6.00 | Mineral oil |
| 0.20 | Bisabolol |
| 3.00 | Glyceryl stearate |
| | Phase B |
| 2.00 | Propylene glycol |
| 5.00 | Panthenol |
| 2.50 | Polymer from Example 1 (solid) |
| ad 100 | Dist. water |
| q.s. | Preservative |
| 53.80 | Dist. water |
| | Phase C |
| q.s. | Perfume oil |
| 0.50 | Tocopheryl acetate |

Preparation:
Heat phases A and B separately to about 80° C. Stir phase B into phase A with homogenization, briefly after-homogenize. Cool to about 40° C., add phase C, homogenize again.

The example can be repeated in each case with the polymers 2 to 20 according to the invention. In each case, a face mask with good properties is obtained.

Example 27

Body Lotion Foam

| | |
|---|---|
| | Phase A |
| 1.50 | Ceteareth-25 |
| 1.50 | Ceteareth-6 |
| 4.00 | Cetearyl alcohol |
| 10.00 | Cetearyl octanoate |
| 1.00 | Dimethicone |
| | Phase B |
| 0.50 | Polymer from Example 1 (solid) |
| ad 100 | Dist. water |
| 2.00 | Panthenol |
| 2.50 | Propylene glycol |

-continued

| | |
|---|---|
| q.s. | Preservative |
| 74.50 | Dist. water |
| | Phase C |
| q.s. | Perfume oil |

Preparation:
Heat phases A and B separately to about 80° C. Stir phase B into phase A and homogenize. Cool to about 40° C., add phase C and briefly homogenize again. Bottling: 90% active substance and 10% propane/butane at 3.5 bar (20° C.).

The example can be repeated in each case with the polymers 2 to 20 according to the invention. In each case, a body lotion foam with good properties is obtained.

Example 28

Face Tonic for Dry and Sensitive Skin

| | Phase A |
|---|---|
| 2.50 | hydrogenated castor oil-PEG-40 |
| q.s. | Perfume oil |
| 0.40 | Bisabolol |
| | Phase B |
| 3.00 | Glycerol |
| 1.00 | Hydroxyethylcetyldimonium phosphate |
| 5.00 | Witch hazel (*Hamamelis Virginiana*) distillate |
| 0.50 | Panthenol |
| 0.1 | Polymer from Example 1 (solid) |
| ad 100 | Dist. water |
| q.s. | Preservative |
| 87.60 | Dist. water |

Preparation:
Dissolve phase A to give a clear solution. Stir phase B into phase A.

The example can be repeated in each case with the polymers 2 to 20 according to the invention. In each case, a face tonic for dry and sensitive skin with good properties is obtained.

Example 29

Face Washing Paste with Peeling Effect

| | Phase A |
|---|---|
| 58.00 | Dist. water |
| 2.50 | Polymer from Example 1 (solid) |
| ad 100 | Dist. water |
| 1.50 | Carbomer |
| q.s. | Preservative |
| | Phase B |
| q.s. | Perfume oil |
| 7.00 | Potassium Cocoyl Hydrolyzed Protein |
| 4.00 | Cocamidpropylbetaine |
| | Phase C |
| 1.50 | Triethanolamine |
| | Phase D |
| 13.00 | Polyethylene (Luwax ® A) |

Preparation:
Allow phase A to swell. Dissolve phase B to give a clear solution. Stir phase B into phase A. Neutralize with phase C. Then stir in phase D.

The example can be repeated in each case with the polymers 2 to 20 according to the invention. In each case, a face washing paste with peeling effect with good properties is obtained.

Example 30

Face Soap

| | Phase A |
|---|---|
| 25.0 | Potassium cocoate |
| 20.0 | Disodium Cocoamphodiacetate |
| 2.0 | Lauramide DEA |
| 1.0 | Glycol stearate |
| 0.50 | Polymer from Example 1 (solid) |
| ad 100 | Dist. water |
| 50.0 | Dist. water |
| q.s. | Citric acid |
| | Phase B |
| q.s. | Preservative |
| q.s. | Perfume oil |

Preparation:
Heat phase A to 70° C. with stirring until everything is homogeneous. Adjust pH to 7.0-7.5 with citric acid, allow everything to cool to 50° C. and add phase B.

The example can be repeated in each case with the polymers 2 to 20 according to the invention. In each case, a face soap with good properties is obtained.

Example 31

Face Cleansing Milk, O/W Type

| | Phase A |
|---|---|
| 1.50 | Ceteareth-6 |
| 1.50 | Ceteareth-25 |
| 2.00 | Glyceryl stearate |
| 2.00 | Cetyl alcohol |
| 10.00 | Mineral oil |
| | Phase B |
| 5.00 | Propylene glycol |
| q.s. | Preservative |
| 1.0 | Polymer from Example 1 (solid) |
| ad 100 | Dist. water |
| 62.30 | Dist. water |
| | Phase C |
| 0.20 | Carbomer |
| 10.00 | Cetearyl octanoate |
| | Phase D |
| 0.40 | Tetrahydroxypropylethylenediamine |
| | Phase E |
| q.s. | Perfume oil |
| 0.10 | Bisabolol |

Preparation:
Heat phases A and B separately to about 80° C. Stir phase B into phase A with homogenization, briefly after-homogenize. Prepare a slurry from phase C, stir into phase AB, neutralize with phase D and after-homogenize. Cool to about 40° C., add phase E, homogenize again.

The example can be repeated in each case with the polymers 2 to 20 according to the invention. In each case, a face cleansing milk, O/W type with good properties is obtained.

Example 32

Peeling Cream, O/W Type

| | Phase A |
|---|---|
| 3.00 | Ceteareth-6 |
| 1.50 | Ceteareth-25 |
| 3.00 | Glyceryl stearate |
| 5.00 | Cetearyl alcohol, sodium cetearyl sulfate |
| 6.00 | Cetearyl octanoate |
| 6.00 | Mineral oil |
| 0.20 | Bisabolol |
| | Phase B |
| 2.00 | Propylene glycol |
| 0.10 | Disodium EDTA |
| 0.50 | Polymer from Example 1 (solid) |
| ad 100 | Dist. water |
| q.s. | Preservative |
| 59.70 | Dist. water |
| | Phase C |
| 0.50 | Tocopheryl acetate |
| q.s. | Perfume oil |
| | Phase D |
| 10.00 | Polyethylene |

Preparation:
Heat phases A and B separately to about 80° C. Stir phase B into phase A and homogenize Cool to about 40° C., add phase C and briefly homogenize again. Then stir in phase D.

The example can be repeated in each case with the polymers 2 to 20 according to the invention. In each case, a peeling cream, O/W type with good properties is obtained.

Example 33

Shaving Foam

| 6.00 | Ceteareth-25 |
|---|---|
| 5.00 | Poloxamer 407 |
| 52.00 | Dist. water |
| 1.00 | Triethanolamine |
| 5.00 | Propylene glycol |
| 1.00 | Lanolin oil-PEG-75 |
| 1.0 | Polymer from Example 1 (solid) |
| ad 100 | Dist. water |
| q.s. | Preservative |
| q.s. | Perfume oil |
| 25.00 | Sodium laureth sulfate |

Preparation:
Weigh everything together, then stir until dissolved. Bottling: 90 parts of active substance and 10 parts of 25:75 propane/butane mixture.

The example can be repeated in each case with the polymers 2 to 20 according to the invention. In each case, a shaving foam with good properties is obtained.

Example 34

Aftershave Balsam

| | Phase A |
|---|---|
| 0.25 | Acrylate/$C_{10-30}$ alkyl acrylate copolymer |
| 1.50 | Tocopheryl acetate |
| 0.20 | Bisabolol |
| 10.00 | Caprylic/Capric triglyceride |
| q.s. | Perfume oil |
| 1.00 | hydrogenated castor oil-PEG-40 |
| | Phase B |
| 1.00 | Panthenol |
| 15.00 | Alcohol |
| 5.00 | Glycerol |
| 0.05 | Hydroxyethylcellulose |
| 0.50 | Polymer from Example 1 (solid) |
| ad 100 | Dist. water |
| 64.00 | Dist. water |
| | Phase C |
| 0.08 | Sodium hydroxide |

Preparation:
Mix the components of phase A. Stir phase B into phase A with homogenization, briefly after-homogenize. Neutralize with phase C and homogenize again.

The example can be repeated in each case with the polymers 2 to 20 according to the invention. In each case, an aftershave balsam with good properties is obtained.

Example 35

Bodycare Cream

| | Phase A |
|---|---|
| 2.00 | Ceteareth-6 |
| 2.00 | Ceteareth-25 |
| 2.00 | Cetearyl alcohol |
| 3.00 | Glyceryl stearate SE |
| 5.00 | Mineral oil |
| 4.00 | Jojoba oil (*Buxus Chinensis*) |
| 3.00 | Cetearyl octanoate |
| 1.00 | Dimethicone |
| 3.00 | Mineral oil, Lanolin alcohol |
| | Phase B |
| 5.00 | Propylene glycol |
| 0.50 | Veegum |
| 1.00 | Panthenol |
| 1.70 | Polymer from Example 1 (solid) |
| ad 100 | Dist. water |
| 6.00 | Polyquaternium-44 (10% strength aqueous solution) |
| q.s. | Preservative |
| 54.00 | Dist. water |
| | Phase C |
| q.s. | Perfume oil |

Preparation:
Heat phases A and B separately to about 80° C. Homogenize phase B. Stir phase B into phase A with homogenization, briefly after-homogenize. Cool to about 40° C., add phase C and briefly homogenize again.

The example can be repeated in each case with the polymers 2 to 20 according to the invention. In each case, a bodycare cream with good properties is obtained.

Example 36

Toothpaste

| | Phase A |
|---|---|
| 34.79 | Dist. water |
| 0.50 | Polymer from Example 1 (solid) |
| ad 100 | Dist. water |

-continued

| | |
|---|---|
| 0.30 | Preservative |
| 20.00 | Glycerol |
| 0.76 | Sodium monofluorophosphate |
| | Phase B |
| 1.20 | Sodium carboxymethylcellulose |
| | Phase C |
| 0.80 | Aroma oil |
| 0.06 | Saccharin |
| 0.10 | Preservative |
| 0.05 | Bisabolol |
| 1.00 | Panthenol |
| 0.50 | Tocopheryl acetate |
| 2.80 | Silicon dioxide |
| 1.00 | Sodium lauryl sulfate |
| 7.90 | Dicalcium phosphate, anhydrous |
| 25.29 | Dicalcium phosphate dihydrate |
| 0.45 | Titanium dioxide |

Preparation:
Dissolve phase A. Sprinkle phase B into phase A and dissolve. Add phase C and leave to stir under reduced pressure at RT for about 45 min.

The example can be repeated in each case with the polymers 2 to 20 according to the invention. In each case, a toothpaste with good properties is obtained.

Example 37

Mouthwash

| | |
|---|---|
| | Phase A |
| 2.00 | Aroma oil |
| 4.00 | hydrogenated castor oil-PEG-40 |
| 1.00 | Bisabolol |
| 30.00 | Alcohol |
| | Phase B |
| 0.20 | Saccharin |
| 5.00 | Glycerol |
| q.s. | Preservative |
| 5.00 | Poloxamer 407 |
| 0.50 | Polymer from Example 1 (solid) |
| ad 100 | Dist. water |

Preparation:
Dissolve phase A and phase B separately to give clear solutions. Stir phase B into phase A.

The example can be repeated in each case with the polymers 2 to 20 according to the invention. In each case, a mouthwash with good properties is obtained.

Example 38

Denture Adhesive

| | |
|---|---|
| | Phase A |
| 0.20 | Bisabolol |
| 1.00 | Betacarotene |
| q.s. | Aroma oil |
| 20.00 | Cetearyl octanoate |
| 5.00 | Silicon dioxide |
| 33.80 | Mineral oil |
| | Phase B |
| 1.0 | Polymer from Example 1 (solid) |
| ad 100 | Dist. water |
| 35.00 | PVP (20% strength solution in water) |

Preparation:
Thoroughly mix phase A. Stir phase B into phase A.

The example can be repeated in each case with the polymers 2 to 20 according to the invention. In each case, a denture adhesive with good properties is obtained.

Example 39

Skincare Cream, O/W Type

| | |
|---|---|
| | Phase A |
| 8.00 | Cetearyl alcohol |
| 2.00 | Ceteareth-6 |
| 2.00 | Ceteareth-25 |
| 10.00 | Mineral oil |
| 5.00 | Cetearyl octanoate |
| 5.00 | Dimethicone |
| | Phase B |
| 0.50 | Polymer from Example 1 (solid) |
| ad 100 | Dist. water |
| 2.00 | Panthenol, Propylene glycol |
| q.s. | Preservative |
| | Phase C |
| q.s. | Perfume oil |

Preparation:
Heat phases A and B separately to about 80° C. Stir phase B into phase A with homogenization, briefly after-homogenize. Cool to about 40° C., add phase C, homogenize again.

The example can be repeated in each case with the polymers 2 to 20 according to the invention. In each case, a skincare cream, O/W type with good properties is obtained.

Example 40

Skincare Cream, W/O Type

| | |
|---|---|
| | Phase A |
| 6.00 | hydrogenated castor oil-PEG-7 |
| 8.00 | Cetearyl octanoate |
| 5.00 | Isopropyl myristate |
| 15.00 | Mineral oil |
| 2.00 | PEG-45/dodecyl glycol copolymer |
| 0.50 | Magnesium stearate |
| 0.50 | Aluminum stearate |
| | Phase B |
| 3.00 | Glycerol |
| 0.60 | Polymer from Example 1 (solid) |
| ad 100 | Dist. water |
| 0.70 | Magnesium sulfate |
| 2.00 | Panthenol |
| q.s. | Preservative |
| | Phase C |
| 1.00 | Tocopherol |
| 5.00 | Tocopheryl acetate |
| q.s. | Perfume oil |

Preparation:
Heat phases A and B separately to about 80° C. Stir phase B into phase A and homogenize. Cool to about 40° C., add phase C and briefly homogenize again.

The example can be repeated in each case with the polymers 2 to 20 according to the invention. In each case, a skincare cream, W/O type with good properties is obtained.

Example 41

Lipcare Cream

| | Phase A |
|---|---|
| 10.00 | Cetearyl octanoate |
| 5.00 | Polybutene |
| | Phase B |
| 0.10 | Carbomer |
| | Phase C |
| 2.00 | Ceteareth-6 |
| 2.00 | Ceteareth-25 |
| 2.00 | Glyceryl stearate |
| 2.00 | Cetyl alcohol |
| 1.00 | Dimethicone |
| 1.00 | Benzophenone-3 |
| 0.20 | Bisabolol |
| 6.00 | Mineral oil |
| | Phase D |
| 1.50 | Polymer from Example 1 (solid) |
| ad 100 | Dist. water |
| 3.00 | Panthenol |
| 3.00 | Propylene glycol |
| q.s. | Preservative |
| | Phase E |
| 0.10 | Triethanolamine |
| | Phase F |
| 0.50 | Tocopheryl acetate |
| 0.10 | Tocopherol |
| q.s. | Perfume oil |

Preparation:
Dissolve phase A to give a clear solution. Add phase B and homogenize. Add phase C and melt at 80° C. Heat phase D to 80° C. Add phase D to phase ABC and homogenize. Cool to about 40° C., add phase E and phase F, homogenize again.

The example can be repeated in each case with the polymers 2 to 20 according to the invention. In each case, a lipcare cream with good properties is obtained.

Example 42

Shower Gel

| 50.00 | Sodium Laureth Sulfate, Magnesium Laureth Sulfate, Sodium Laureth-8 Sulfate, Magnesium Laureth-8 |
|---|---|
| 1.00 | Cocoamide DEA |
| 0.8 | Polymer from Example 1 (solid) |
| ad 100 | Dist. water |
| 2.00 | Sodium Laureth Sulfate, Glycol Distearate, Cocamide MEA, Laureth-10 |
| q.s. | Preservative |
| q.s. | Perfume oil |
| 2.00 | Sodium chloride |

Preparation:
Weigh in all of the components together and stir until dissolved.

The example can be repeated in each case with the polymers 2 to 20 according to the invention. In each case, a shower gel with good properties is obtained.

Example 43

Shower Gel

| 30.00 | Sodium Laureth Sulfate |
|---|---|
| 6.00 | Sodium Cocoamphodiacetate |
| 6.00 | Cocamidopropylbetaine |
| 3.00 | Sodium Laureth Sulfate, Glycol Distearate, Cocamide MEA, Laureth-10 |
| 7.70 | Polyquaternium-44 |
| 0.2 | Polymer from Example 1 (solid) |
| ad 100 | Dist. water |
| 1.00 | Panthenol |
| q.s. | Preservative |
| q.s. | Perfume oil |
| q.s. | Citric acid |
| 0.50 | Sodium chloride |

Preparation:
Weigh in the components of phase A and dissolve, Adjust the pH to 6 to 7.

The example can be repeated in each case with the polymers 2 to 20 according to the invention. In each case, a shower gel with good properties is obtained.

Example 44

Clear Shower Gel

| 40.00 | Sodium Laureth Sulfate |
|---|---|
| 5.00 | Decyl glucoside |
| 5.00 | Cocamidopropylbetaine |
| 0.50 | Polyquaternium-10 |
| 2.00 | Polymer from Example 1 (solid) |
| ad 100 | Dist. water |
| 1.00 | Panthenol |
| q.s. | Perfume oil |
| q.s. | Preservative |
| q.s. | Citric acid |
| 2.00 | Sodium chloride |

Preparation:
Weigh in the components of phase A and dissolve to give a clear solution.

The example can be repeated in each case with the polymers 2 to 20 according to the invention. In each case, a clear shower gel with good properties is obtained.

Example 45

Shower Bath

| | A |
|---|---|
| 40.00 | Sodium Laureth Sulfate |
| 5.00 | Sodium $C_{12-15}$ Pareth-15 Sulfonate |
| 5.00 | Decyl glucoside |
| q.s. | Perfume oil |
| 0.10 | Phytantriol |
| | B |
| 0.1 | Guar hydroxypropyltrimonium chloride |
| 2.00 | Polymer from Example 1 (solid) |
| ad 100 | Dist. water |
| 1.00 | Panthenol |

-continued

| | |
|---|---|
| q.s. | Preservative |
| 1.00 | Laureth-3 |
| q.s. | Citric acid |
| 2.00 | Sodium chloride |

Preparation:

Mix the components of phase A. Add the components of phase B one after the other and mix. Adjust the pH to 6 to 7.

The example can be repeated in each case with the polymers 2 to 20 according to the invention. In each case, a shower bath with good properties is obtained.

Example 46

Liquid Soap

| | A |
|---|---|
| 43.26 | Dist. water |
| 0.34 | Aminomethylpropanol |
| 3.40 | Poly(ethyl acrylate/methacrylic acid) (Luviflex ® Soft, BASF) |
| | B |
| 40.00 | Sodium Laureth Sulfate |
| 10.00 | Cocamidopropylbetaine |
| 0.2 | Polymer from Example 1 (solid) |
| ad 100 | Dist. water |
| q.s. | Perfume oil |
| q.s. | Preservative |
| 2.00 | Sodium chloride |

Preparation:

Weigh in the components of phase A and dissolve to give a clear solution. Add the components of phase B one after the other and mix.

The example can be repeated in each case with the polymers 2 to 20 according to the invention. In each case, a liquid soap with good properties is obtained.

Example 47

Liquid Foot Bath

| | A |
|---|---|
| 1.00 | Nonoxynol-14 |
| 0.10 | Bisabolol |
| 1.00 | Pine oil (Pinus Sylvestris) |
| | B |
| 5.00 | PEG-8 |
| 1.50 | Polymer from Example 1 (solid) |
| ad 100 | Dist. water |
| 0.50 | Triclosan |
| 30.00 | Sodium Laureth Sulfate |
| 3.00 | Polyquaternium-16 |
| q.s. | C.I. 19 140 + C.I. 42 051 |

Preparation:
Solubilize phase A. Mix phase B.

The example can be repeated in each case with the polymers 2 to 20 according to the invention. In each case, a liquid foot bath with good properties is obtained.

Example 48

Freshening Gel

| | A |
|---|---|
| 0.60 | Carbomer |
| 45.40 | Dist. water |
| | B |
| 0.50 | Bisabolol |
| 0.50 | Farnesol |
| q.s. | Perfume oil |
| 5.00 | PEG-40 Hydrogenated Castor Oil |
| 0.50 | Polymer from Example 1 (solid) |
| ad 100 | Dist. water |
| 1.00 | Tetrahydroxypropylethylenediamine |
| 1.50 | Menthol |
| 43.00 | Alcohol |
| q.s. | C.I. 74 180, Direct Blue 86 |

Preparation:
Allow phase A to swell. Dissolve phase B. Stir phase B into phase A.

The example can be repeated in each case with the polymers 2 to 20 according to the invention. In each case, a freshening gel with good properties is obtained.

Example 49

Roll-On Antiperspirant

| | A |
|---|---|
| 0.40 | Hydroxyethylcellulose |
| 50.00 | Dist. water |
| | B |
| 25.00 | Alcohol |
| 0.10 | Bisabolol |
| 0.30 | Farnesol |
| 2.00 | PEG-40 Hydrogenated Castor Oil |
| q.s. | Perfume oil |
| | C |
| 5.00 | Aluminum chlorohydrate |
| 3.00 | Propylene glycol |
| 3.00 | Dimethicone copolyol |
| 3.00 | Polyquaternium-16 |
| 1.50 | Polymer from Example 1 (solid) |
| ad 100 | Dist. water |

Preparation:
Allow phase A to swell. Dissolve phase B and C separately. Stir phase A and B into phase C.

The example can be repeated in each case with the polymers 2 to 20 according to the invention. In each case, a roll-on antiperspirant with good properties is obtained.

Example 50

Transparent Deodorant Stick

| | |
|---|---|
| 5.00 | Sodium stearate |
| 0.50 | Triclosan |

| | |
|---|---|
| 3.00 | Ceteareth-25 |
| 20.00 | Glycerol |
| 0.50 | Polymer from Example 1 (solid) |
| ad 100 | Dist. water |
| q.s. | Perfume oil |
| 60.00 | Propylene glycol |
| 0.20 | Bisabolol |

Preparation:
Weigh phase A together, melt and homogenize. Then pour into the mold.

The example can be repeated in each case with the polymers 2 to 20 according to the invention. In each case, a transparent deodorant stick with good properties is obtained.

Example 51

Water-Soluble Bath Oil

| | |
|---|---|
| 15.00 | Cetearyl octanoate |
| 15.00 | Caprylic/Capric triglyceride |
| 1.00 | Panthenol, Propylene glycol |
| 0.10 | Bisabolol |
| 2.00 | Tocopheryl acetate |
| 2.00 | Retinyl palmitate |
| 0.10 | Tocopherol |
| 37.00 | PEG-7 glyceryl cocoate |
| 0.4 | Polymer from Example 1 (solid) |
| ad 100 | Dist. water |
| q.s. | Perfume oil |
| 23.60 | PEG-40 Hydrogenated Castor Oil |

Preparation:
Mix and stir until everything has dissolved to give a clear solution.

The example can be repeated in each case with the polymers 2 to 20 according to the invention. In each case, a water-soluble bath oil with good properties is obtained.

Example 52

Daycare Aerosol

| A | |
|---|---|
| 4.00 | Ethylhexyl methoxycinnamate |
| 1.50 | Octocrylene |
| 9.00 | Caprylic/Capric triglyceride |
| 5.00 | Simmondsia Chinensis (Jojoba) Seed Oil |
| 1.50 | Cyclomethicone |
| 3.00 | Hydrogenated Cocoglycerides |
| 1.00 | PVP/Hexadecene copolymer |
| 1.00 | Ceteareth-6, stearyl alcohol |

| B | |
|---|---|
| 5.00 | Zinc oxide |

| C | |
|---|---|
| 2.00 | Ceteareth-25 |
| 1.20 | Panthenol |
| 0.20 | Sodium Ascorbyl Phosphate |
| 0.30 | Imidazolidinylurea |
| 0.10 | Disodium EDTA |
| 1.50 | Polymer from Example 1 (solid) |
| ad 100 | Dist. water |

| D | |
|---|---|
| 0.50 | Tocopheryl acetate |
| 0.20 | Bisabolol |
| 0.33 | Caprylic/Capric triglyceride, Retinol |
| q.s. | Perfume oil |

Preparation:
Heat phase A to 80° C. Dissolve phase A to give a clear solution. Work in phase B and homogenize. Add phase C, heat to 80° C., melt and homogenize. Cool with stirring to about 40° C., add phase D and briefly homogenize. Bottle 90% active ingredient solution: 10% propane/butane at 3.5 bar (20° C.).

The example can be repeated in each case with the polymers 2 to 20 according to the invention. In each case, a daycare aerosol with good properties is obtained.

Example 53

Moisturizing Cream

| A | |
|---|---|
| 3.00 | Vitis Vinifera (Grape) Seed Oil |
| 1.00 | Cyclopentasiloxane, cyclohexasiloxane |
| 1.50 | Cyclomethicone |
| 2.00 | Soybean (Glycine Soya) Oil |
| 2.00 | Ethylhexyl methoxycinnamate |
| 1.00 | Uvinul ® A Plus |
| 1.00 | Hydrogenated Lecithin |
| 1.00 | Cholesterol |
| 2.00 | PEG-40 Hydrogenated Castor Oil |
| 5.00 | Cetearyl octanoate |
| 5.00 | Caprylic/Capric triglyceride |

| B | |
|---|---|
| 3.00 | Caprylic/Capric triglyceride, Acrylate copolymer |

| C | |
|---|---|
| 2.50 | Polymer from Example 1 (solid) |
| ad 100 | Dist. water |
| 0.50 | Cocotrimonium methosulfate |
| 2.00 | Panthenol, Propylene glycol |
| 3.00 | Glycerol |
| 0.10 | Disodium EDTA |

| D | |
|---|---|
| 0.30 | Perfume oil |
| 0.30 | DMDM Hydantoin |
| 1.00 | Tocopheryl acetate |
| 2.00 | Tocopherol |

Preparation:
Heat phase A to 80° C. Stir phase B into phase A. Heat phase C to about 80° C. and stir into phase A + B with homogenization. Cool to about 40° C. with stirring. Add phase D and briefly homogenize.

The example can be repeated in each case with the polymers 2 to 20 according to the invention. In each case, a moisturizing cream with good properties is obtained.

Example 54

Aerosol Hair Foam

| A | |
|---|---|
| 2.00 | Cocotrimonium methosulfate |
| 0.20 | Perfume oil |

| B | |
|---|---|
| 1.60 | Polymer from Example 1 (solid) |
| ad 100 | Dist. water |
| 0.50 | Poly(Ethylacrylate/methacrylic acid) (Luviflex ® Soft) |
| 0.10 | Aminomethylpropanol |
| 0.20 | Ceteareth-25 |

-continued

| | |
|---|---|
| 0.20 | Trimethylsilylamodimethicone, Trideceth-10, Cetrimonium Chloride |
| 0.10 | PEG-25 PABA |
| 0.20 | Hydroxyethylcellulose |
| 0.20 | PEG-8 |
| 0.20 | Panthenol |
| 15.00 | Alcohol |

C

| | |
|---|---|
| 10.00 | Propane/butane 3.5 bar (20° C.) |

Preparation:
Mix phases A and B and bottle with propellant gas.

The example can be repeated in each case with the polymers 2 to 20 according to the invention. In each case, an aerosol hair foam with good properties is obtained.

Example 55

Pump Mousse

A

| | |
|---|---|
| 2.00 | Cocotrimonium methosulfate |
| q.s. | Perfume oil |

C

| | |
|---|---|
| 7.00 | Polyquaternium-46 (10% strength aqueous solution) |
| 2.50 | Polymer from Example 1 (solid) |
| ad 100 | Dist. water |
| 0.50 | PEG-8 |
| 1.00 | Panthenol |
| q.s. | Preservative |
| 0.20 | PEG-25 PABA (ethoxylated p-aminobenzoic acid) |

Preparation:
Mix the components of phase A. Add the components of phase B one after the other and dissolve to give a clear solution.

The example can be repeated in each case with the polymers 2 to 20 according to the invention. In each case, a pump mousse with good properties is obtained.

Example 56

Aerosol Foam

| | |
|---|---|
| 3.0 | Polymer from Example 1 (solid) |
| ad 100 | Dist. water |
| 5.00 | PVP/VA-Copolymer (40% strength aqueous solution) |
| 0.50 | Hydroxyethylcetyldimonium phosphate |
| 0.20 | Ceteareth-25 |
| 0.40 | Perfume oil PC 910.781/Cremophor |
| q.s. | Preservative |
| 10.00 | Propane/butane 3.5 bar (20° C.) |

Preparation:
Weigh everything together, stir until dissolved, then bottle.

The example can be repeated in each case with the polymers 2 to 20 according to the invention. In each case, an aerosol foam with good properties is obtained.

Example 57

Color Styling Mousse

A

| | |
|---|---|
| 2.00 | Cocotrimonium methosulfate |
| q.s. | Perfume oil |

B

| | |
|---|---|
| 6.50 | Polymer from Example 1 (solid) |
| ad 100 | Dist. water |
| 0.50 | Acrylate copolymer (Luvimer ® 100 P, BASF) |
| 0.10 | Aminomethylpropanol |
| 0.20 | Ceteareth-25 |
| 0.20 | Panthenol |
| 0.20 | Hydroxyethylcellulose |
| 10.00 | Alcohol |
| 0.08 | C.I. 12245, Basic Red 76 |
| 0.05 | C.I. 42510, Basic Violet 14 |

C

| | |
|---|---|
| 10.00 | Propane/butane 3.5 bar (20° C.) |

Preparation:
Weigh everything together, stir until dissolved, then bottle. Only suitable for dark blonde and brown hair!

The example can be repeated in each case with the polymers 2 to 20 according to the invention. In each case, a color styling mousse with good properties is obtained.

Example 58

Pump Hair Foam

A

| | |
|---|---|
| 1.50 | Cocotrimonium methosulfate |
| q.s. | Perfume oil |

B

| | |
|---|---|
| 2.00 | Polymer from Example 1 (solid) |
| ad 100 | Dist. water |

C

| | |
|---|---|
| 0.46 | Aminomethylpropanol |
| 4.00 | PEG/PPG-25/25 Dimethicone/Acrylate copolymer |
| q.s. | Preservative |

Preparation:
Mix phase A. Stir phase B into phase A. Add phase C and stir until dissolved.

The example can be repeated in each case with the polymers 2 to 20 according to the invention. In each case, a pump hair foam with good properties is obtained.

Example 59

Aquawax

| | |
|---|---|
| 10 | Polymer from Example 1 (solid) |
| ad 100 | Dist. water |
| q.s. | Perfume oil |
| q.s. | hydrogenated castor oil-PEG-40 |
| 0.10 | Diethyl phthalate |

-continued

| | |
|---|---|
| 0.10 | Cetearyl ethylhexanoate |
| 0.10 | PEG-7 Glyceryl Cocoate |
| 0.10 | Preservative |
| 2.00 | Caprylic/Capric triglyceride, Acrylate copolymer |

Preparation:
Mix everything and homogenize. After-stir for 15 minutes.

The example can be repeated in each case with the polymers 2 to 20 according to the invention. In each case, an aquawax with good properties is obtained.

Example 60

Rinse-Off Conditioner and Repair Treatment

| | A |
|---|---|
| 0.20 | Cetearyl octanoate |
| 0.10 | Phytantriol |
| 2.00 | hydrogenated castor oil-PEG-40 |
| | B |
| q.s. | Perfume oil |
| 2.00 | Cocotrimonium methosulfate |
| | C |
| ad 100 | Dist. water |
| | D |
| 2.00 | Polyquaternium-16 (20% strength aqueous solution) |
| 1.0 | Polymer from Example 1 (solid) |
| 1.00 | Dimethicone copolyol |
| q.s. | Preservative |
| 10.00 | Alcohol |
| q.s. | Citric acid |

Preparation:
Mix phases A and B separately. Stir phase C into phase B.

The example can be repeated in each case with the polymers 2 to 20 according to the invention. In each case, a rinse-off conditioner and repair treatment with good properties is obtained.

Example 61

Hair Treatment

| | A |
|---|---|
| 2.00 | Ceteareth-6, Stearyl alcohol |
| 1.00 | Ceteareth-25 |
| 6.00 | Cetearyl alcohol |
| 6.00 | Cetearyl octanoate |
| 0.30 | Phytantriol |
| | B |
| 1.0 | Polymer from Example 1 (solid) |
| ad 100 | Dist. water |
| 0.70 | Guar hydroxypropyltrimonium chloride |
| 5.00 | Propylene glycol |
| 2.00 | Panthenol |
| 0.30 | Imidazolidinylurea |
| | C |
| 2.00 | Cosi Silk Soluble |
| 0.20 | Perfume |
| 0.50 | Phenoxyethanol |

Preparation:
Heat phases A and B separately to about 80° C. Homogenize phase B.

The example can be repeated in each case with the polymers 2 to 20 according to the invention. In each case, a hair treatment with good properties is obtained.

Example 62

Hair Cocktail

| | A |
|---|---|
| 0.40 | Acrylates/$C_{10-30}$ alkyl acrylate crosspolymer |
| 2.00 | Dimethicone |
| 3.00 | Cyclomethicone, dimethiconol |
| 2.00 | Phenyltrimethicone |
| 2.00 | Amodimethicone, Cetrimonium Chloride, Trideceth-10 |
| 0.50 | Dimethicone copolyol |
| 1.00 | Macadamia nut oil (Ternifolia) |
| 0.50 | Tocopheryl acetate |
| 1.00 | PEG-40 Hydrogenated Castor Oil |
| q.s. | Perfume oil |
| | B |
| 0.3 | Polymer from Example 1 (solid) |
| ad 100 | Dist. water |
| 0.46 | Aminomethylpropanol |
| 4.00 | PEG/PPG-25/25 Dimethicone/Acrylate copolymer |

Preparation:
Mix the components of phase A. Dissolve phase B. Stir phase B into phase A with homogenization.

The example can be repeated in each case with the polymers 2 to 20 according to the invention. In each case, a hair cocktail with good properties is obtained.

Example 63

Permanent Wave

| | Waving solution |
|---|---|
| | A |
| 0.20 | Cocamidopropylbetaine |
| 0.20 | Polysorbate 20 |
| 1.55 | Polymer from Example 1 (solid) |
| ad 100 | Dist. water |
| 0.20 | Disodium EDTA |
| 0.20 | Hydroxyethylcellulose |
| | B |
| 8.00 | Thioglycolic acid |
| | C |
| 11.00 | Ammonium hydroxide |
| | D |
| 5.00 | Ammonium carbonate |

Preparation:
Weigh in the components of phase A and dissolve to give a clear solution. Stir phase B into phase A.

The example can be repeated in each case with the polymers 2 to 20 according to the invention. In each case, a waving solution with good properties is obtained.

Example 64

Neutralizer

A

| | |
|---|---|
| 1.00 | PEG-40 Hydrogenated Castor Oil |
| 0.20 | Perfume oil |
| ad 100 | Dist. water |

B

| | |
|---|---|
| 0.20 | Cocamidopropylbetaine |
| 0.20 | Ceteareth-25 |
| 2.5 | Polymer from Example 1 (solid) |
| q.s. | Preservative |

C

| | |
|---|---|
| 2.30 | Hydrogen peroxide |

D

| | |
|---|---|
| q.s. | Phosphoric acid |

Preparation:
Solubilize phase A. Add the components of phase B one after the other and dissolve to give a clear solution.

The example can be repeated in each case with the polymers 2 to 20 according to the invention. In each case, a neutralizer with good properties is obtained.

Example 65

Dark Brown Permanent Hair Color (Oxidation Hair Color)

A

| | |
|---|---|
| 0.20 | Sodium sulfite |
| 0.05 | Disodium EDTA |
| 0.20 | p-Phenylenediamine |
| 0.30 | Resorcinol |
| 0.20 | 4-Amino-2-hydroxytoluene |
| 0.10 | m-Aminophenol |
| 1.50 | Oleyl alcohol |
| 4.50 | Propylene glycol |
| 2.30 | Sodium $C_{12-15}$ Pareth-15 Sulfonate |
| 20.00 | Oleic acid |
| ad 100 | Dist. water |

B

| | |
|---|---|
| 1.0 | Polymer from Example 1 (solid) |
| 13.70 | Ammonium hydroxide |
| 6.00 | isopropanol |
| q.s. | Perfume |

Preparation:
Solubilize phase A. Add the components of phase B one after the other and mix.

The example can be repeated in each case with the polymers 2 to 20 according to the invention. In each case, a dark brown permanent hair color (oxidation hair color) with good properties is obtained.

Example 66

Developer Emulsion (pH 3-4)

| | |
|---|---|
| 3.00 | Hexadecyl alcohol |
| 1.0 | Polymer from Example 1 (solid) |
| ad 100 | Dist. water |
| 1.00 | Ceteareth-20 |
| 1.00 | Sodium $C_{12-15}$ Pareth-15 Sulfonate |
| 6.00 | Hydrogen peroxide |
| 0.50 | Phosphoric acid |
| 0.01 | Acetanilide |

Preparation:
Add the components one after the other and mix.

The example can be repeated in each case with the polymers 2 to 20 according to the invention. In each case, a developer emulsion (pH 3-4) with good properties is obtained.

Example 67

Pale Brown Semipermanent Hair Color

| | |
|---|---|
| 10.00 | Cocodiethanolamide |
| 4.00 | Sodium dodecylbenzylsulfonate, 50% strength |
| 1.0 | Polymer from Example 1 (solid) |
| ad 100 | Dist. water |
| 6.00 | $C_{9-11}$ Pareth-3 |
| 2.50 | Sodium lauryl sulfate |
| 0.40 | 2-Nitro-p-phenylenediamine |
| 0.20 | HC Red No. 3 |
| 0.20 | HC Yellow No. 2 |

Preparation:
Add the components one after the other and mix.

The example can be repeated in each case with the polymers 2 to 20 according to the invention. In each case, a pale brown semipermanent hair color with good properties is obtained.

Example 68

Shampoo

| | |
|---|---|
| 30.00 | Sodium Laureth Sulfate |
| 6.00 | Sodium Cocoamphoacetate |
| 6.00 | Cocamidopropylbetaine |
| 3.00 | Sodium Laureth Sulfate, Glycol Distearate, Cocamide MEA, Laureth-10 |
| 1.0 | Polymer from Example 1 (solid) |
| 2.00 | Dimethicone |
| q.s. | Perfume |
| q.s. | Preservative |
| q.s. | Citric acid |
| 1.00 | Sodium chloride |
| ad 100 | Dist. water |

Preparation:
Weigh in and dissolve the components. Adjust pH to 6 to 7.

The example can be repeated in each case with the polymers 2 to 20 according to the invention. In each case, a shampoo with good properties is obtained.

Example 69

Shampoo

| | |
|---|---|
| 30.00 | Sodium Laureth Sulfate |
| 6.00 | Sodium Cocoamphoacetate |
| 6.00 | Cocamidopropylbetaine |
| 3.00 | Sodium Laureth Sulfate, Glycol Distearate, Cocamide MEA, Laureth-10 |
| 1.0 | Polymer from Example 1 (solid) |
| 2.00 | Amodimethicone |
| q.s. | Perfume |
| q.s. | Preservative |
| q.s. | Citric acid |
| 1.00 | Sodium chloride |
| ad 100 | Dist. water |

Preparation:
Weigh in and dissolve the components. Adjust pH to 6 to 7.

The example can be repeated in each case with the polymers 2 to 20 according to the invention. In each case, a shampoo with good properties is obtained.

Example 70

Shampoo

| | |
|---|---|
| 40.00 | Sodium Laureth Sulfate |
| 10.00 | Cocamidopropylbetaine |
| 3.00 | Sodium Laureth Sulfate, Glycol Distearate, Cocamide MEA, Laureth-10 |
| 1.0 | Polymer from Example 1 (solid) |
| 2.00 | Dow Corning 3052 |
| q.s. | Perfume |
| q.s. | Preservative |
| q.s. | Citric acid |
| 2.00 | Cocamido DEA |
| ad 100 | Dist. water |

Preparation:
Weigh in and dissolve the components. Adjust the pH to 6 to 7.

The example can be repeated in each case with the polymers 2 to 20 according to the invention. In each case, a shampoo with good properties is obtained.

Example 71

Antidandruff Shampoo

| | |
|---|---|
| 40.00 | Sodium Laureth Sulfate |
| 10.00 | Cocamidopropylbetaine |
| 10.00 | Disodium Laureth Sulfosuccinate |
| 2.50 | Sodium Laureth Sulfate, Glycol Distearate, Cocamide MEA, Laureth-10 |
| 1.0 | Polymer from Example 1 (solid) |
| 0.50 | Climbazole |
| q.s. | Perfume |
| q.s. | Preservative |
| 0.50 | Sodium chloride |
| ad 100 | Dist. water |

Preparation:
Weigh in and dissolve the components. Adjust the pH to 6 to 7.

The example can be repeated in each case with the polymers 2 to 20 according to the invention. In each case, an antidandruff shampoo with good properties is obtained.

Example 72

Shampoo

| | |
|---|---|
| 25.00 | Sodium Laureth Sulfate |
| 5.00 | Cocamidopropylbetaine |
| 2.50 | Sodium Laureth Sulfate, Glycol Distearate, Cocamide MEA, Laureth-10 |
| 1.0 | Polymer from Example 1 (solid) |
| q.s. | Perfume |
| q.s. | Preservative |
| 2.00 | Cocamido DEA |
| ad 100 | Dist. water |

Preparation:
Weigh in and dissolve the components. Adjust the pH to 6 to 7.

The example can be repeated in each case with the polymers 2 to 20 according to the invention. In each case, a shampoo with good properties is obtained.

Example 73

Shampoo

| | |
|---|---|
| 20.00 | Ammonium Laureth Sulfate |
| 15.00 | Ammonium Lauryl Sulfate |
| 5.00 | Cocamidopropylbetaine |
| 2.50 | Sodium Laureth Sulfate, Glycol Distearate, Cocamide MEA, Laureth-10 |
| 1.0 | Polymer from Example 1 (solid) |
| q.s. | Perfume |
| q.s. | Preservative |
| 0.50 | Sodium chloride |
| ad 100 | Dist. water |

Preparation:
Weigh in and dissolve the components. Adjust the pH to 6 to 7.

The example can be repeated in each case with the polymers 2 to 20 according to the invention. In each case, a shampoo with good properties is obtained.

Example 74

Clear Shower Gel

| | |
|---|---|
| 40.00 | Sodium Laureth Sulfate |
| 5.00 | Decyl glucoside |
| 5.00 | Cocamidopropylbetaine |
| 1.0 | Polymer from Example 1 (solid) |
| 1.00 | Panthenol |
| q.s. | Perfume |
| q.s. | Preservative |
| q.s. | Citric acid |
| 2.00 | Sodium chloride |
| ad 100 | Dist. water |

Preparation:
Weigh in and dissolve the components. Adjust the pH to 6 to 7.

The example can be repeated in each case with the polymers 2 to 20 according to the invention. In each case, a clear shower gel with good properties is obtained.

Example 75

Shampoo

| | |
|---|---|
| 12.00 | Sodium Laureth Sulfate |
| 1.50 | Decyl glucoside |
| 2.50 | Cocamidopropylbetaine |
| 5.00 | Cocoglucoside Glyceryl Oleate |
| 2.00 | Sodium Laureth Sulfate, Glycol Distearate, Cocamide MEA, Laureth-10 |
| 1.0 | Polymer from Example 1 (solid) |
| q.s. | Preservative |
| q.s. | Sunset Yellow C.I. 15 985 |
| q.s. | Perfume |
| 1.00 | Sodium chloride |
| ad 100 | Dist. water |

Preparation:
Weigh in and dissolve the components. Adjust the pH to 6 to 7.

The example can be repeated in each case with the polymers 2 to 20 according to the invention. In each case, a shampoo with good properties is obtained.

Example 76

Shampoo

| | |
|---|---|
| A | |
| 40.00 | Sodium Laureth Sulfate |
| 5.00 | Sodium $C_{12-15}$ Pareth-15 Sulfonate |
| 5.00 | Decyl glucoside |
| q.s. | Perfume |
| 0.10 | Phytantriol |
| B | |
| 1.0 | Polymer from Example 1 (solid) |
| ad 100 | Dist. water |
| 1.00 | Panthenol |
| q.s. | Preservative |
| 1.00 | Laureth-3 |
| q.s. | Citric acid |
| 2.00 | Sodium chloride |

Preparation:
Weigh in and dissolve the components of phase A. Adjust the pH to 6 to 7. Add phase B and mix.

The example can be repeated in each case with the polymers 2 to 20 according to the invention. In each case, a shampoo with good properties is obtained.

We claim:
1. An aqueous skin or hair cosmetic preparation comprising at least one polymer A which comprises, in copolymerized form:
   a) methyl methacrylate;
   b) acrylic acid and methacrylic acid;
   c) at least one olefinically unsaturated free-radically polymerizable urethane-group-containing monomer which comprises no silicone groups
      wherein said at least one olefinically unsaturated free-radically polymerizable urethane-group-containing monomer is a urethane (meth)acrylate monomer comprising, in incorporated form,
      1) at least one monomer comprising at least one active hydrogen atom and at least one free-radically polymerizable α,β-ethylenically unsaturated double bond per molecule,
      2) at least one diisocyanate, and
      3) at least one compound comprising two active hydrogen atoms per molecule,
      and salts thereof,
      wherein said at least one compound comprising two active hydrogen atoms per molecule is a polyesterdiol III having a number-average molecular weight in the range from about 400 to about 5000; and
   d) optionally further free-radically polymerizable compounds.

2. The aqueous skin or hair cosmetic preparation of claim 1, wherein said at least one polymer A comprises, in copolymerized form,
   a) 50-95% by weight of methyl methacrylate;
   b) 4-30% by weight of acrylic acid and methacrylic acid;
   c) 0.1-20% by weight of at least one olefinically unsaturated free-radically polymerizable urethane-group-containing monomer which comprises no silicone groups
      wherein said at least one olefinically unsaturated free-radically polymerizable urethane-group-containing monomer is a urethane (meth)acrylate monomer comprising, in incorporated form,
      1) at least one monomer comprising at least one active hydrogen atom and at least one free-radically polymerizable α,β-ethylenically unsaturated double bond per molecule,
      2) at least one diisocyanate, and
      3) at least one compound comprising two active hydrogen atoms per molecule,
      and salts thereof,
      wherein said at least one compound comprising two active hydrogen atoms per molecule is a polyesterdiol III having a number-average molecular weight in the range from about 400 to about 5000; and
   d) 0-30% by weight of further free-radically polymerizable compounds; with the proviso that the amounts of a), b), c), and d) add up to 100% by weight.

3. The aqueous skin or hair cosmetic preparation of claim 2, wherein said at least one polymer A comprises, in copolymerized form,
   a) 65-85% by weight of methyl methacrylate;
   b) 10-30% by weight of acrylic acid and methacrylic acid;
   c) 0.5-10% by weight of at least one olefinically unsaturated free-radically polymerizable urethane-group-containing monomer which comprises no silicone groups
      wherein said at least one olefinically unsaturated free-radically polymerizable urethane-group-containing monomer is a urethane (meth)acrylate monomer comprising, in incorporated form,
      1) at least one monomer comprising at least one active hydrogen atom and at least one free-radically polymerizable α,β-ethylenically unsaturated double bond per molecule,
      2) at least one diisocyanate, and
      3) at least one compound comprising two active hydrogen atoms per molecule,
      and salts thereof,
      wherein said at least one compound comprising two active hydrogen atoms per molecule is a polyesterdiol III having a number-average molecular weight in the range from about 400 to about 5000; and
   d) 0-30% by weight of further free-radically polymerizable compounds;

with the proviso that the amounts of a), b), c), and d) add up to 100% by weight.

4. The aqueous skin or hair cosmetic preparation of claim 1, wherein said at least one polymer A comprises, in copolymerized form,
   a) 70-80% by weight of methyl methacrylate;
   b) 15-28% by weight of acrylic acid and methacrylic acid;
   c) 0.5-5% by weight of urethane-group-containing (meth)acrylates comprising, in incorporated form,
      1) at least one monomer comprising at least one active hydrogen atom and at least one free-radically polymerizable $\alpha,\beta$-ethylenically unsaturated double bond per molecule,
      2) at least one diisocyanate, and
      3) at least one compound comprising two active hydrogen atoms per molecule,
      and salts thereof,
      wherein said at least one compound comprising two active hydrogen atoms per molecule is a polyesterdiol III having a number-average molecular weight in the range from about 400 to about 5000;
   d) 0-30% by weight of further free-radically polymerizable compounds;
   with the proviso that the amounts of a), b), c), and d) add up to 100% by weight.

5. The aqueous skin or hair cosmetic preparation of claim 1, wherein said preparation comprises, apart from water, at least one further cosmetically acceptable carrier B) which is selected from the group consisting of
   i. water-miscible organic solvents;
   ii. oils, fats, waxes;
   iii. esters of $C_6$-$C_{30}$-monocarboxylic acids with mono-, di- or trihydric alcohols which are different from ii.;
   iv. saturated acyclic and cyclic hydrocarbons;
   v. fatty acids;
   vi. fatty alcohols;
   vii. propellants; and
   viii. mixtures thereof.

6. The aqueous skin or hair cosmetic preparation of claim 5, wherein i. is $C_2$-$C_4$-alkanols.

7. The aqueous skin or hair cosmetic preparation of claim 5, wherein i. is ethanol.

8. The aqueous skin or hair cosmetic preparation of claim 1, wherein said preparation is in the form of a spray product, wherein said preparation is present either in combination with a mechanical pump spray device or in combination with at least one propellant selected from the group consisting of propane, butane, dimethyl ether, fluorinated hydrocarbons, and mixtures thereof.

* * * * *